(12) United States Patent
Waldo et al.

(10) Patent No.: US 7,585,636 B2
(45) Date of Patent: Sep. 8, 2009

(54) PROTEIN SUBCELLULAR LOCALIZATION ASSAYS USING SPLIT FLUORESCENT PROTEINS

(75) Inventors: Geoffrey S. Waldo, Santa Fe, NM (US); Stephanie Cabantous, Los Alamos, NM (US)

(73) Assignee: Los Alamos National Security, LLC, Los Alamos, NM (US)

( * ) Notice: Subject to any disclaimer, the term of this patent is extended or adjusted under 35 U.S.C. 154(b) by 0 days.

(21) Appl. No.: 11/295,374

(22) Filed: Dec. 5, 2005

(65) Prior Publication Data
US 2006/0257942 A1 Nov. 16, 2006

Related U.S. Application Data

(60) Provisional application No. 60/633,488, filed on Dec. 4, 2004.

(51) Int. Cl.
*G01N 33/567* (2006.01)
*G01N 33/53* (2006.01)
*C12Q 1/68* (2006.01)

(52) U.S. Cl. .............................. 435/7.1; 435/6; 435/7.2; 435/320.1; 435/325; 435/455; 435/69.1; 530/350; 536/23.5

(58) Field of Classification Search .................. 514/12; 530/350
See application file for complete search history.

(56) References Cited

U.S. PATENT DOCUMENTS

| 6,780,599 | B2 | 8/2004 | Hamilton et al. ............. 435/7.1 |
| 2002/0110834 | A1* | 8/2002 | Benkovic et al. ............. 435/7.1 |
| 2002/0146701 | A1* | 10/2002 | Hamilton et al. ............... 435/6 |
| 2003/0049712 | A1* | 3/2003 | Haugwitz ..................... 435/23 |
| 2004/0002065 | A1* | 1/2004 | Thomas et al. ................. 435/6 |
| 2004/0137528 | A1* | 7/2004 | Watson Michnick et al. . 435/7.1 |
| 2004/0161787 | A1* | 8/2004 | Michnick et al. ............... 435/6 |

FOREIGN PATENT DOCUMENTS

WO WO/2005052588 A2 * 6/2005

OTHER PUBLICATIONS

Prieve et al., "Differential Importin-α Recognition and Nuclear Transport by Nuclear Localization Signals within the High-Mobility-Group DNA Binding Domains of Lymphoid Enhancer Factor 1 and T-Cell Factor 1," Mol. Cell. Biology, Aug. 1998, p. 4819-4832.*
Li et al., "Protein-Protein Interaction of FHL3 with FHL2 and Visualization of Their Interaction by Green Fluorescent Proteins (GFP) Two-Fusion fluorescence Resonance Energy Transfer (FRET)," J. Cell. Biochem. 80:293-303 (2001).*
Liu et al., "Nuclear Localization of the ORF2 Protein Encoded by Porcine Circovirus Type 2," Virology, 285, 91-99 (2001).*
Hu et al., "Visualizaton of Interactions among bZIP and Rel Family Proteins in Living Cells Using Bimolecular Fluorescence Complementation," Molecular Cell,vol. 9, 789-798, Apr. 2002.*
Ghosh et al., 2000, J. Am. Chem. Soc. 122: 5658.
Hu et al., 2002, Mol. Cell 9: 789.
Nagai et al., 2001, Proc. Natl. Acad. Sci. USA 98: 3197.
Ozawa et al., 2000, Anal. Chem. 72: 5157.
Ozawa et al, 2002, Anal. Chem. 73: 5866.
Umezawa, 2003, Chem. Rec. 3: 22.
Zhang et al., 2004, Cell 119: 137.
Kalderon et al., 1984, Cell 39 (3 Pt2): 499.
Lanford et al., 1986, Cell 46(4): 575.
Watzele and Berger, 1990, Nucleic Acids Res. 18(23): 7174.
Yamaguchi and Fukuda, 1995, J. Biol. Chem. 270(20): 12170.
Liopis et al., 1998, Proc. Natl. Acad. Sci. USA 95(12): 6803.
Rizzuto et al., 1989, J. Biol. Chem 264(18): 10595.
Rizzuto et al., 1995, Curr. Biol. 5(6): 635.
Munro and Pelham, 1987, Cell 48(5): 899.
Fliegel et al., 1989, J. Biol. Chem. 264(36): 21522.
Prieve et al., 1998, Mol. Cell. Biology 18(8), Aug. 1998, 4819.
Li et al., 2001, J. Cell. Biochem. 80:293 (see pp. 294 and 297).
Liu et al., 2001, Virology 285: 91 (see p. 93).
International Application Publication WO 2005/052588 A2, Queens University of Belfast, Jun. 9, 2005.

* cited by examiner

*Primary Examiner*—Lisa J Hobbs
(74) *Attorney, Agent, or Firm*—Kenneth K. Sharples

(57) ABSTRACT

The invention provides protein subcellular localization assays using split fluorescent protein systems. The assays are conducted in living cells, do not require fixation and washing steps inherent in existing immunostaining and related techniques, and permit rapid, non-invasive, direct visualization of protein localization in living cells. The split fluorescent protein systems used in the practice of the invention generally comprise two or more self-complementing fragments of a fluorescent protein, such as GFP, wherein one or more of the fragments correspond to one or more beta-strand microdomains and are used to "tag" proteins of interest, and a complementary "assay" fragment of the fluorescent protein. Either or both of the fragments may be functionalized with a subcellular targeting sequence enabling it to be expressed in or directed to a particular subcellular compartment (i.e., the nucleus).

14 Claims, 8 Drawing Sheets

FIG. 7B

```
TCGAGTCCCTATCAGTGATAGAGATTGACATCCCTATCAGTGATAGAGATACTGAGCACATCAGCAGGACGCACTGA
CCGAGTTCATTAAAGAGGAGAAAGATACCCATGGGCAGCAGCCATCATCATCATCATCACAGCAGCGGCCTGGTGCC
GCGCGGCAGCCATATGGGTGGCGGTTCTGGATCCGGAGGCACTAGTGGTGGCGGCTCAGGTACCTAACTCGAGCACC
ACCACCACCACCACTGAGATCCGGCTGCTAACAAAGCCCGAAAGGAAGCTGAGTTGGCTGCTGCCACCGCTGAGCAA
TAACTAGCATAACCTCTAGAGGCATCAAATAAAACGAAAGGCTCAGTCGAAAGACTGGGCCTTTCGTTTTATCTGTT
GTTTGTCGGTGAACGCTCTCCTGAGTAGGACAAATCCGCCGCCCTAGACCTAGGCGTTCGGCTGCGGCGAGCGGTAT
CAGCTCACTCAAAGGCGGTAATACGGTTATCCACAGAATCAGGGGATAACGCAGGAAAGAACATGTGAGCAAAAGGC
CAGCAAAAGGCCAGGAACCGTAAAAAGGCCGCGTTGCTGGCGTTTTTCCATAGGCTCCGCCCCCCTGACGAGCATCA
CAAAAATCGACGCTCAAGTCAGAGGTGGCGAAACCCGACAGGACTATAAAGATACCAGGCGTTTCCCCCTGGAAGCT
CCCTCGTGCGCTCTCCTGTTCCGACCCTGCCGCTTACCGGATACCTGTCCGCCTTTCTCCCTTCGGGAAGCGTGGCG
CTTTCTCAATGCTCACGCTGTAGGTATCTCAGTTCGGTGTAGGTCGTTCGCTCCAAGCTGGGCTGTGTGCACGAACC
CCCCGTTCAGCCCGACCGCTGCGCCTTATCCGGTAACTATCGTCTTGAGTCCAACCCGGTAAGACACGACTTATCGC
CACTGGCAGCAGCCACTGGTAACAGGATTAGCAGAGCGAGGTATGTAGGCGGTGCTACAGAGTTCTTGAAGTGGTGG
CCTAACTACGGCTACACTAGAAGGACAGTATTTGGTATCTGCGCTCTGCTGAAGCCAGTTACCTTCGGAAAAAGAGT
TGGTAGCTCTTGATCCGGCAAACAAACCACCGCTGGTAGCGGTGGTTTTTTGTTTGCAAGCAGCAGATTACGCGCA
GAAAAAAGGATCTCAAGAAGATCCTTTGATCTTTTCTACGGGGTCTGACGCTCAGTGGAACGAAAACTCACGTTAA
GGGATTTTGGTCATGACTAGCGCTTGGATTCTCACCAATAAAAAACGCCCGGCGGCAACCGAGCGTTCTGAACAAAT ⌐1
CCAGATGGAGTTCTGAGGTCATTACTGGATCTATCAACAGGAGTCCAAGCTTAAGACCCACTTTCACATTTAAGTTG
TTTTTCTAATCCGTATATGATCAATTCAAGGCCGAATAAGAAGGCTGGCTCTGCACCTTGGTGATCAAATAATTCGA
TAGCTTGTCGTAATAATGGCGGCATACTATCCAGTAGTAGGTGTTTCCCTTTCTTCTTTTAGCGACTTGATGCTCTTGA
TCTTCCAATACGCAACCTAAAGTAAAATGCCCCACAGCGCTGAGTGCATATAATGCATTCTCTAGTGAAAAACCTTG ⌐2
TTGGCATAAAAAGGCTAATTGATTTTCGAGAGTTTCATACTGTTTTTCTGTAGGCCGTGTACCTAAATGTACTTTTG
CTCCATCGCGATGACTTAGTAAAGCACATCTAAAACTTTTAGCGTTATTACGTAAAAAATCTTGCCAGCTTTCCCCT
TCTAAAGGGCAAAAGTGAGTATGGTGCCTATCTAACATCTCAATGGCTAAGGCGTCGAGCAAAGCCCGCTTATTTTT
TACATGCCAATACAATGTAGGCTGCTCTACACCTAGCTTCTGGGCGAGTTTACGGGTTGTTAAACCTTCGATTCCGA
CCTCATTAAGCAGCTCTAATGCGCTGTTAATCACTTTACTTTTATCTAATCTGGACATCATTAATGTTTATTGAGCT ⌐3
CTCGAACCCCAGAGTCCCGCATTATTTGCCGACTACCTTGGTGATCTCGCCTTTCACGTAGTGGACAAATTCTTCCA
ACTGATCTGCGCGCGAGGCCAAGCGATCTTCTTCTTGTCCAAGATAAGCCTGTCTAGCTTCAAGTATGACGGGCTGA
TACTGGGCCGGCAGGCGCTCCATTGCCCAGTCGGCAGCGACATCCTTCGGCGCGATTTTGCCGGTTACTGCGCTGTA
CCAAATGCGGGACAACGTAAGCACTACATTTCGCTCATCGCCAGCCCAGTCGGGCGGCGAGTTCCATAGCGTTAAGC
TTTCATTTAGCGCCTCAAATAGATCCTGTTCAGGAACCGGATCAAAGAGTTCCTCCGCCGCTGGACCTACCAAGGCA
ACGCTATGTTCTCTTGCTTTTGTCAGCAAGATAGCCAGATCAATGTCGATCGTGGCTGGCTCGAAGATACCTGCAAG
AATGTCATTGCGCTGCCATTCTCCAAATTGCAGTTCGCGCTTAGCTGGATAACGCCACGGAATGATGTCGTCGTGCA ⌐4
CAACAATGGTGACTTCTACAGCGCGGAGAATCTCGCTCTCTCCAGGGGAAGCCGAAGTTTCCAAAAGGTCGTTGATC
AAAGCTCGCCGCGTTGTTTCATCAAGCCTTACGGTCACCGTAACCAGCAAATCAATATCACTGTGTGGCTTCAGGCC
GCCATCCACTGCGGAGCCGTACAAATGTACGGCCAGCAACGTCGGTTCGAGATGGCGCTCGATGACGCCAACTACCT
CTGATAGTTGAGTCGATACTTCGGCGATCACCGCTTCCCTCATGATGTTTAACTTTGTTTTAGGGCGACTGCCCTGC
TGCGTAACATCGTTGCTGCTCCATAACATCAAACATCGACCCACGGCGTAACGCGCTTGCTGCTTGGATGCCCGAGG
CATAGACTGTACCCAAAAAAACATGTCATAACAAGCCATGAAAACCGCCACTGCGCCGTTACCATGCGAAACGATC
CTCATCCTGTCTCTTGATCAGATCTTGATCCCCTGCGCCATCAGATCCTTGGCGGCAAGAAAGCCATCCAGTTTACT ⌐5
TTGCAGGGCTTCCCAACCTTACCAGAGGGCGCCCCAGCTGGCAATTCCGACGTCTAAGAAACCATTATTATCATGAC
ATTAACCTATAAAAATAGGCGTATCACGAGGCCCTTTCGTCTTCACC
```

PROTEIN SUBCELLULAR LOCALIZATION ASSAYS USING SPLIT FLUORESCENT PROTEINS

RELATED APPLICATION

This patent application claims the benefit of the filing date of U.S. Provisional patent application No. 60/633,488, filed Dec. 4, 2004. The subcellular localization assays of the invention utilize split-fluorescent and split-chromophoric protein systems, which are described in co-owned, co-pending U.S. patent application Ser. No. 10/973,693, entitled "SELF-ASSEMBLING SPLIT-FLUORESCENT PROTEIN SYSTEMS", filed Oct. 25, 2004 and hereby incorporated by reference in its entirety.

STATEMENT AS TO RIGHTS TO INVENTIONS MADE UNDER FEDERALLY SPONSORED RESEARCH OR DEVELOPMENT

This invention was made with government support under Contract No. W-7405-ENG-36 awarded by the United States Department of Energy to The Regents of The University of California. The government has certain rights in this invention.

BACKGROUND OF THE INVENTION

Understanding the intracellular transport and localization of proteins is important because many processes in biology, including transcription, translation, and metabolic or signal transduction pathways, are mediated by proteins and non-covalently-associated multiprotein complexes localized to particular cellular compartments Reed, L. J. (1974) *Multienzyme Complexes*. Acc. Chem. Res. 7, 40-46. Proteins and protein complexes are the workhorses of the chemical machinery in living systems and define the interface between metabolic pathways, signaling pathways, and the response of cells to the environment. Since the completion of the genome sequencing projects, the focus of biological research has moved to identifying proteins involved in cellular processes, determining their functions and how, when, and where they localize to facilitate interaction with other proteins involved in specific pathways. Further, with rapid advances in genome sequencing projects there is a need to develop strategies to define "protein linkage maps", detailed inventories of protein interactions that make up functional assemblies of proteins Lander, E. S. (1996) *The new genomics—global views of biology*. Science 274, 536-539; Evangelista, C., Lockshon, D. & Fields, S. (1996) *The yeast two-hybrid system—prospects for protein linkage maps*. Trends in Cell Biology 6, 196-199. Eukaryotic cells have specialized compartments containing specific proteins needed to carry out defined processes. Understanding when and where specific proteins localize is key to further understanding of cellular processes.

GFP and its numerous related fluorescent proteins are now in widespread use as protein tagging agents (for review, see Verkhusha et al., 2003, *GFP-like fluorescent proteins and chromoproteins of the class Anthozoa*. In: Protein Structures: Kaleidescope of Structural Properties and Functions, Ch. 18, pp. 405-439, Research Signpost, Kerala, India), and have been used to visualize protein trafficking in living cells (Llopis, McCaffery et al. 1998; Southward and Surette 2002). Generally, using existing methodologies, a gene of interest is expressed in fusion with GFP and the fusion protein localizes fluorescence to the normal localization of the target protein. The fusion protein may be encoded by a constitutive promoter on a plasmid or may be directly transfected into the cell by any transfection methodology (FIG. 1). A number of localization vectors expressing fluorescent proteins fused to subcellular localization sequences or tags have been described and/or are commercially available (e.g., the Living Colors™ localization vectors, BD Biosciences Clontech, Palo Alto, Calif.)

However, although protein localization methods using GFP fused to a protein of interest have been useful, these methods provide limited information and are compromised by problems inherent in using a relatively large terminally fused reporter protein tag. In particular, GFP and related fluorescent proteins may cause misfolding of the fused protein, and may interfere with protein processing and/or intracellular transport. Misfolding of the reporter can result in the generation of insoluble aggregates of the fusion, which may be unable to freely move through intracellular processing and transport systems within the cell. Additionally, GFP fusions may alter biophysical properties of a test protein, resulting in a default in the corresponding localization pathway (Hanson and Ziegler, 2004). In general, the use of GFP fusions in extracytoplasmic compartments has been limited because of export deficiencies. As an example, efforts to obtain functional GFP following export through the sec-dependent pathway failed because of improper folding of the protein; the secreted fraction of GFP was not fluorescent (Feilmeier, Iseminger et al. 2000; Tanudji, Hevi et al. 2002). Accordingly, it is difficult to obtain a true picture of a test protein's trafficking or distribution within a cell using terminal GFP fusion tags, and systems capable of visualizing subcellular compartmentalization through a wider lens and over time are needed.

GFP fragment reconstitution systems have been described, mainly for detecting protein-protein interactions, but none are capable of unassisted self-assembly into a correctly-folded, soluble and fluorescent re-constituted GFP, and no general split GFP folding reporter system has emerged from these approaches. For example, Ghosh et al, 2000, reported that two GFP fragments, corresponding to amino acids 1-157 and 158-238 of the GFP structure, could be reconstituted to yield a fluorescent product, in vitro or by coexpression in *E. coli*, when the individual fragments were fused to coiled-coil sequences capable of forming an antiparallel leucine zipper (Ghosh et al., 2000, *Antiparallel leucine zipper-directed protein reassembly: application to the green fluorescent protein*. J. Am. Chem. Soc. 122: 5658-5659). Likewise, U.S. Pat. No. 6,780,599 describes the use of helical coils capable of forming anti-parallel leucine zippers to join split fragments of the GFP molecule. The patent specification establishes that reconstitution does not occur in the absence of complementary helical coils attached to the GFP fragments. In particular, the specification notes that control experiments in which GFP fragments without leucine zipper pairs "failed to show any green colonies, thus emphasizing the requirement for the presence of both NZ and CZ leucine zippers to mediate GFP assembly in vivo and in vitro."

Similarly, Hu et al., 2002, showed that the interacting proteins bZIP and Rel, when fused to two fragments of GFP, can mediate GFP reconstitution by their interaction (Hu et al., 2002, *Visualization of interactions among bZIP and Rel family proteins in living cells using bimolecular fluorescence complementation*. Mol. Cell 9: 789-798). Nagai et al., 2001, showed that fragments of yellow fluorescent protein (YFP) fused to calmodulin and M13 could mediate the reconstitution of YFP in the presence of calcium (Nagai et al., 2001, *Circularly permuted green fluorescent proteins engineered to sense $Ca^2+$*. Proc. Natl. Acad. Sci. USA 98: 3197-3202). In a variation of this approach, Ozawa at al. fused calmodulin and M13 to two GFP fragments via self-splicing intein polypeptide sequences, thereby mediating the covalent reconstitution of the GFP fragments in the presence of calcium (Ozawa et al., 2001, *A fluorescent indicator for detecting protein-protein interactions in vivo based on protein splicing*. Anal. Chem. 72: 5151-5157; Ozawa et al., 2002, *Protein splicing-based reconstitution of split green fluorescent protein for monitoring protein-protein interactions in bacteria: improved sensitivity and reduced screening time*. Anal. Chem. 73: 5866-5874). One of these investigators subsequently reported application of this splicing-based GFP reconstitution system to cultured mammalian cells (Umezawa, 2003, Chem. Rec. 3: 22-28). More recently, Zhang et al., 2004, showed that the helical coil split GFP system of Ghosh et al., 2000, supra, could be used to reconstitute GFP (as well as YFP and CFP) fluorescence when coexpressed in *C. elegans*, and demonstrated the utility of this system in confirming coexpression in vivo (Zhang et al., 2004, *Combinatorial marking of cells and organelles with reconstituted fluorescent proteins*. Cell 119: 137-144).

Although the aforementioned GFP reconstitution systems provide advantages over the use of two spectrally distinct fluorescent protein tags, they are limited by the size of the fragments and correspondingly poor folding characteristics (Ghosh et al., Hu et al., supra), the requirement for a chemical ligation or fused interacting partner polypeptides to force reconstitution (Ghosh et al., 2000, supra; Ozawa et al., 2001, 2002 supra; Zhang et al., 2004, supra), and co-expression or co-refolding to produce detectable folded and fluorescent GFP (Ghosh et al., 2000; Hu et al., 2001, supra). Poor folding characteristics limit the use of these fragments to applications wherein the fragments are simultaneously expressed or simultaneously refolded together. Such fragments are not useful for in vitro assays requiring the long-term stability and solubility of the respective fragments prior to complementation. An example of an application for which such split protein fragments are not useful would be the quantification of polypeptides tagged with one member of the split protein pair, and subsequently detected by the addition of the complementary fragment.

SUMMARY OF THE INVENTION

The invention provides protein subcellular localization assays using split fluorescent protein systems. The assays are conducted in living cells, do not require fixation and washing steps inherent in existing immunostaining and related techniques, and permit rapid, non-invasive, direct visualization of protein localization in living cells. The split fluorescent protein systems used in the practice of the invention generally comprise two or more self-complementing fragments of a fluorescent protein, such as GFP, wherein one or more of the fragments correspond to one or more beta-strand microdomains and are used to "tag" proteins of interest, and a complementary "assay" fragment of the fluorescent protein. Either or both of the fragments may be functionalized with a subcellular targeting sequence enabling it to be expressed in or directed to a particular subcellular compartment (i.e., the nucleus).

In general terms, the invention provides a suite of assays that can be used to detect and differentiate the subcellular location of a protein of interest in living cells, detect proteins that interact in defined subcellular compartments, track the transport of proteins through and out of the cell, identify cell surface expression, monitor and quantify protein secretion, and screen for mediators of localization, transport and/or secretion. These assays may also be used in combination with directed evolution strategies, and scaled to high-throughput screening of protein variants with modified subcellular localization characteristics. The assays are useful to visualize protein localization in, for example, the nucleus, cytoplasm, plasma membrane, endoplasmic reticulum, golgi apparatus, filaments or microtubules such as actin and tubulin filaments, endosomes, peroxisomes and mitochondria.

In one particular embodiment, a test protein is fused to a sixteen amino acid fragment of GFP (β-strand 11, amino acids 215-230), engineered to not perturb fusion protein solubility. When the complementary "assay" GFP fragment (β-strands 1 through 10, amino acids 1-214) is provided, spontaneous association of the GFP fragments results in structural complementation, folding, and concomitant GFP fluorescence. In some embodiments, the assay fragment is functionalized with a subcellular targeting sequence of interest, such that the fragment is localized to the subcellular element of interest, following expression of the fragment in the cell or transfection into the cell. If the test protein is expressed in the cell, or transfected into the cell, and becomes localized to the subcellular element of interest, the fragments self-complement and generate a visually detectable fluorescence. Non-imaging fluorescence detection can be used to determine if the cell has increased fluorescence, thereby indicating that the localization has occurred in the particular compartment to which the complementing fragments have been directed. If desired, imaging fluorescence microscopy is used to visualize the resulting, specifically-localized fluorescent signal, further confirming the presence of the test protein in the subcellular element of interest.

The subcellular localization assays of the invention are simple and only require the use of instruments and methods capable of visualizing fluorescence, such as various well known fluorescence microscopy, confocal microscopy, video microscopy techniques, and the like. The assays require no external reagents, and can be conducted in living cells, enabling real-time imaging in cells with minimal intervention.

A distinct advantage of the present invention over tagging using full-length GFP is the absence of background fluorescence prior to complementation. Only if complementation occurs in a particular compartment to which one or more fragments are localized, does that compartment become fluorescent. It is necessary only to measure the fluorescence of the cell to determine whether the specific localization has occurred, enabling high-throughput screens using flow cytometry, for example, without the need to specifically visualize all the structures in the cell by microscopy. In contrast, when proteins are tagged with full-length GFP, the proteins are fluorescent regardless of localization, and imaging or microscopy must be used to determine the subcellular localization of the tagged protein.

DETAILED DESCRIPTION OF THE INVENTION

Definitions

Figure 1:
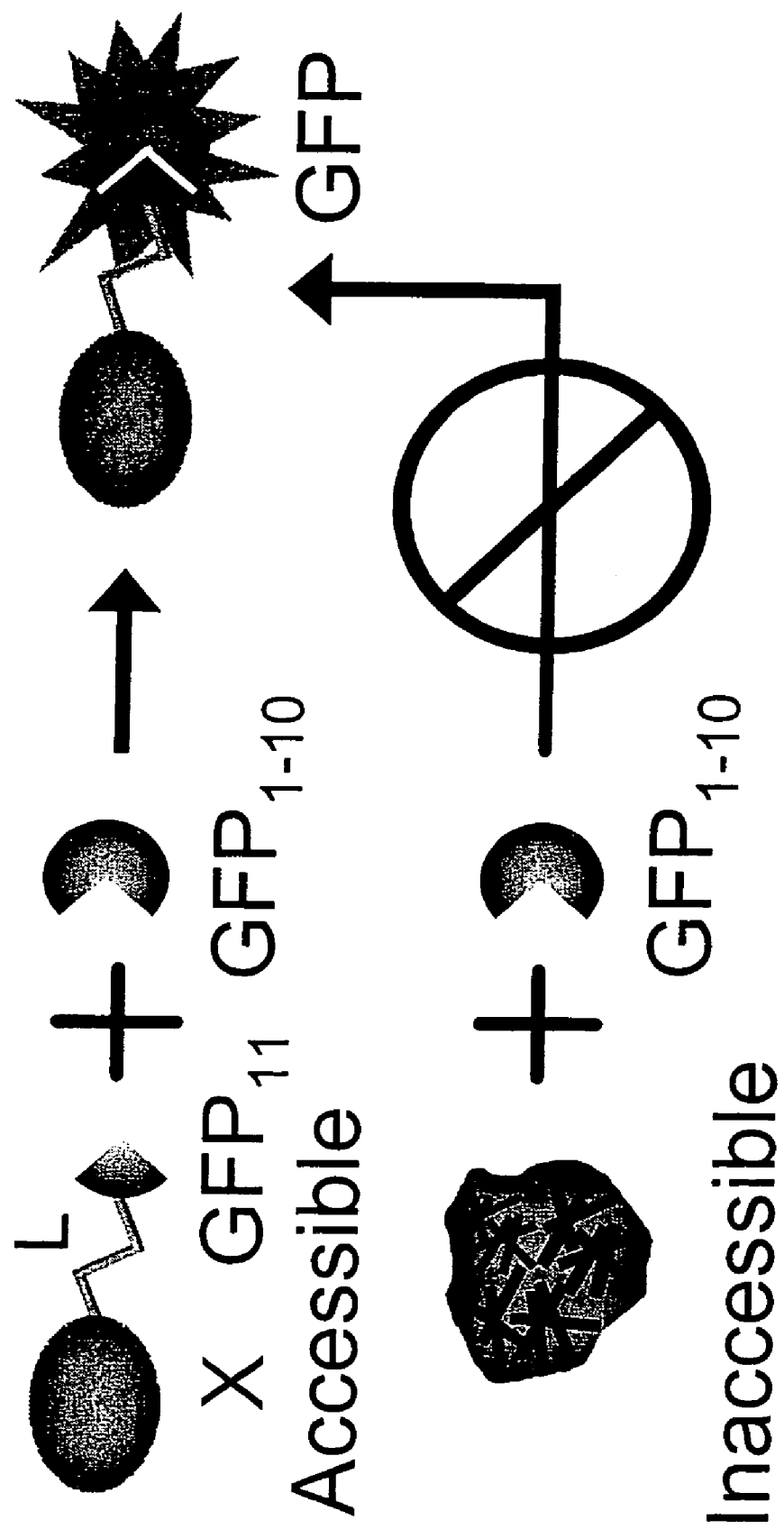
FIG. 1 shows principle of split GFP self-complementation. A protein of interest (X) is fused to a small GFP fragment (β-strand 11, residues 215-230) via a flexible linker (L). The complementary GFP fragment (β-strands 1-10, residues 1-214) is expressed separately. Neither fragment alone is fluorescent. When mixed, the small and large GFP fragments spontaneously associate, resulting in GFP folding and formation of the fluorophore. Processes that make the small GFP tag inaccessible, such as misfolding or aggregation, can prevent complementation.
Figure 2:
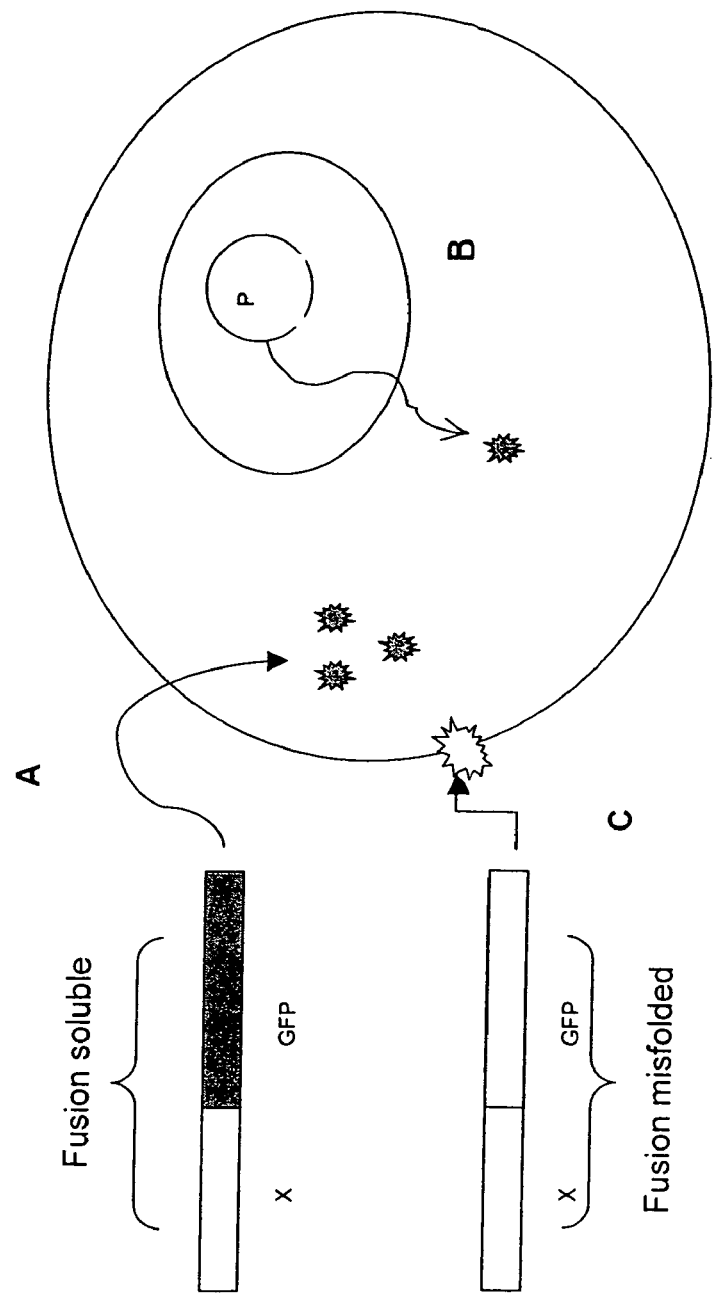
FIG. 2 depicts protein localization using full length GFP. The protein of interest X is expressed in fusion with GFP. The fluorescence of the fusion enables tracking the localization of the protein X in the cell. However, the fusion may not be soluble (C) and will fail to migrate freely in the cell due to aggregation of the fusion protein.

Unless otherwise defined, all terms of art, notations and other scientific terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a substantial difference over what is generally understood in the art. The techniques and procedures described or referenced herein are generally well understood and commonly employed using conventional methodology by those skilled in the art, such as, for example, the widely utilized molecular cloning methodologies described in Sambrook et al., Molecular Cloning: A Laboratory Manual 3rd. edition (2001) Cold Spring Harbor Laboratory Press, Cold Spring Harbor, N.Y. and Current Protocols in Molecular Biology (Ausbel et al., eds., John Wiley & Sons, Inc. 2001. As appropriate, procedures involving the use of commercially available kits and reagents are generally carried out in accordance with manufacturer defined protocols and/or parameters unless otherwise noted.

A "fluorescent protein" as used herein is an *Aequorea Victoria* green fluorescent protein (GFP), structural variants of GFP (i.e., circular permutants, monomeric versions), folding variants of GFP (i.e., more soluble versions, superfolder versions), spectral variants of GFP (i.e., YFP, CFP), and GFP-like fluorescent proteins (i.e., DsRed). The term "GFP-like fluorescent protein" is used to refer to members of the *Anthozoa* fluorescent proteins sharing the 11-beta strand "barrel" structure of GFP, as well as structural, folding and spectral variants thereof. GFP-like proteins all share common structural and functional characteristics, including without limitation, the capacity to form internal chromophores without requiring accessory co-factors, external enzymatic catalysis or substrates, other than molecular oxygen.

A "variant" of a fluorescent protein is derived from a "parent" fluorescent protein and retains the 11 beta-strand barrel structure as well as intrinsic fluorescence, and is meant to include structures with amino acid substitutions, deletions or insertions that may impart new or modified biological properties to the protein (i.e., greater stability, improved solubility, improved folding, shifts in emission or excitation spectra, reduced or eliminated capacity to form multimers, etc) as well as structures having modified N and C termini (i.e., circular permutants).

The term "complementing fragments" or "complementary fragments" when used in reference to a reporter polypeptide refer to fragments of a polypeptide that are individually inactive (i.e., do not express the reporter phenotype), wherein binding of the complementing fragments restores reporter activity. The terms "self-complementing", "self-assembling", and "spontaneously-associating", when used to describe two or more fluorescent (or chromophoric) protein fragments, mean that the fragments are capable of reconstituting into an intact, fluorescent (or chromophoric) protein when the individual fragments are soluble.

The terms "subcellular compartment", "subcellular element", and "subcellular location" are used to refer to various distinguishable parts, components or organelles of a cell, including without limitation, the nucleus, cytoplasm, plasma membrane, endoplasmic reticulum, golgi apparatus, filaments such as actin and tubulin filaments, endosomes, peroxisomes and mitochondria.

The "MMDB Id: 5742 structure" as used herein refers to the GFP structure disclosed by Ormo & Remington, MMDB Id: 5742, in the Molecular Modeling Database (MMDB), PDB Id: 1EMA PDB Authors: M. Ormo & S. J. Remington PDB Deposition: 1 Aug. 1996 PDB Class: Fluorescent Protein PDB Title: Green Fluorescent Protein From *Aequorea Victoria*. The Protein Data Bank (PDB) reference is Id PDB Id: 1 EMA PDB Authors: M. Ormo & S. J. Remington PDB Deposition: 1 Aug. 1996 PDB Class: Fluorescent Protein PDB Title: Green Fluorescent Protein From *Aequorea Victoria*. (see, e.g., Ormo et al. "Crystal structure of the *Aequorea victoria* green fluorescent protein." *Science* Sep. 6, 1996;273 (5280):1392-5; Yang et al, "The molecular structure of green fluorescent protein." *Nat Biotechnol*. Oct. 14, 1996(10):1246-51).

"Root mean square deviation" ("RMSD") refers to the root mean square superposition residual in Angstroms. This number is calculated after optimal superposition of two structures, as the square root of the mean square distances between equivalent C-alpha-atoms.

The term "heterologous" when used with reference to portions of a nucleic acid indicates that the nucleic acid comprises two or more subsequences that are not found in the same relationship to each other in nature. For instance, a nucleic acid is typically recombinantly produced, having two or more sequences from unrelated genes arranged to make a new functional nucleic acid, e.g., a nucleic acid encoding a fluorescent protein from one source and a nucleic acid encoding a peptide sequence from another source. Similarly, a heterologous protein indicates that the protein comprises two or more subsequences that are not found in the same relationship to each other in nature (e.g., a fusion protein).

The terms "identical" or percent "identity", in the context of two or more nucleic acids or polypeptide sequences, refer to two or more sequences or subsequences that are the same or have a specified percentage of amino acid residues or nucleotides that are the same (i.e., about 70% identity, preferably 75%, 80%, 85%, 90%, or 95% identity over a specified region, when compared and aligned for maximum correspondence over a comparison window, or designated region as measured using a BLAST or BLAST 2.0 sequence comparison algorithms with default parameters described below, or by manual alignment and visual inspection. Such sequences are then said to be "substantially identical." This definition also refers to the compliment of a test sequence. Preferably, the identity exists over a region that is at least about 22 amino acids or nucleotides in length, or more preferably over a region that is 30, 40, or 50-100 amino acids or nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, 1981, Adv. Appl. Math. 2:482, by the homology alignment algorithm of Needleman & Wunsch, 1970, J. Mol. Biol. 48:443, by the search for similarity method of Pearson & Lipman, 1988, Proc. Nat'l. Acad. Sci. USA 85:2444, by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Current Protocols in Molecular Biology (Ausubel et al., eds. 1995 supplement)).

A preferred example of algorithm that is suitable for determining percent sequence identity and sequence similarity are the BLAST and BLAST 2.0 algorithms, which are described in Altschul et al., 1977, Nuc. Acids Res. 25:3389-3402 and Altschul et al., 1990, J. Mol. Biol. 215:403-410, respectively. BLAST and BLAST 2.0 are used, typically with the default parameters described herein, to determine percent sequence identity for the nucleic acids and proteins of the invention. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a word length (W) of 11, an expectation (E) of 10, M=5, N=−4 and a comparison of both strands. For amino acid sequences, the BLASTP program uses as defaults a word length of 3, and expectation (E) of 10, and the BLOSUM62 scoring matrix (see Henikoff & Henikoff, *Proc. Natl. Acad. Sci. USA* 89:10915 (1989)) alignments (B) of 50, expectation (E) of 10, M=5, N=−4, and a comparison of both strands.

The BLAST algorithm also performs a statistical analysis of the similarity between two sequences (see, e.g., Karlin & Altschul, 1993, Proc. Nat'l. Acad. Sci. USA 90:5873-5787). One measure of similarity provided by the BLAST algorithm is the smallest sum probability (P(N)), which provides an indication of the probability by which a match between two nucleotide or amino acid sequences would occur by chance.

For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

The term "as determined by maximal correspondence" in the context of referring to a reference SEQ ID NO means that a sequence is maximally aligned with the reference SEQ ID NO over the length of the reference sequence using an algorithm such as BLAST set to the default parameters. Such a determination is easily made by one of skill in the art.

The term "link" as used herein refers to a physical linkage as well as linkage that occurs by virtue of co-existence within a biological particle, e.g., phage, bacteria, yeast or other eukaryotic cell.

"Physical linkage" refers to any method known in the art for functionally connecting two molecules (which are termed "physically linked"), including without limitation, recombinant fusion with or without intervening domains, intein-mediated fusion, non-covalent association, covalent bonding (e.g., disulfide bonding and other covalent bonding), hydrogen bonding; electrostatic bonding; and conformational bonding, e.g., antibody-antigen, and biotin-avidin associations.

"Fused" refers to linkage by covalent bonding.

As used herein, "linker" or "spacer" refers to a molecule or group of molecules that connects two molecules, such as a fluorescent binding ligand and a display protein or nucleic acid, and serves to place the two molecules in a preferred configuration.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

The term "nucleic acid" refers to deoxyribonucleotides or ribonucleotides and polymers thereof in either single- or double-stranded form. Unless specifically limited, the term encompasses nucleic acids containing known analogues of natural nucleotides which have similar binding properties as the reference nucleic acid and are metabolized in a manner similar to naturally occurring nucleotides. Unless otherwise indicated, a particular nucleic acid sequence also implicitly encompasses conservatively modified variants thereof (e.g. degenerate codon substitutions) and complementary sequences and as well as the sequence explicitly indicated. Specifically, degenerate codon substitutions may be achieved by generating sequences in which the third position of one or more selected (or all) codons is substituted with mixed-base and/or deoxyinosine residues (Batzer et al., 1991, Nucleic Acid Res. 19: 5081; Ohtsuka et al., 1985 J. Biol. Chem. 260: 2605-2608; and Cassol et al., 1992; Rossolini et al., 1994, Mol. Cell. Probes 8: 91-98). The term nucleic acid is used interchangeably with gene, cDNA, and mRNA encoded by a gene.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, *Proteins* (1984)).

Macromolecular structures such as polypeptide structures can be described in terms of various levels of organization. For a general discussion of this organization, see, e.g., Alberts et al., *Molecular Biology of the Cell* (3rd ed., 1994) and Cantor and Schimmel, *Biophysical Chemistry Part I: The Conformation of Biological Macromolecules* (1980). "Primary structure" refers to the amino acid sequence of a particular peptide. "Secondary structure" refers to locally ordered, three dimensional structures within a polypeptide. These structures are commonly known as domains. Domains are portions of a polypeptide that form a compact unit of the polypeptide and are typically 25 to approximately 500 amino acids long. Typical domains are made up of sections of lesser organization such as stretches of β-sheet and α-helices. "Tertiary structure" refers to the complete three dimensional structure of a polypeptide monomer. "Quaternary structure" refers to the three dimensional structure formed by the noncovalent association of independent tertiary units. Anisotropic terms are also known as energy terms.

The terms "isolated" and "purified" refer to material which is substantially or essentially free from components which normally accompany it as found in its native state. However, the term "isolated" is not intended refer to the components present in an electrophoretic gel or other separation medium. An isolated component is free from such separation media and in a form ready for use in another application or already in use in the new application/milieu.

Split-Fluorescent and Chromophoric Protein Systems

The subcellular localization assays of the invention utilize split-fluorescent and split-chromophoric protein systems, which are described in co-owned, co-pending U.S. patent application Ser. No. 10/973,693, entitled "SELF-ASSEMBLING SPLIT-FLUORESCENT PROTEIN SYSTEMS", filed Oct. 25, 2004 and hereby incorporated by reference in its entirety.

In the practice of the protein subcellular localization assays of the invention, a number of different split-fluorescent protein systems may be utilized. In general, the split fragments should be capable of being folded and soluble in the cellular environment. In preferred embodiments, the folding/solubility of individual fragments is tested in the cell to be utilized, and optionally evolved, in order to isolate soluble "tag" fragment(s) and soluble "assay" fragment(s). In preferred applications, the tag fragment is a fluorescent protein microdomain corresponding to a single beta-strand (i.e., GFP s11) that is substantially non-perturbing to fused test proteins. The tag fragment (in fusion with a test protein) may be functionalized with pre-defined subcellular localization signals. The use of a single beta-strand provides a tag that is non-perturbing to fused test protein solubility, and minimizes the potential for interference with cellular processing and transport of the fusion. The assay fragment, to which pre-defined subcellular localization signals may be fused, will be structurally complementary to the tag fragment (i.e. GFP s1-10), soluble in the cell used in the assay, and available for complementation with a co-localized tag-test protein fusion protein. The assay fragment is ideally monomeric, and should not spontaneously aggregate or misfold.

A number of specifically engineered tag and assay fragments of a GFP variant are disclosed in U.S. application Ser. No. 10/973,693, supra, the structures of which (DNA and AA sequences) are reproduced herein under the Table of Sequences subsection, infra. Additionally, vectors sequences designed for use with split-GFP systems are also reproduced in the same subsection, infra.

Preferred split-fluorescent protein systems for use in the practice of the assays and methods of the invention are those derived from GFP and GFP-like proteins. GFP-like proteins are an expanding family of homologous, 25-30 kDa polypeptides sharing a conserved 11 beta-strand "barrel" structure. The GFP-like protein family currently comprises some 100 members, cloned from various *Anthozoa* and *Hydrozoa* species, and includes red, yellow and green fluorescent proteins and a variety of non-fluorescent chromoproteins (Verkhusha et al., supra). A wide variety of fluorescent protein labeling assays and kits are commercially available, encompassing a broad spectrum of GFP spectral variants and GFP-like fluorescent proteins, including cyan fluorescent protein, blue fluorescent protein, yellow fluorescent protein, etc., DsRed and other red fluorescent proteins (Zimmer, 2002, Chem. Rev. 102: 759-781; Zhang et al., 2002, Nature Reviews 3: 906-918; Clontech, Palo Alto, CA; Amersham, Piscataway, N.J.). Typically, GFP variants share about 80%, or greater sequence identity with wild type GFP. Color-shift GFP mutants have emission colors blue to yellow-green, increased brightness, and photostability (Tsien, 1998, Annual Review of Biochemistry 67: 509-544).

Additional GFP-based variants having modified excitation and emission spectra (Tsien et al., U.S. Patent Appn. 20020123113A1), enhanced fluorescence intensity and thermal tolerance (Thastrup et al., U.S. Patent Appn. 20020107362A1; Bjorn et al., U.S. Patent Appn. 20020177189A1), and chromophore formation under reduced oxygen levels (Fisher, U.S. Pat. No. 6,414,119) have also been described. GFPs from the Anthozoans *Renilla reniformis* and *Renilla kollikeri* have also been described (Ward et al., U.S. Patent Appn. 20030013849).

One widely utilized red fluorescent protein was isolated from *Discosoma* species of coral, DsRed (Matz et al., 1999, Nat. Biotechnol. 17:969-973), and various DsRed variants (e.g., DsRed1, DsRed2) have been described. DsRed and the other *Anthozoa* fluorescent proteins share only about 26-30% amino acid sequence identity to the wild-type GFP from *Aequorea victoria*, yet all the crucial motifs are conserved, indicating the formation of the 11-stranded beta-barrel structure characteristic of GFP. The crystal structure of DsRed has also been solved, and shows conservation of the 11-stranded beta-barrel structure of GFP MMDB Id: 5742.

A number of mutants of the longer wavelength red fluorescent protein DsRed have also been described. For example, recently described DsRed mutants with emission spectra shifted further to the red may be employed in the practice of the invention (Wiehler et al., 2001, FEBS Letters 487: 384-389; Terskikh et al., 2000, Science 290: 1585-1588; Baird et al., 2000, Proc. Natl. Acad. Sci. USA 97: 11984-11989). Recently, a monomeric variant of DsRed was described (Campell et al., 2002, Proc. Natl. Acad. Sci USA 99: 7877-7882). This variant, termed "mRFP1", matures quickly in comparison to wild type DsRed, which matures over a period of 30 hours), has no residual green fluorescence, and has excitation and emission wavelengths of about 25 nm longer than other DsRed variants.

An increasingly large number of other fluorescent proteins from a number of ocean life forms have recently been described, and the Protein Data Bank currently lists a number of GFP and GFP mutant crystal structures, as well as the crystal structures of various GFP analogs. Related fluorescent proteins with structures inferred to be similar to GFP from corals, sea pens, sea squirts, and sea anemones have been described, and may be used in the generation of the split-fluorescent protein systems of the invention (for reviews, see Zimmer, 2002, Chem. Rev. 102: 759-781; Zhang et al., 2002, Nature Reviews 3: 906-918).

Additionally, fluorescent proteins from *Anemonia majano*, *Zoanthus* sp., *Discosoma striata*, *Discosoma* sp. and *Clavularia* sp. have also been reported (Matz et al., supra). A fluorescent protein cloned from the stony coral species, *Trachyphyllia geoffroyi*, has been reported to emit green, yellow, and red light, and to convert from green light to red light emission upon exposure to UV light (Ando et al., 2002, Proc. Natl. Acad. Sci. USA 99: 12651-12656). Recently described fluorescent proteins from sea anemones include green and orange fluorescent proteins cloned from *Anemonia sulcata* (Wiedenmann et al., 2000, Proc. Natl. Acad. Sci. USA 97: 14091-14096), a naturally enhanced green fluorescent protein cloned from the tentacles of *Heteractis magnifica* (Hongbin et al., 2003, Biochem. Biophys. Res. Commun. 301: 879-885), and a generally non fluorescent purple chromoprotein displaying weak red fluorescence cloned from *Anemonia sulcata*, and a mutant thereof displaying far-red shift emission spectra (595 nm) (Lukyanov et al., 2000, J. Biol. Chem. 275: 25879-25882).

A recently described red fluorescent protein isolated from the sea anenome *Entacmaea quadricolor*, EqFP611, is a far-red, highly fluorescent protein with a unique co-planar and trans chromophore (Wiedenmann et al., 2002, Proc. Natl. Acad. Sci USA 99: 11646-11651). The crystal structure of EqFP611 has been solved, and shows conservation of the 11-stranded beta-barrel structure of GFP MMDB Id: 5742 (Petersen et al., 2003, J. Biol. Chem, Aug. 8, 2003; M307896200).

Still further classes of GFP-like proteins having chromophoric and fluorescent properties have been described. One such group of coral-derived proteins, the pocilloporins, exhibit a broad range of spectral and fluorescent characteristics (Dove and Hoegh-Guldberg, 1999, PCT application WO 00/46233; Dove et al., 2001, Coral Reefs 19: 197-204). Recently, the purification and crystallization of the pocilloporin Rtms5 from the reef-building coral *Montipora efflorescens* has been described (Beddoe et al., 2003, Acta Cryst. D59: 597-599). Rtms5 is deep blue in color, yet is weakly fluorescent. However, it has been reported that Rtms5, as well as other chromoproteins with sequence homology to Rtms5, can be interconverted to a far-red fluorescent protein via single amino acid substitutions (Beddoe et al., 2003, supra; Bulina et al., 2002, BMC Biochem. 3: 7; Lukyanov et al., 2000, supra).

Any fluorescent protein that has a structure with a root mean square deviation of less than 5 angstroms, often less than 3, or 4 angstroms, and preferably less than 2 angstroms from the 11-stranded beta-barrel structure of MMDB Id:5742 may be used in the development of self-complementing fragments. In some cases, fluorescent proteins exist in multimeric form. For example, DsRed is tetrameric (Cotlet et al., 2001, Proc. Natl. Acad. Sci. USA 98: 14398014403). As will be appreciated by those skilled in the art, structural deviation between such multimeric fluorescent proteins and GFP (a monomer) is evaluated on the basis of the monomeric unit of the structure of the fluorescent protein.

As appreciated by one of ordinary skill in the art, such a suitable fluorescent protein or chromoprotein structure can be identified using comparison methodology well known in the art. In identifying the protein, a crucial feature in the alignment and comparison to the MMDB ID:5742 structure is the conservation of the beta-barrel structure (i.e., typically comprising 11 beta strands, but in at least one case, fewer beta strands (see, Wiedenmann et al., 2000, supra), and the topology or connection order of the secondary structural elements (see, e.g., Ormo et al. "Crystal structure of the Aequorea Victoria green fluorescent protein." Yang et al, 1996, Science 273: 5280, 1392-5; Yang et al., 1996 Nat Biotechnol. 10:1246-51). Typically, most of the deviations between a fluorescent protein and the GFP structure are in the length(s) of the connecting strands or linkers between the crucial beta strands (see, for example, the comparison of DsRed and GFP in Yarbrough et al., 2001, Proc Natl Acad Sci USA 98:462-7). In Yarbrough et al., alignment of GFP and DsRed is shown pictorially. From the stereo diagram, it is apparent that the 11 beta-strand barrel is rigorously conserved between the two structures. The c-alpha backbones are aligned to within 1 angstrom RMSD over 169 amino acids, although the sequence identity is only 23% comparing DsRed and GFP.

In comparing structure, the two structures to be compared are aligned using algorithms familiar to those in the art, using for example the CCP4 program suite. COLLABORATIVE COMPUTATIONAL PROJECT, NUMBER 4. 1994. "The CCP4 Suite: Programs for Protein Crystallography". Acta Cryst. D50, 760-763. In using such a program, the user inputs the PDB coordinate files of the two structures to be aligned, and the program generates output coordinates of the atoms of the aligned structures using a rigid body transformation (rotation and translation) to minimize the global differences in position of the atoms in the two structures. The output aligned coordinates for each structure can be visualized separately or as a superposition by readily-available molecular graphics programs such as RASMOL, Sayle and Milner-White, September 1995, Trends in Biochemical Science (TIBS), Vol. 20, No. 9, p. 374.), or Swiss PDB Viewer, Guex, N and Peitsch, M. C., 1996 Swiss-PdbViewer: A Fast and Easy-to-use PDB Viewer for Macintosh and PC. Protein Data Bank Quarterly Newsletter 77, pp. 7.

In considering the RMSD, the RMSD value scales with the extent of the structural alignments and this size is taken into consideration when using the RMSD as a descriptor of overall structural similarity. The issue of scaling of RMSD is typically dealt with by including blocks of amino acids that are aligned within a certain threshold. The longer the unbroken block of aligned sequence that satisfies a specified criterion, the 'better' aligned the structures are. In the DsRed example, 164 of the c-alpha carbons can be aligned to within 1 angstrom of the GFP. Typically, users skilled in the art will select a program that can align the two trial structures based on rigid body transformations, for example, as described in Dali et al., Journal of Molecular Biology 1993, 233, 123-138. The output of the DALI algorithm are blocks of sequence that can be superimposed between two structures using rigid body transformations. Regions with Z-scores at or above a threshold of Z=2 are reported as similar. For each such block, the overall RMSD is reported.

The RMSD of a fluorescent protein for use in the invention is within 5 angstroms for at least 80% of the sequence within the 11 beta strands. Preferably, RMSD is within 2 angstroms for at least 90% of the sequence within the 11 beta strands (the beta strands determined by visual inspection of the two aligned structures graphically drawn as superpositions, and comparison with the aligned blocks reported by DALI program output). As appreciated by one of skill in the art, the linkers between the beta strands can vary considerably, and need not be superimposable between structures.

In preferred embodiments, the fluorescent protein or chromoprotein is a mutated version of the protein or a variant of the protein that has improved folding properties or solubility in comparison to the protein. Often, such proteins can be identified, for example, using methods described in WO0123602 and other methods to select for increased folding.

For example, to obtain a fluorescent protein with increased folding properties, a "bait" or "guest" peptide that decreases the folding yield of the fluorescent protein is linked to the fluorescent protein. The guest peptide can be any peptide that, when inserted, decreases the folding yield of the fluorescent protein. A library of mutated fluorescent proteins is created. The bait peptide is inserted into the fluorescent protein and the degree of fluorescence of the protein is assayed. Those clones exhibit increased fluorescence relative to a fusion protein comprising the bait peptide and parent fluorescent protein are selected (the fluorescent intensity reflects the amount of properly folded fluorescent protein). The guest peptide may be linked to the fluorescent protein at an end, or may be inserted at an internal site.

In a particular embodiment, wild-type and mutant fluorescent proteins and chromoproteins useful in the practice of the invention may be experimentally "evolved" to produce extremely stable, "superfolding" variants. The methods described in co-pending, co-owned U.S. patent application Ser. No. 10/423,688, filed Apr. 24, 2003, hereby incorporated by reference in its entirety, may be employed for the directed evolution of GFP, DsRed, and any number of related fluorescent proteins and chromoproteins. Such superfolding variants may be split into self-complementing fragments, which fragments may be further evolved to modulate solubility characteristics of the fragments alone or when fused to test protein.

Protein Subcellular Localization Assays

The invention provides a suite of assays useful in detecting, differentiating and monitoring the subcellular location of one or more proteins in living cells, detecting proteins that interact in defined subcellular compartments, tracking the transport of proteins through and out of the cell, identifying cell surface expression, monitoring and quantifying protein secretion, and screening for mediators of localization, transport and/or secretion. These assays may also be used in combination with directed evolution strategies, and scaled to high-throughput screening of protein variants with modified subcellular localization characteristics.

In one illustrative embodiment, a test protein or group of test proteins may be screened for localization to a particular subcellular compartment or element, including without limitation the nucleus, cytoplasm, plasma membrane, endoplasmic reticulum, golgi apparatus, filaments such as actin and tubulin filaments, endosomes, peroxisomes and mitochondria. Briefly, a polynucleotide construct encoding a fusion of the test protein and a microdomain of a fluorescent protein (i.e., one or more beta-strands of the fluorescent protein, for example GFP s11) is expressed in cells containing a complementary assay fragment of the fluorescent protein that has been localized to the subcellular compartment of interest. The complementary assay fragment is functionalized to contain a localization signal sequence capable or directing the fragment into the desired subcellular compartment or element. In cases where cytoplasm expression of the test protein is to be assayed, the assay fragment is not functionalized with a particular sequence. The assay fragment may be expressed in the cell or transfected into the cell.

The expressed protein-microdomain tag fusion will only be able to complement with the assay fragment if it is able to gain access to the same subcellular compartment the assay fragment has been directed to. Thus, for example, if test protein X contains an endogenous mitochondrial localization signal, a fusion protein X-GFPs11 would be localized to the mitochondria. An assay fragment localized to the mitochondria will be available to self-complement and generate fluorescence in mitochondria, which can then be visualized using fluorescent microscopy. The assay may be used to identify proteins that localize to a particular subcellular compartment or structure and to identify novel localization signals.

In another illustrative embodiment, a test protein known to localize to the nucleus is generated as a fusion protein with a single beta-strand microdomain of a fluorescent protein (e.g., GFP s11). A complementary "assay" fragment of the fluorescent protein (i.e., GFP s1-10) is generated with a fused nuclear localization tag enabling the assay fragment to be expressed in or otherwise localized to the nucleus. Expressing the test protein-tag fusion in a cell or otherwise providing it to a cell containing the nuclear-localized assay fragment brings the two complementary fragments into proximity resulting in self-complementation and chromophore formation visualized by fluorescence. The assay may be used to screen for agents that interfere with the localization of the test protein to a particular subcellular compartment.

In some applications, the test protein-tag fragment fusion may also be functionalized to be co-localized with the assay fragment, such as where the effect of a drug on localization is being evaluated.

Figure 3:
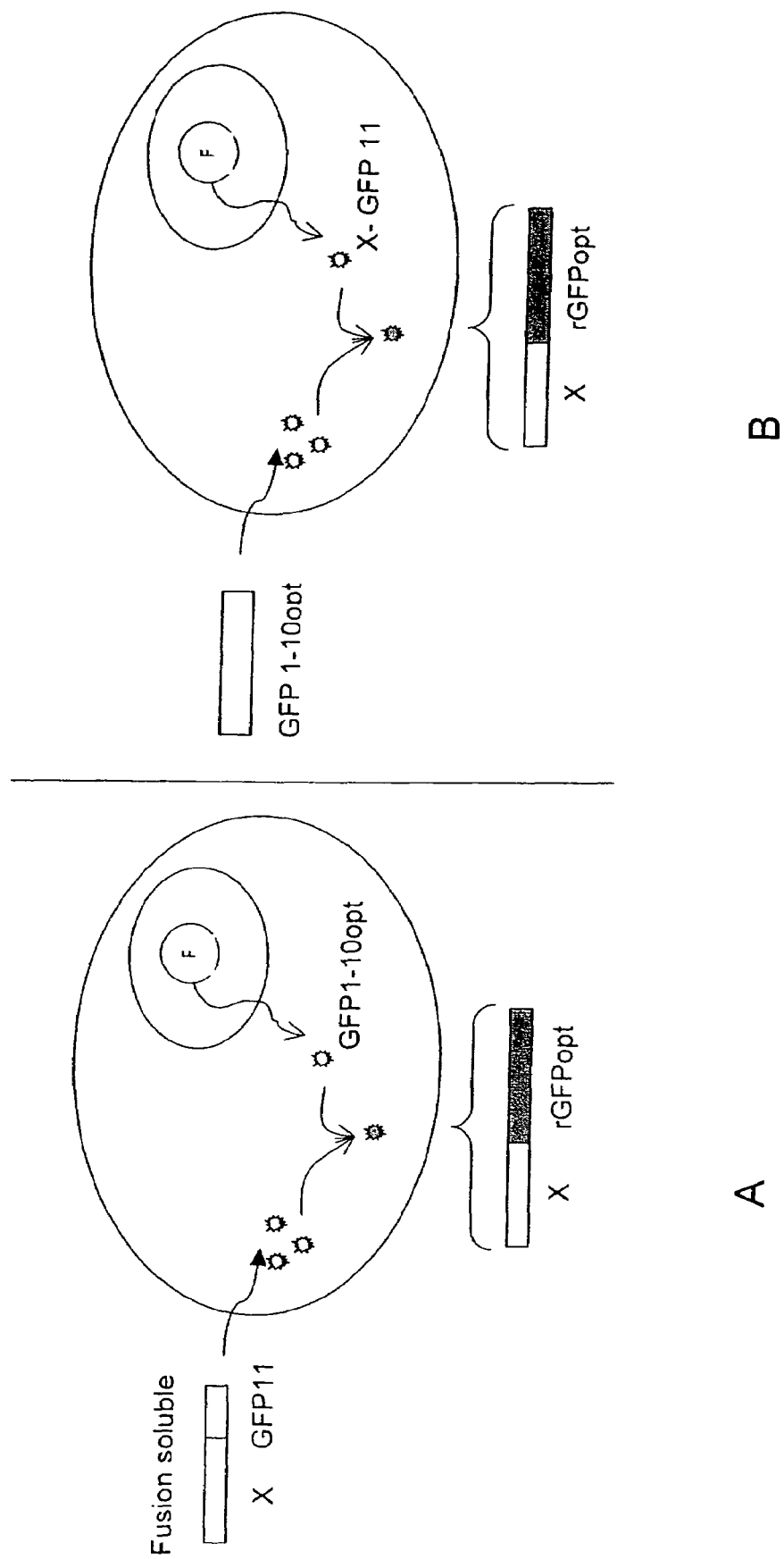
FIG. 3 depicts protein localization studies using a split fluorescent protein, e.g., GFP. The protein of interest X is expressed in fusion with a non-perturbing GFP s11 fragment. In parallel, the large s1-10 GFP fragment is expressed from an independent plasmid. When the transfected GFP s11 tagged protein and the s1-10 GFP fragment meet in the cell, complementation of the two moieties GFP s11+s1-10 induces fluorescence and localization of the protein X in the cell. Unlike fusions with full-length GFP (FIG. 2), GFP s11 has no perturbing effect on the fused protein.

For cytoplasmic localization assays, the test protein is expressed in fusion with a non-perturbing tag fragment, i.e., GFP s11, or may be sandwiched in-frame between microdomains, i.e., between GFP s10 and s11. Optionally, polypeptide linkers may be used in such fusion constructs. The assay fragment, i.e., GFP s1-10 or GFP s1-9, respectively, may be expressed separately or constitutively on a plasmid. When the tagged test protein and assay fragment co-localize in the cell, complementation of the two split GFP fragments occurs, producing a fluorescent signal (FIG. 3). The intensity of the fluorescence is proportional to the number of non aggregated soluble test protein-tag fragment fusion proteins (see U.S. application Ser. No. 10/973,693, supra). In addition to co-expressing the split fragments in the cell, the assay fragment may be transected into the cell using chemical transfection methodologies known in the art.

For detecting subcellular localization to cellular elements other than the cytoplasm, it may be desirable in some applications to have expression of the test protein either precede or lag the expression or transfection of the assay fragment, in order to eliminate non-specific fluorescence resulting from transient localization of either fragment in the course of processing or transport to the element of interest. In some applications, it may be desirable to visualize protein transport through the cell over a time course, and in such applications, the test protein-tag and assay fragments may be co-expressed, from one or more constructs, and optionally under the control of individually inducible promoter systems.

Figure 4:
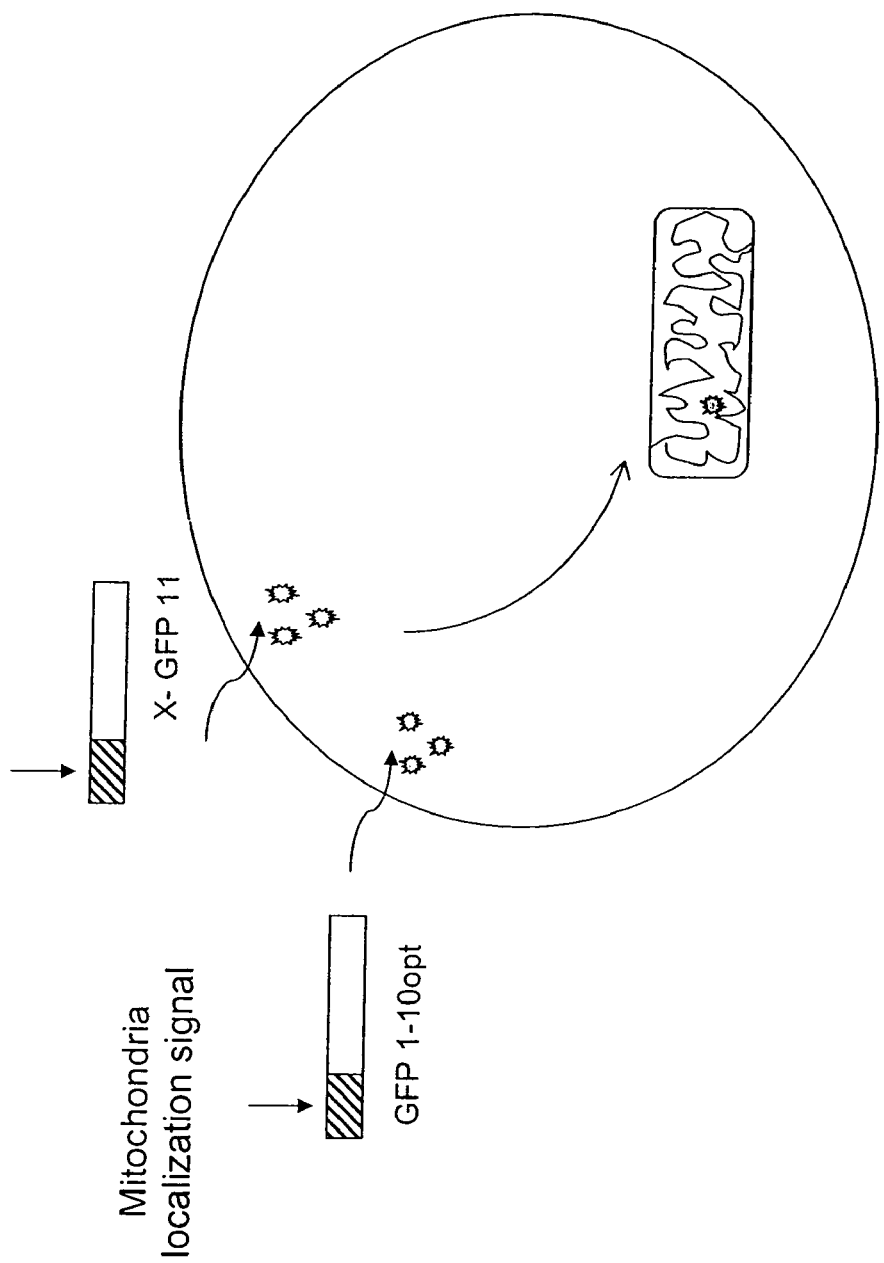
FIG. 4 depicts an assay for screening mitochondrial protein localization. GFP s-10 assay fragment bearing the mitochondrial localization tag is expressed from a constitutive plasmid or transfected into the cell. The presence of the localization signal directs the assay fragment to mitochondria. In parallel, the target proteins (random library) in fusions with a GFP s11 tag fragment are expressed from an inducible expression vector. Localization of the fusion will be targeted to the specialized compartment if the fragment contains a mitochondrial localization signal. Complementation between the pre-localized assay fragment and the expressed fusion X-GFP s11 results in fluorescence in the mitochondria.

Thus, in one embodiment, the functionalized assay fragment is pre-localized to the compartment of interest (e.g., GFP s1-10). This may be achieved by inducing the expression of a polynucleotide encoding the functionalized assay fragment, terminating induction, and then expressing the test protein-tag fragment fusion (e.g., X-GFP s11) through a separately inducible system. Complementation between the pre-localized assay fragment and the expressed test protein-tag fusion results in fluorescence in the specialized cell compartment (see FIG. 4, mitochondrial assay).

In a related embodiment, the cells used to conduct the assay are engineered to contain a plurality of complementary assay fragments, each of which is localized to a different subcellular compartment and designed or selected to produce different color fluorescence upon complementation with the tag. Thus, the color of the fluorescence generated when self-complementation occurs correlates with and localizes to a particular subcellular compartment or structure. Such an assay may be used to screen proteins for their subcellular localization profiles at fixed time points or in real time and to visualize protein trafficking dynamically.

For example, to visualize a test protein's transport and localization from the ER to the Golgi, two assay fragments are used, one functionalized with an ER localization signal and selected to produce cyan fluorescence upon complementation with a test protein-tag fragment fusion present in the ER, and the other functionalized with a Golgi localization signal and selected to produce yellow fluorescence upon complementation with a test protein-tag fragment fusion present in the Golgi. A third assay fragment, for example, may be functionalized with an endosomal localization signal and selected to produce green fluorescence upon complementation with a test protein-tag fragment fusion located in endosomes. A fourth assay fragment selected to produce red fluorescence could be added to the extracellular media, in excess, in order to capture test protein-tag fusions that have been secreted by the cell. Thus, this illustrative combination of fragments and colors could be used to monitor the secretion pathway of a test protein.

Similarly, the secretion assay illustrated above may be used to screen for agents that inhibit or otherwise modulate protein secretion, by adding agent(s) to the cells and observing changes in trafficking and/or secretion yields. Thus, for example, the assay fragment may be targeted to the Golgi to evaluate changes to the secretion pathway of a test protein in the presence of a drug. If a test protein is destined for secretion or export, then complementation between the test protein-tag fragment fusion and the assay fragment will occur in the Golgi, and Golgi vesicles would be visualized as fluorescent. Conversely, the absence of fluorescence provides and indication that the test protein's secretion pathway is altered by the drug.

In a related embodiment, the secretion assay enables the quantification of secreted protein yield, by comparing the fluorescence observed in the extracellular environment (e.g., growth media) with a calibration curve obtained with a soluble control protein and the same "extracellular" assay fragment. In one embodiment of a protein secretion quantitative assay, the test protein is expressed in fusion with the tag fragment (i.e., GFP s11) for a time sufficient to permit secretion of the fusion if secreted. Cells are then pelleted from growth media and an excess of a complementary assay fragment is added to the supernatant. Fluorescence is then measured and used to determine secreted protein quantity.

Secreted proteins identified as above may also be purified by including a modification to one of the split-fragments that can be used as an affinity tag. Typically, this will comprise a sequence of amino acid residues that functionalize the fragment to bind to a substrate that can be isolated using standard purification technologies. In one embodiment, a fragment is functionalized to bind to glass beads, using chemistries well known and commercially available (e.g., Molecular Probes Inc.). Alternatively, the fragment is modified to incorporate histidine residues in order to functionalize the fragment to bind to metal affinity resin beads. In a specific embodiment, a GFP s11 tag fragment, engineered so that all outside pointing residues in the β-strand are replaced with histidine residues, is used (see, U.S. application Ser. No. 10/973,693, supra). This HIS-tag fragment is non-perturbing to test proteins fused therewith, and is capable of detecting soluble protein upon complementation with a GFP s1-10 assay fragment. The HIS-tag fragment can be used to purify secreted proteins from growth media using standard cobalt bead columns, and enables the quantification of soluble and insoluble protein as well as the purification and elution of protein to 95% purity without the need for any another purification tag system.

In addition to screening for protein secretion, cell surface expression of a protein of interest may be assayed. Briefly, test protein-tag fragment fusions are expressed in the cell. The complementary assay fragment my then be added to the surface of the cells (by adding to the growth media). If the test protein-tag fragment fusion is expressed on the cell surface, complementation with the assay fragment occurs at the cell surface, effectively staining the cell surface with the reconstituted fluorescent protein. In such applications, the use of a flexible linker polypeptide, interspersed in-frame between the protein of interest and the tag fragment may provide additional flexibility and accessibility of the tag fragment to its complementary assay fragment. Additionally, it may be desirable to test both orientations of the test protein-tag fragment fusion to take account of potential membrane spanning segments which could obscure the tag fragment in some cases (i.e., x-s11 and s11-s).

Multicolor labeling strategies, as above, may also be combined with fluorescence-activated cell sorting (FACS) in order to conveniently select and isolate cells displaying a particular fluorescence. Thus, for example, if a library of protein random mutants is being screened for any which localize to the nucleus or the mitochondria, multicolored assay fragments functionalized to localize to those organelles will permit FACS differential sorting of mutants localized to one or the other organelle.

Another aspect of the invention relates to assays for timing protein localization. Since reconstituted split GFP s11+s1-10 and GFP s1-10 are visually and intrinsically two distinct entities, it may be possible to broaden the detection mode by using a multicolor version of the GFP s1-10 assay fragment. This strategy would enable differential detection of older and newly synthesized molecules, providing a useful tool for studying mechanisms of assembly of dynamic structures composed of a single family of proteins. One advantage of the split-fluorescent protein systems utilized in the present invention is that once self-complementation occurs, the reconstituted fluorescent protein is very stable, and dissociation of the fragments unlikely under physiological conditions.

In one illustrative embodiment, stable cell lines expressing the target protein X in fusion with the non perturbing short GFP s 1 tag fragment under a constitutive promoter are selected (G418, resistance for example). At desired times, an excess of the complementary assay fragment is be added by chemical transfection methods, such as the Chariot™ reagent (Morris et al., 2001, *A peptide carrier for the delivery of biologically active proteins into mammalian cells.* Nature Biotechnol. 19: 1173-1176), which is capable of directly transfecting a protein into the cytoplasm of a mammalian cell. In order to study transiently the expression of the target protein, the assay fragment may contain a C-terminal destabilized tag, which can be degraded by intracellular tail-specific proteases (see further below). The tag may be adjusted to the cell type for efficient degradation (Triccas, Pinto et al. 2002).

Figure 5:
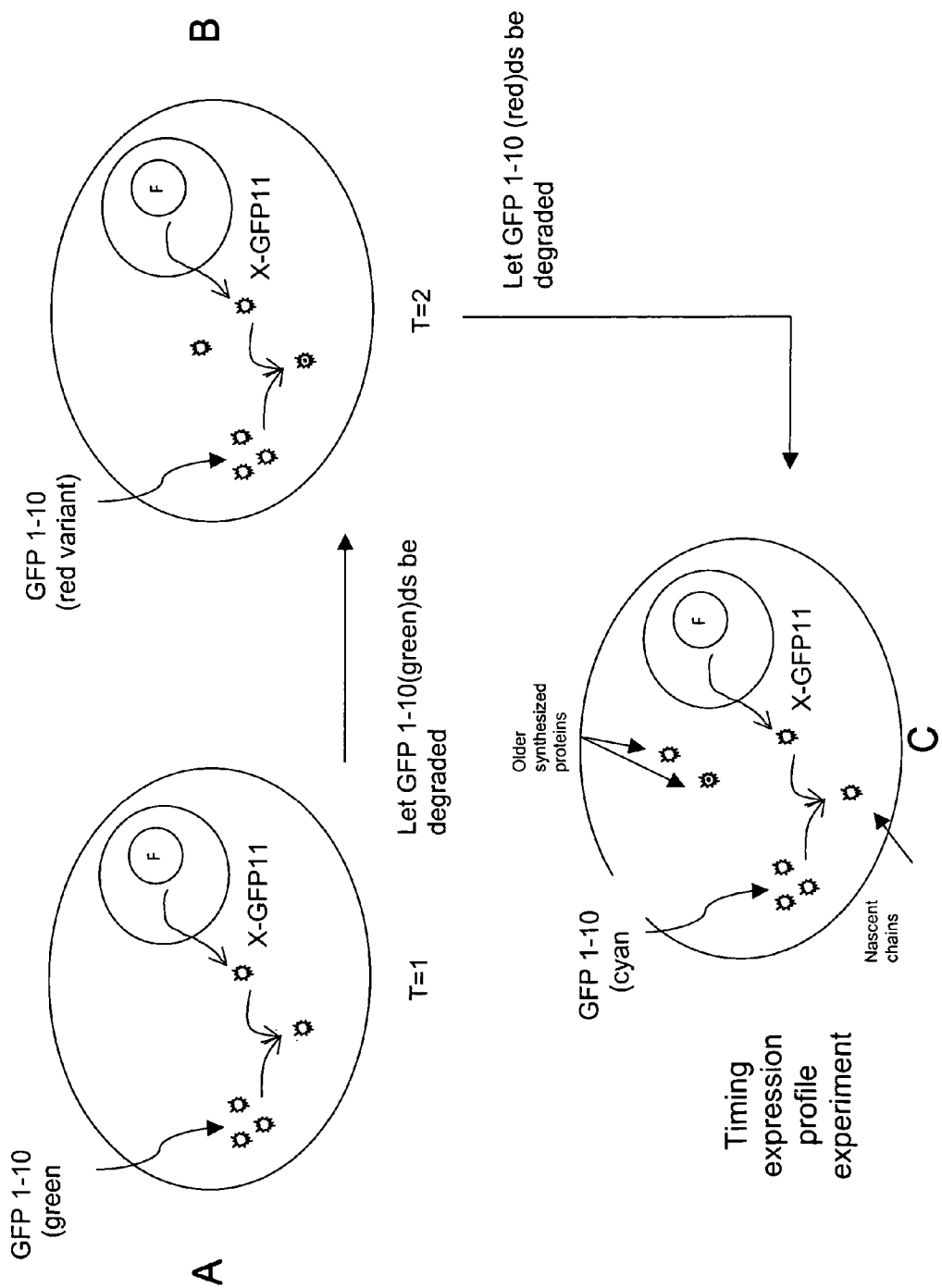
FIG. 5 shows timing the expression of a protein. Cell lines express constitutively the target protein X in fusion with GFP s11. At desired times, an excess of a complementary assay fragment with a C-terminal destabilizing tag is transfected into the cell. The newly synthesized GFP s11 tagged molecules are detected by complementation (FIG. 5, A). Complementation occurs until the GFP s1-10 destabilized fragment is degraded. Once degraded, cells are incubated in growth media for several hours and the procedure is repeated with another destabilized GFP s1-10 assay fragment variant producing a different color upon complementation with GFP s11, for example red (FIG. 5, B). After several assay fragment transfection cycles, superimposition of the different images, taken for each of the excitation/emission wavelengths characteristic of the assay fragments used, would enable localization of the older synthesized protein molecules from the newer synthesized ones (FIG. 5, C).
Figure 6:
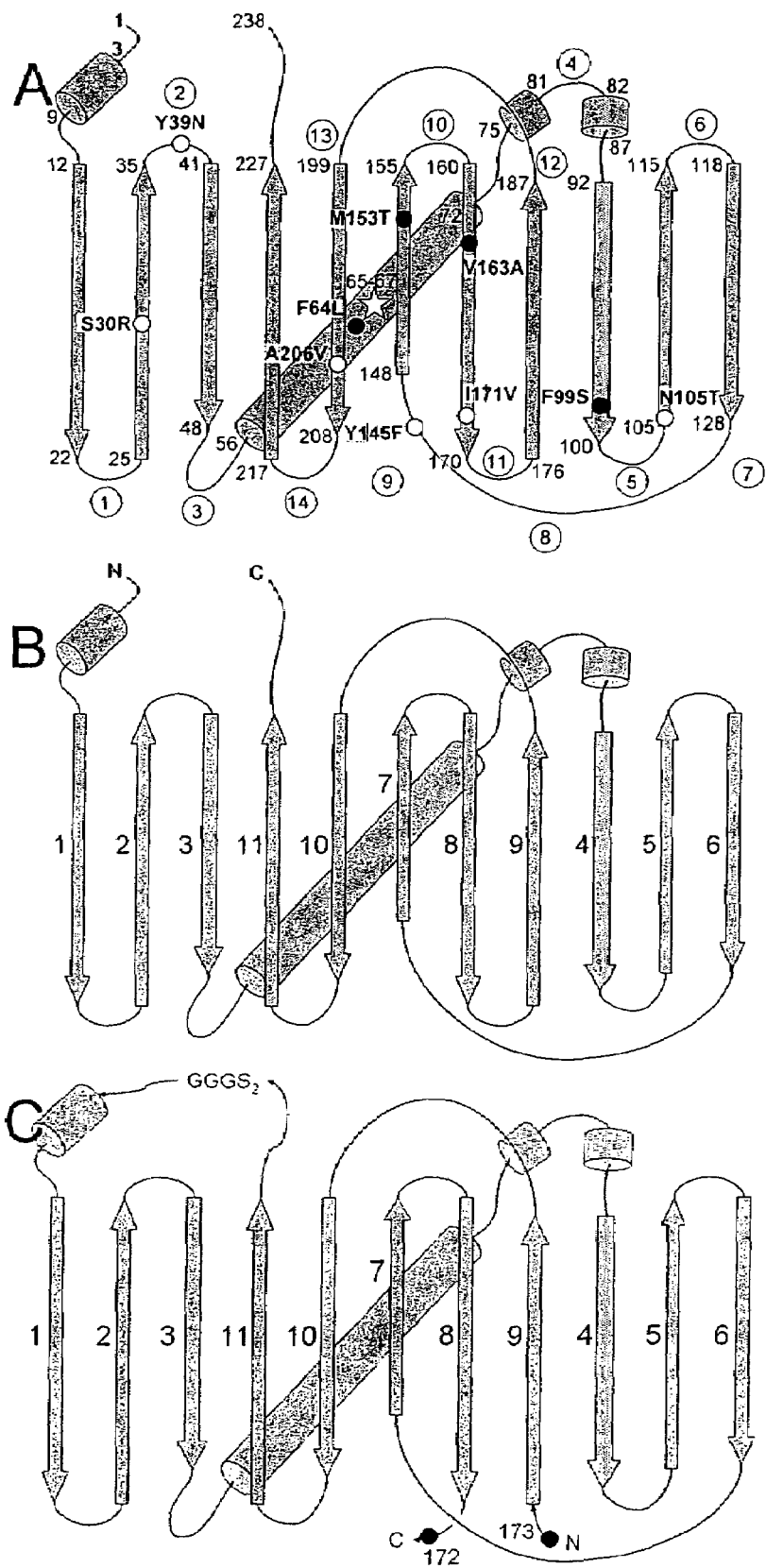
FIG. 6 shows the topological secondary structure diagram of the eleven beta-stranded GFP family members. (A) Strands and numbering of amino acids. Circled number corresponds to index of the turn between strands (and a preferred site for splitting the protein), dark circles are the folding reporter mutations, and white circles are the superfolder GFP mutations. (B) shows numbering convention of the eleven beta strands. (C) shows a circular permutant GFP made by connecting the N and C termini by a short flexible linker and providing a new start codon at amino acid 173, and stop codon after amino acid 172.
Figure 7:
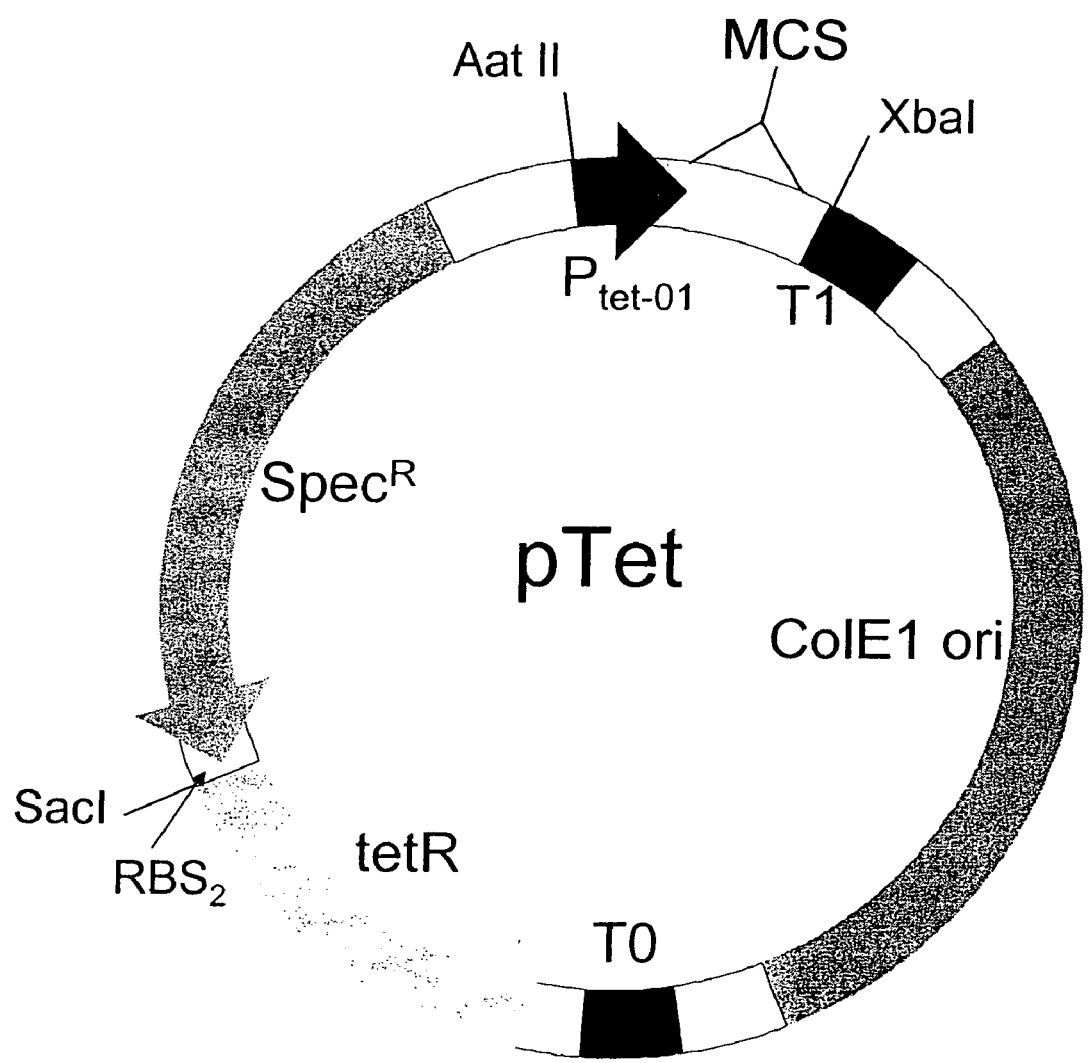
FIG. 7A shows a schematic diagram of the pTET-SpecR plasmid, which is a modified version of the pPROTet.6×HN vector available from Clontech (Palo Alto, Calif.). The chloramphenicol resistance gene was replaced by the spectinomycin resistance marker under the control of the kanamycin promoter of the pPROlar resistance marker (pPROlar plasmid from Clontech, Palo Alto, Calif.). On the same cistron is encoded the tetracycline repressor upstream of the T0 transcription termination sequence. The amount of translated repressor is regulated by a weak Shine-Delgarno sequence downstream of SacI.
FIG. 7B shows the different elements of the engineered pTET-SpecR plasmid [SEQ ID NO: 22]. Regions of interest are boxed: Box 1=v1 cloning cassette for expressing genes under tet promoter, flanked by NcoI CCATGG, and KpnI GGTACC. Box 2=T0 transcription terminator for the SpecR-tetR cistron; Box 3=tetR repressor gene; Box 4=RBS controlling tetR translation; Box 5=spectinomycin (specR) gene; Cyan=kanamycin promoter element from PROLAR vector (Clontech, Palo Alto, Calif.).

The newly synthesized GFP s11 tagged molecules would be detected by complementation between the short and large split subunits (FIG. 5, A). The complementation would proceed until the GFP s1-10 destabilized assay fragment is degraded. Once degraded, the cells are incubated in growth media for several hours and the procedure repeated with another destabilized GFP s1-10 variant producing a different color upon complementation with GFP s11, for example red (FIG. 5, B). After several assay fragment transfection cycles, superimposition of the different images, taken for each of the excitation/emission wavelengths characteristic of the assay fragments used, would enable localization of the older synthesized protein molecules from the newer synthesized ones (FIG. 5, C).

Various approaches may be used to limit the lifetime of the individual fluorescent protein fragments used in such subcellular timing assays. Briefly, various polypeptide tags may be applied to the test protein-tag fragment in order to limit the time that an uncomplemented fragment survives. Such tags are known, and include, for example, the ubiquination sequence, the PEST sequence and mouse ornithine carboxylase. These polypeptide tags destabilize the proteins to which that are attached, marking them for degradation. Once split-fluorescent protein fragments self-complement, the reconstituted fluorescent protein is stable. Thus, such tags may be used to quickly eliminate any un-complemented fragments, from the cell entirely or in certain components of the cell (i.e., cytoplasm).

Yet another aspect of the invention relates to assays used to screen for agents that modulate protein localization. In one embodiment, a test protein-tag fragment fusion is transfected into a cell, and an agent (drug) of interest is added to the cell. Complementary assay fragments are functionalized to be directed to different subcellular compartments and result in different fluorescent colors upon complementation. The assay fragments are expressed in or transfected into the cell following the addition of the drug. Confocal microscopy is then used to examine the localization of the test protein. Indeed after complementation, the changes in fluorescence emission after addition of the drug may also be visualized, so that changes in protein localization, due to the drug, may be observed. The absence of fluorescence provides an indication of a direct effect on the protein's transport. Similarly, the modulating influence of any environmental stimulus, exogenous protein, or gene may be studied using this assay.

In yet another aspect of the invention, assays are provided for measuring the activation or inhibition of target protein expression in response to an effector, such as a transcriptional or translational activator or inhibitor. In one illustrative embodiment, the protein of interest X is cloned in fusion with a fluorescent protein tag fragment (i.e., X-GFP s11), and is expressed constitutively in a cell. The assay fragment (i.e., GFP s1-10) is subsequently transfected into the cell, and the fluorescence upon complementation defined as baseline fluorescence without the effector (Fo). After stabilization of the fluorescence level, indicating the saturation of GFP s1-10 molecules by GFP s11 tagged protein, the effector would be added to the cell or expressed in the cell. A pool of GFP s1-10 assay fragments is transfected again into the cell and the fluorescence level measured again (F1). The ratio F1/Fo provides a measure of the activation or repression of a gene under specific conditions. The assay fragment may be functionalized with localization signals or not, depending upon the nature of the interrogation.

The invention may also enable the detection of a protein that interacts with another protein in a particular subcellular compartment. Thus, for example a protein of interest is expressed in fusion with a GFP s11 tag such that it becomes localized to the subcellular compartment of interest. The localization may be a result of the protein's native localization signals or the result of a localization functionality engineered into the tag fusion. Test proteins are expressed in fusion with a GFP s10 tag. The complementary assay fragment (in this case, GFP s1-9), functionalized to transport to the subcellular compartment of interest, is expressed in the cell or transfected into the cell. Fluorescence detected in the cellular compartment of interest indicates that the three fragments co-localized and self-complemented, thus indicating that the test protein localizes to the compartment of interest and binds to the protein of interest in that compartment. This system may be used to study the effects of drugs on the interaction of proteins in particular cellular compartments. Similarly, the system may be employed to screen libraries of mutant proteins X which display modulated interactions with protein Y in a distinct cellular compartment, and to screen for protein X variants capable of overcoming the interfering influence of a drug on the interaction between X and Y in a distinct cellular compartment.

The invention also provides an improved method for screening to cellular co-expression as a means of identifying uncharacterized promoters. Briefly, an exemplary assay comprises two proteins tagged respectively with GFP s10 and GFP s11 under the control of (1) a known promoter and (2) a random or uncharacterized promoter. The complementary assay fragment GFP s1-9 is functionalized to be directed to the desired subcellular location in the cell. If simultaneous expression occurs, then complementation of the GFP s10 and s11 fusions with the GFP s1-9 assay fragment will produce fluorescence. The level of expression of the unknown promoter may be determined by complementation of the GFP s11 tagged protein with GFP s1-10. The unknown promoter might be a library of promoters for which expression levels are screened in response to a particular stimulus.

Subcellular Localization Signals

Various subcellular localization signal sequences or tags are known and/or commercially available. These tags are used to direct split-fluorescent protein fragments to particular cellular components or outside of the cell. Mammalian localization sequences capable of targeting proteins to the nucleus, cytoplasm, plasma membrane, endoplasmic reticulum, golgi apparatus, actin and tubulin filaments, endosomes, peroxisomes and mitochondria are known.

Subcellular localization signals require a specific orientation, N or C terminal to the protein to which the signal is attached. For example, the nuclear localization signal (NLS) of the simian virus 40 large T-antigen must be oriented at the C-terminus. Thus, where the test protein-tag fragment is to be localized to the nucleus, a fusion <test protein-tag fragment-NLS> or <tag fragment-test protein-NLS> (or constructs encoding tem) may be used, the former orientation being generally preferred to avoid potential perturbation of test protein by the tag fragment. Similarly, if the assay fragment is to be directed to the nucleus, the fusion <assay fragment-NLS> (or a construct encoding it) may be used.

Table 1, infra, provides example mammalian cell nuclear, Golgi, mitochondrial, and ER localization tags, together with orientation information. Table 2, infra, provides the signal sequences themselves along with the polynucleotide coding sequences. Other localization signal sequences are known and may be employed in the practice of the assays of the invention.

TABLE 1

MAMMALIAN SUBCELLULOCALIZATION TAGS

| Localization tag | Localization signal | Position in fusion protein | Function | References |
|---|---|---|---|---|
| Nucleus | nuclear localization signal (NLS) of the simian virus 40 large T-antigen | C-terminus | For localized expression in the nucleus of mammalian cells. It allows the | (Kalderon, Roberts et al. 1984) (Lanford, Kanda et al. 1986) |

TABLE 1-continued

MAMMALIAN SUBCELLULOCALIZATION TAGS

| Localization tag | Localization signal | Position in fusion protein | Function | References |
|---|---|---|---|---|
| Golgi | sequence encoding the N-terminal 81 amino acids of human beta 1,4-galactosyltransferase (GT) | N-terminus | visualization of the nucleus in living and fixed cells using fluorescence microscopy. This region of human beta 1,4-GT contains the membrane-anchoring signal peptide that targets the fusion protein to the trans-medial region of the Golgi apparatus | (Watzele and Berger 1990) (Yamaguchi and Fukuda 1995; Llopis, McCaffery et al. 1998) |
| Mitochondria | mitochondrial targeting sequence derived from the precursor of subunit VIII of human cytochrome C oxidase | N-terminus | designed for labeling of mitochondria | (Rizzuto, Nakase et al. 1989; Rizzuto, Brini et al. 1995) |
| Endoplasmic reticulum (ER) | (ER) targeting sequence of calreticulin | N-terminus | for labeling of the endoplasmic reticulum in mammalian cells | (Munro and Pelham 1987; Fliegel, Burns et al. 1989) |

TABLE 2

SUBCELLULAR LOCALIZATION SIGNAL SEQUENCES

| Localization | Sequence |
|---|---|
| Nucleus<br>nuclear localization signal (NLS) of the simian virus 40 large T-antigen | C-terminus (28 AA)<br>S K K E E K G R S K K E E K G R S K K E E K G R I H R I * [SEQ ID NO:37]<br>TCCAAAAAGAAGAGAAAGGTAGATCCAAAAAAGAAGAGAAAGGTAGATCCAAAAAAGAAGAGAAAGGTAGG<br>ATCCACCGGATCTAG [SEQ ID NO:38] |
| Golgi<br>the N-terminal 81 amino acids of human beta 1,4-galactosyltrans-ferase (GT) | N-terminus (89 AA)<br>M R L R E P L L S G S A A M P G A S L Q R A C R L L V A V C A L H L G V<br>T L V Y Y L A G R D L S R L P Q L V G V S T P L Q G G S N S A A A I G Q<br>S S G E L R T G G A K D P P V A T [SEQ ID NO:39]<br>ATGAGGCTTCGGGAGCCGCTCCTGAGCGGCAGCGCCGCGATGCCAGGCGCGTCCCTACAGCGGGCCTGCCGC<br>CTGCTCGTGGCCGTCTGCGCTCTGCACCTTGGCGTCACCCTCGTTTACTACCTGGCTGGCCGCGACCTGAGC<br>CGCCTGCCCCAACTGGTCGGAGTCTCCACACCGCTGCAGGGCGGCTCGAACAGTGCCGCCGCCATCGGGCAG<br>TCCTCCGGGGAGCTCCGGACCGGAGGGGCCAAGGATCCACCGGTCGCCACC [SEQ ID NO:40] |
| Mitochondria targeting sequence derived from the precursor of sub-unit VIII of human cytochrome C oxidase | N-terminus (36 AA)<br>M S V L T P L L L R G L T G S A R R L P V P R A K I H S L G D P P V A T<br>[SEQ ID NO:41]<br>ATGTCCGTCCTGACGCCGCTGCTGCTGCGGGGCTTGACAGGCTCGGCCCGGCGGCTCCCAGTGCCGCGCGCC<br>AAGATCCATTCGTTGGGGGATCCACCGGTCGCCACC [SEQ ID NO:42] |
| ER targeting sequence of calreticulin | N-terminus (18 AA)<br>M L L S V P L L L G L L G L A V A V [SEQ ID NO:43]<br>ATGCTGCTATCCGTGCCGTTGCTGCTCGGCCTCCTCGGCCTGGCCGTCGCCGTG<br>[SEQ ID NO:44] |

Applications in Prokaryotic and Eukaryotic Cell Culture

The split-fluorescent and split-chromophoric protein systems of the invention may be applied to assays in virtually any cell type, including without limitation bacterial cells (e.g., *E. coli*) and mammalian cells (e.g., CHO cells). One limitation is that expression of GFP and GFP-like proteins is compromised in highly acidic environments (i.e., pH=4.0 or less). Likewise, complementation rates are generally inefficient under conditions of pH of 6.5 or lower (see U.S. application Ser. No. 10/973,693, supra).

As will be appreciated by those skilled in the art, the vectors used to express the tag and/or assay fragments must be compatible with the host cell in which the vectors are to reside. Similarly, various promoter systems are available and should be selected for compatibility with cell type, strain, etc. Codon optimization techniques may be employed to adapt sequences for use in other cells, as is well known.

When using mammalian cells for the subcellular localization assays of the invention, an alternative to codon optimization is the use of chemical transfection reagents, such as the recently described "chariot" system (Morris et al., 2001, *A peptide carrier for the delivery of biologically active proteins into mammalian cells*. Nature Biotechnol. 19: 1173-1176). The Chariot™ reagent may be used to directly transfect a protein into the cytoplasm of a mammalian cell. Thus, this approach would be useful for an in vivo protein detection assay, wherein the assay fragment may be introduced into the cell, either before or after expression of the genetically-encoded test protein-tag fragment fusion by the cell.

Applications to Determining Membrane Protein Topology

The split-fluorescent and split-chromophoric protein systems of the invention may be applied to assays to dissect membrane protein topology. For example, GFP s11 can be fused to a test membrane protein (N-terminus, C-terminus, or internally), and the fusion protein is transiently expressed within a cell or cellular compartment. The protein becomes embedded or anchored within a target membrane leaf. For illustration, assume that the membrane has an internally-facing side (to the interior of the cell compartment) and an external side (to the exterior of the cell compartment). Next, the assay fragment GFP 1-10 is expressed or added using a protein transfection reagent, and is directed to the interior side of the membrane using a localization tag, for example. If the test protein is oriented with the tag directed to the interior of the membrane, complementation occurs and is detected by fluorescence. If the tag is oriented to the exterior of the compartment, complementation does not occur. Simultaneous detection of more than one possible localization event can be performed. A yellow GFP 1-10 containing T203Y can be directed to the outside of the membrane, using localization tags, for example; while the conventional "green" GFP 1-10 containing T203 is directed to the interior, using localization tags. Yellow fluorescence indicates the tag is localized to the exterior, while green indicates localization to the interior. The order of expression of the tagged protein and assay fragments can be reversed if desired to increase signal-to-noise and improve specificity. For example, the assay fragment(s) could be transiently-expressed, followed by the tagged test protein.

Methods for Isolating Improved Protein Variants

The protein subcellular localization assays described supra may be used in combination with directed evolution strategies aimed at isolating protein variants having improved or otherwise modulated characteristics relative to a parent, un-evolved protein. For example, as described infra, variants of a protein X which are able to interact with and bind with protein Y in a distinct cellular compartment may be screened and isolated using a three fragment split-fluorescent protein system.

Any method known in the art for generating a library of mutated protein variants may be used to generate candidate test proteins which may be expressed as fusions with a tag fragment. The target protein or polypeptide is usually mutated by mutating the nucleic acid. Techniques for mutagenizing are well known in the art. These include, but are not limited to, such techniques as error-prone PCR, chemical mutagenesis, and cassette mutagenesis. Alternatively, mutator strains of host cells may be employed to add mutational frequency (Greener and Callahan (1995) *Strategies in Mol. Biol.* 7: 32). For example, error-prone PCR (see, e.g., Ausubel, supra) uses low-fidelity polymerization conditions to introduce a low level of point mutations randomly over a long sequence. Other mutagenesis methods include, for example, recombination (WO98/42727); oligonucleotide-directed mutagenesis (see, e.g., the review in Smith, *Ann. Rev. Genet.* 19: 423-462 (1985); Botstein and Shortle, *Science* 229: 1193-1201 (1985); Carter, *Biochem. J.* 237: 1-7 (1986); Kunkel, "The efficiency of oligonucleotide directed mutagenesis" in Nucleic acids & Molecular Biology, Eckstein and Lilley, eds., Springer Verlag, Berlin (1987), *Methods in Enzymol.* 100: 468-500 (1983), and *Methods in Enzymol.* 154: 329-350 (1987)); phosphothioate-modified DNA mutagenesis (Taylor et al., *Nucl. Acids Res.* 13: 8749-8764 (1985); Taylor et al., *Nucl. Acids Res.* 13: 8765-8787 (1985); Nakamaye and Eckstein, *Nucl. Acids Res.* 14: 9679-9698 (1986); Sayers et al., *Nucl. Acids Res.* 16:791-802 (1988); Sayers et al., *Nucl. Acids Res.* 16: 803-814 (1988)), mutagenesis using uracil-containing templates (Kunkel, *Proc. Nat'l. Acad. Sci. USA* 82: 488-492 (1985) and Kunkel et al., Methods in Enzymol. 154:367-382, 1987); mutagenesis using gapped duplex DNA (Kramer et al., *Nucl. Acids Res.* 12: 9441-9456 (1984); Kramer and Fritz, *Methods in Enzymol.* 154:350-367 (1987); Kramer et al., *Nucl. Acids Res.* 16: 7207 (1988)); and Fritz et al., *Nucl. Acids Res.* 16: 6987-6999 (1988)). Additional methods include point mismatch repair (Kramer et al., *Cell* 38: 879-887 (1984)), mutagenesis using repair-deficient host strains (Carter et al., *Nucl. Acids Res.* 13: 4431-4443 (1985); Carter, *Methods in Enzymol.* 154: 382-403 (1987)), deletion mutagenesis (Eghtedarzadeh and Henikoff, *Nucl. Acids Res.* 14: 5115 (1986)), restriction-selection and restriction-purification (Wells et al., *Phil. Trans. R. Soc. Lond. A* 317: 415-423 (1986)), mutagenesis by total gene synthesis (Nambiar et al., Science 223: 1299-1301 (1984); Sakamar and Khorana, *Nucl. Acids Res.* 14: 6361-6372 (1988); Wells et al., *Gene* 34:315-323 (1985); and Grundstrom et al., *Nucl. Acids Res.* 13: 3305-3316 (1985). Kits for mutagenesis are commercially available (e.g., Bio-Rad, Amersham International). More recent approaches include codon-based mutagenesis, in which entire codons are replaced, thereby increasing the diversity of mutants generated, as exemplified by the RID method described in Murakami et al., 2002, Nature Biotechnology, 20: 76-81.

In a bacterial expression system, clones expressing variants may be rapidly screened for solubility using the above-described in vivo or in vitro assays. Thus, in an in vivo embodiment, a library of clones is generated in *E. coli*, each clone harboring an expressible construct encoding an individual variant protein fused to the tag fragment, under the control of a first and independently inducible promoter. The cells may concurrently harbor an expressible construct encoding the complementary assay fragment, under the control of a second and separately inducible promoter, or the assay fragment polypeptide itself (introduced by protein transfection methods such as described in Morris et al., 2001, supra)

In one in vivo embodiment, cells are induced to express the tag fragment-protein variant fusion, followed by expression of the complementary fragment in the cells. In most preferred embodiments, expression of the fusion is repressed or shut-down for a time sufficient to permit aggregation of insoluble fusion (i.e., 1 h), followed by the induction of complementary fragment expression. In a variation of this approach, the cells only harbor the fusion constructs, preferably under the control of an inducible/repressible promoter, and the complementary fragment is introduced by protein transfection methodologies.

Various in vitro embodiments are possible. Generally, these comprise the expression of the variant protein-tag fragment fusions in, for example, *E. coli*, followed by cell lysis and reaction with the complementary assay fragment polypeptide. See U.S. application Ser. No. 10/973,693, supra.

Kits

Another aspect of the invention provides kits useful in conducting the various assays described, supra. Kits of the invention may facilitate the use of split-fluorescent and split-chromophoric systems of the invention for the subcellular localization assays described herein. Various materials and reagents for practicing the assays of the invention may be provided. Kits may contain reagents including, without limitation, polypeptides or polynucleotides, cell transformation and transfection reagents, reagents and materials for purifying polypeptides, protein denaturing and refolding reagents, as well as other solutions or buffers useful in carrying out the assays and other methods of the invention. Kits may also include control samples, materials useful in calibrating the assays of the invention, and containers, tubes, microtiter plates and the like in which assay reactions may be conducted. Kits may be packaged in containers, which may comprise compartments for receiving the contents of the kits, instructions for conducting the assays, etc.

For example, kits may provide one or more split-fluorescent protein fragments of the invention, one or more polynucleotide vectors encoding one or more fluorescent protein fragments, cell strains suitable for propagating the vector, cells pretransformed or stably transfected with constructs encoding one or more fluorescent protein fragments, and reagents for purification of expressed fusion proteins.

EXAMPLES

Example 1

Complementation of Split GFP in the Cytoplasm—Detection of Cytoplasmic Proteins

Expression of Fluorescent Tagged Proteins:

A test protein, in this example, the soluble *p. aerophilum* sulfite reductase gamma subunit (SR), is tagged with a single beta-strand microdomain of a fluorescence protein, i.e. GFP s11 opt, and a complementary "assay" fragment of this fluorescent protein (i.e. GFP s1-10) is expressed from N-6HIS pET 28 vectors (Novagen, Madison, Wis.). 500 ml cultures of BL21 (DE3) expressing each construct are grown to OD600 ~0.5, and induced with 1 mM IPTG for 4 h at 37° C. The culture pellets are resuspended in 10 ml TNG and sonicated. The soluble fractions are loaded onto Talon resin purification beads (TALON, Clontech, Palo Alto, Calif.). After two washes with excess TNG buffer and one wash in TNG supplemented with 5 mM imidazole, the protein is eluted with 150 mM imidazole in TNG buffer. Proteins are dialyzed in PBS buffer (mMNaCl, mMKCl, mMNa2HPO4, mMKH2PO4), quantified using Bradford Biorad protein-assay reagent (Biorad, Hercules, Calif.) and diluted to a final concentration of 1 mg/ml.

Protein Transfection in Mammalian Cells:

Hela cells (Human epithelial cells from a fatal cervical carcinoma transformed by human papillomavirus 18 (HPV18) (Henrietta Lacks, 1951) are grown at 37° C. in a 5% $CO_2$ humidified atmosphere in Dulbecco's modified Eagle's medium (DMEM) containing 4.5 g/l glucose supplemented with 10% fetal bovine serum and 10 mM glutamine.

In a 4-well Lab-Tek chamber slide (Nalge Nunc. Int., Rochester, N.Y.), $5.0 \times 10^4$ cells per well are seeded in 500 µl of complete growth medium. The cells are incubated at 37° C. in a humidified atmosphere containing 5% $CO_2$ until the cells were 50-70% confluent.

The purified proteins are diluted into 20 µl of PBS for each transfection reaction to obtain 1 µg of protein per transfection reaction. In separate tubes, one for each transfection reaction, 2 µl of Chariot reagent (Ative Motif, Carlsbad, Calif.) is diluted into 20 µl of sterile $H_2O$. The 20 µl macromolecule dilution is mixed with the 20 µl Chariot dilution, and then incubated at room temperature for 30 minutes to allow the Chariot-macromolecule complex to form.

In the chamber slide, the medium is aspirated from the cells to be transfected, and cells are washed with PBS. The cells are then overlaid with the 40 µl Chariot-macromolecule complex and 160 µl of serum-free media added to the overlay to achieve the Final Transfection volume of 200 µl for each well.

The transfection reaction is incubated at 37° C. in a humidified atmosphere containing 5% $CO_2$ for one hour. 400 µl of complete growth medium is added to the cells to continue incubation at 37° C. in a humidified atmosphere containing 5% $CO_2$ for 1 to 2 hours. The media is removed from the chamber and cells are washed with PBS before mounting with a cover slip. Cells may be alternatively fixed with 2% formaldehyde to cross link proteins, washed 5 min in 25 mM glycine in PBS to neutralize the formaldehyde, and then membranes are permeabilized in 0.2% Triton X-100 in PBS.

Complementation assays in the cell requires two successive transfections, in one example the s11 tagged protein is transfected first followed by the complementary fragment GFP 1-10; in a second example the 1-10 fragment is transfected first, followed by SR-s11 protein. Complementation of the two fragments results in fluorescence in the cytoplasm or the subcellular targeted compartment.

Example 2

Complementation of Split GFP in Specialized Compartments

Cloning of Localization Sequences in Fusion with SR-s11 and GFP1-10

If both fragments contains a sequence that targets the gene of interest in a specialized compartment, then the two tagged split-GFP fragments will be targeted to this particular location and will be able to complement in the compartment.

Various subcellular localization signal sequences or tags are known and/or commercially available. These tags are used to direct split-fluorescent protein fragments to particular cellular components or outside of the cell. Mammalian localization sequences capable of targeting proteins to the nucleus, cytoplasm, plasma membrane, endoplasmic reticulum, golgi apparatus, actin and tubulin filaments, endosomes, peroxisomes and mitochondria are known.

Detailed protocols for localization in the nucleus, mitochondria and endoplasmic reticulum follow.

Localization in mitochondria: The mitochondrial targeting sequence derived from the precursor of subunit VIII of human cytochrome C oxidase was cloned in N-terminus of both SR-s11 and GFP 1-10 OPT to yield the constructs MTS-SR-s11 or MTS-1-10opt. The mitochondrial targeting sequence (MTS) was amplified from the commercially available plasmid pECFP_Mito vector (BD Biosciences Clontech, Palo Alto, Calif.) using specific primers

```
                                              [SEQ ID NO:45]
TAAGAAGGAGATATAATGGTCCTGACGCCGCTGCTGCTG
and

[SEQ ID NO:46]
CAGCAGCGGCGTCAGGACCATTATATCTCCTTCTTAAAG
``` which tails the MTS sequence to a pET translation initiation sequence, and downstream primers

```
                                              [SEQ ID NO:47]
GGCGACCGGTGGGTCCCCCAACGAATGGATCTT
and

[SEQ ID NO:48]
CTATATCATATGAGAACCGCCACCGGTGGCGACCGGTGGGTC
``` that include a GGGS [SEQ ID NO: 49] linker between the MTS sequence and the protein of interest (SR-s11 fusion or 1-10opt). The entire cassette was digested with SphI/NdeI and cloned in the receiving vector pET SR-s11_C6his vector. The MTS-GFP1-10 construct was created by cloning 1-10opt in place of SR-s11 protein, using NdeI/KpnI restriction sites. MTS tagged proteins are expressed and transfected as described supra in Example 1.

For nucleotide and amino acid sequences of MTS-SR-s11, see SEQ ID NOS: 53-54.

For nucleotide and amino acid sequences of MTS-GFP 1-10opt, see SEQ ID NOS: 61-62).

Nuclear localization: The nuclear localization signal (NLS) of the simian virus 40 large T-antigen was cloned in C-terminus of both target proteins expressed in fusion with the s11 tag at the N-terminus, and GFP1-10opt. The NLS sequence was amplified from the commercially available vector pDsRed_Nuc (BD Biosciences Clontech, Palo Alto, Calif.) using forward specific primers

```
                                              [SEQ ID NO:50]
GGCGGTTCTTCCAAAAAGAAGAGAAAGGTAGA
and

[SEQ ID NO:51]
GATATAGGATCCGGTGGCGGTTCTTCCAAAAAGAA,
``` which include a BamHI cloning site, and reverse specific primers

```
                                              [SEQ ID NO:52]
TTAGATCCGGTGTATCCTACCTTTCTCTTCTTT
and

[SEQ ID NO:53]
CTATATCTCGAGTTAGATCCGGTGTATCCTACC,
``` which silence BamHI in the NLS sequence and include an XhoI site at the 3' end. The entire cassette is digested BamHII/XhoI and cloned in the receiving vector pET N6his-L-s11-SR- vector (see SEQ ID NOS: 65-66). The GFP1-10 NLS construct was created by cloning 1-10opt in place of s11-SR protein, using SpeI/BamHI restriction sites. NLS tagged proteins are expressed and transfected as described supra in Example 1.

For nucleotide and amino acid sequences of s11-SR-NLS, see SEQ ID NOS:67-68.

For nucleotide and amino acid sequences of GFP 1-10opt-NLS, see SEQ ID NOS: 69-70.

Endoplasmic reticulum (ER) localization: The ER localization of proteins require the fusion at the N-terminus of 18 amino-acid targeting sequence of calreticulin (CAL) and retention of the protein in the ER compartment requires the presence of a KDEL [SEQ ID NO: 54] peptide at the C-terminus of the target protein.

The CAL sequence is cloned into the N-terminus of SR-s11 and GFP1-10opt, and includes the KDEL [SEQ ID NO: 54] linker in C-terminus of both proteins.

The targeting sequence of calreticulin (CAL) is amplified from the commercially available plasmid pDsRed ER vector (BD Biosciences Clontech, Palo Alto, Calif.) using specific primers

```
                                              [SEQ ID NO:55]
TAAGAAGGAGATATAATGCTGCTATCCGTGCCGTTGC
and

[SEQ ID NO:56]
CGGCACGGATAGCAGCATTATATCTCCTTCTTAAAG
``` which tails the CAL sequence to a pET translation initiation sequence, and downstream primers that include a GGGS [SEQ ID NO: 49] linker fater the CAL sequence and include a NdeI restriction site. The entire cassette is digested SphI/NdeI and cloned in the receiving vector pET SR-s11_C6his vector.

The retention sequence KDEL [SEQ ID NO: 54] was created using forward specific primers

```
                                              [SEQ ID NO:57]
GATATAGGTACCGGTGGCGGTTCTCACCACCACCACCAC
and

[SEQ ID NO:58]
TCTCACCACCACCACCACCACGGTGGCGGTTCT
``` which include a linker between the target protein and the C-terminal HIS-tag, and reverse specific primers

```
                                              [SEQ ID NO:59]
CAGCTCGTCCTTAGAACCGCCACCGTGGTGGTG
and

[SEQ ID NO:60]
CTATATCTCGAGTTACAGCTCGTCCTTAGAACCGCCACC,
``` which include the C-terminal KDEL [SEQ ID NO: 54] sequence. The 6HIS-KDEL stuffer was cloned using KpnI/XhoI restriction sites in the N-terminal CAL pET vector. The CAL-GFP1-10-KDEL construct was created by cloning 1-10opt in place of SR-s11 protein, using NdeI/KpnI restriction sites.

For nucleotide and amino acid sequences of CAL-SR-s11-KDEL, see SEQ ID NOS:71-72.

For nucleotide and amino acid sequences of CAL-GFP1-10opt-KDEL, see SEQ ID NOS:73-74.

Golgi

Primers specific from the Golgi localization sequence (GLS) are used to amplify the 81 amino-acid sequence from the commercially available vector pDsRed_Golgi (Clontech). The GLS cassette is cloned in N-terminus of SR-s11 and GFP 1-10opt similarly as it was done for the N-terminal *Mitochondria* localization sequence (See supra).

All publications, patents, and patent applications cited in this specification are herein incorporated by reference as if each individual publication or patent application were specifically and individually indicated to be incorporated by reference.

The present invention is not to be limited in scope by the embodiments disclosed herein, which are intended as single illustrations of individual aspects of the invention, and any which are functionally equivalent are within the scope of the invention. Various modifications to the models and methods of the invention, in addition to those described herein, will become apparent to those skilled in the art from the foregoing description and teachings, and are similarly intended to fall within the scope of the invention. Such modifications or other embodiments can be practiced without departing from the true scope and spirit of the invention.

LITERATURE CITED

Adams, S. R., R. E. Campbell, et al. (2002). "New biarsenical ligands and tetracysteine motifs for protein labeling in vitro and in vivo: synthesis and biological applications." *J Am Chem Soc* 124(21): 6063-76.

Arai, M., K. Maki, et al. (2003). "Testing the relationship between foldability and the early folding events of dihydrofolate reductase from *Escherichia coli*." *J Mol Biol* 328(1): 273-88.

Armstrong, N., A. de Lencastre, et al. (1999). "A new protein folding screen: application to the ligand binding domains of a glutamate and kainate receptor and to lysozyme and carbonic anhydrase." *Protein Sci* 8(7): 1475-83.

Baird, G. S., D. A. Zacharias, et al. (1999). "Circular permutation and receptor insertion within green fluorescent proteins." *Proc Natl Acad Sci USA* 96(20): 11241-6.

Baneyx, F. (1999). "Recombinant protein expression in *Escherichia coli*." *Curr Opin Biotechnol* 10(5): 411-21.

Bertens, P., W. Heijne, et al. (2003). "Studies on the C-terminus of the Cowpea mosaic virus movement protein." *Arch Virol* 148(2): 265-79.

Crameri, A., E. A. Whitehorn, et al. (1996). "Improved green fluorescent protein by molecular evolution using DNA shuffling." *Nat Biotechnol* 14(3): 315-9.

Fahnert, B., H. Lilie, et al. (2004). "Inclusion bodies: formation and utilisation." *Adv Biochem Eng Biotechnol* 89: 93-142.

Fitz-Gibbon, S., A. J. Choi, et al. (1997). "A fosmid-based genomic map and identification of 474 genes of the hyperthermophilic archaeon *Pyrobaculum aerophilum*." *Extremophiles* 1(1): 36-51.

Fox, J. D., R. B. Kapust, et al. (2001). "Single amino acid substitutions on the surface of *Escherichia coli* maltose-binding protein can have a profound impact on the solubility of fusion proteins." *Protein Sci* 10(3): 622-30.

Gegg, C. V., K. E. Bowers, et al. (1997). "Probing minimal independent folding units in dihydrofolate reductase by molecular dissection." *Protein Sci* 6(9): 1885-92.

Gerstein, M., A. Edwards, et al. (2003). "Structural genomics: current progress." *Science* 299(5613): 1663.

Goh, C. S., N. Lan, et al. (2004). "Mining the structural genomics pipeline: identification of protein properties that affect high-throughput experimental analysis." *J Mol Biol* 336(1): 115-30.

Iwakura, M. and T. Nakamura (1998). "Effects of the length of a glycine linker connecting the N— and C-termini of a circularly permuted dihydrofolate reductase." *Protein Eng* 11(8): 707-13.

Iwakura, M., T. Nakamura, et al. (2000). "Systematic circular permutation of an entire protein reveals essential folding elements." *Nat Struct Biol* 7(7): 580-5.

Jappelli, R., A. Luzzago, et al. (1992). "Loop mutations can cause a substantial conformational change in the carboxy terminus of the ferritin protein." *J Mol Biol* 227(2): 532-43.

Kelemen, B. R., T. A. Klink, et al. (1999). "Hypersensitive substrate for ribonucleases." *Nucleic Acids Res* 27(18): 3696-701.

Kim, J. S. and R. T. Raines (1993). "Ribonuclease S-peptide as a carrier in fusion proteins." *Protein Sci* 2(3): 348-56.

Knaust, R. K. and P. Nordlund (2001). "Screening for soluble expression of recombinant proteins in a 96-well format." *Anal Biochem* 297(1): 79-85.

Lopes Ferreira, N. and J. H. Alix (2002). "The DnaK chaperone is necessary for alpha-complementation of beta-galactosidase in *Escherichia coli*." *J Bacteriol* 184(24): 7047-54.

Lutz, R. and H. Bujard (1997). "Independent and tight regulation of transcriptional units in *Escherichia coli* via the LacR/O, the TetR/O and AraC/I1-I2 regulatory elements." *Nucleic Acids Res* 25(6): 1203-10.

Makrides, S. C. (1996). "Strategies for achieving high-level expression of genes in *Escherichia coli*." *Microbiol Rev* 60(3): 512-38.

Nixon, A. E. and S. J. Benkovic (2000). "Improvement in the efficiency of formyl transfer of a GAR transformylase hybrid enzyme." *Protein Eng* 13(5): 323-7.

Ormö, M., A. B. Cubitt, et al. (1996). "Crystal structure of the *Aequorea victoria* green fluorescent protein." *Science* 273 (5280): 1392-1395.

Patterson, G. H., S. M. Knobel, et al. (1997). "Use of the green fluorescent protein and its mutants in quantitative fluorescence microscopy." *Biophys J* 73(5): 2782-90.

Pelletier, J. N., K. M. Arndt, et al. (1999). "An in vivo library-versus-library selection of optimized protein-protein interactions." *Nat Biotechnol* 17(7): 683-90.

Pelletier, J. N., F. X. Campbell-Valois, et al. (1998). "Oligomerization domain-directed reassembly of active dihydrofolate reductase from rationally designed fragments." *Proc Natl Acad Sci USA* 95(21): 12141-6.

Richards, F. M. and P. J. Vithayathil (1959). "The preparation of subtilisn-modified ribonuclease and the separation of the peptide and protein components." *J Biol Chem* 234(6): 1459-65.

Rossi, F. M., B. T. Blakely, et al. (2000). "Monitoring protein-protein interactions in live mammalian cells by beta-galactosidase complementation." *Methods Enzymol* 328: 231-51.

Smith, V. F. and C. R. Matthews (2001). "Testing the role of chain connectivity on the stability and structure of dihydrofolate reductase from *E. coli*: fragment complementation and circular permutation reveal stable, alternatively folded forms." *Protein Sci* 10(1): 116-28.

Stemmer, W. P. (1994). "DNA shuffling by random fragmentation and reassembly: in vitro recombination for molecular evolution." *Proc Natl Acad Sci USA* 91(22): 10747-51.

Studier, F. W., A. H. Rosenberg, et al. (1990). "Use of T7 RNA polymerase to direct expression of cloned genes." *Methods Enzymol* 185: 60-89.

Tal, M., A. Silberstein, et al. (1985). "Why does Coomassie Brilliant Blue R interact differently with different proteins? A partial answer." *J Biol Chem* 260(18): 9976-80.

Terwilliger, T. C. (2004). "Structures and technology for biologists." *Nat Struct Mol Biol* 11(4): 296-7.

Tsien, R. Y. (1998). "The green fluorescent protein." *Annu Rev Biochem* 67: 509-44.

Ullmann, A., F. Jacob, et al. (1967). "Characterization by in vitro complementation of a peptide corresponding to an operator-proximal segment of the beta-galactosidase structural gene of *Escherichia coli.*" *J Mol Biol* 24(2): 339-43.

Waldo, G. S. (2003). "Genetic screens and directed evolution for protein solubility." *Curr Opin Chem Biol* 7(1): 33-8.

Waldo, G. S. (2003). "Improving protein folding efficiency by directed evolution using the GFP folding reporter." *Methods Mol Biol* 230: 343-59.

Waldo, G. S., B. M. Standish, et al. (1999). "Rapid protein-folding assay using green fluorescent protein." *Nature Biotechnology* 17(#7): 691-695.

Wehrman, T., B. Kleaveland, et al. (2002). "Protein-protein interactions monitored in mammalian cells via complementation of beta-lactamase enzyme fragments." *Proc Natl Acad Sci USA* 99(6): 3469-74.

Welply, J. K., A. V. Fowler, et al. (1981). "beta-Galactosidase alpha-complementation. Effect of single amino acid substitutions." *J Biol Chem* 256(13): 6811-6.

Wigley, W. C., R. D. Stidham, et al. (2001). "Protein solubility and folding monitored in vivo by structural complementation of a genetic marker protein." *Nat Biotechnol* 19(2): 131-6.

Worrall, D. M. and N. H. Goss (1989). "The formation of biologically active beta-galactosidase inclusion bodies in *Escherichia coli.*" *Aust J Biotechnol* 3(1): 28-32.

Yang, F., L. G. Moss, et al. (1996). "The molecular structure of green fluorescent protein." *Nature Biotechnology* 14(10): 1246-1251.

Yokoyama, S. (2003). "Protein expression systems for structural genomics and proteomics." *Curr Opin Chem Biol* 7(1): 3943.

Feilmeier, B. J., G. Iseminger, et al. (2000). "Green fluorescent protein functions as a reporter for protein localization in *Escherichia coli.*" *J Bacteriol* 182(14): 4068-76.

Fliegel, L., K. Burns, et al. (1989). "Molecular cloning of the high affinity calcium-binding protein (calreticulin) of skeletal muscle sarcoplasmic reticulum." *J Biol Chem* 264(36): 21522-8.

Gaietta, G., T. J. Deerinck, et al. (2002). "Multicolor and electron microscopic imaging of connexin trafficking." *Science* 296(5567): 503-7.

Hanson, D. A. and S. F. Ziegler (2004). "Fusion of green fluorescent protein to the C-terminus of granulysin alters its intracellular localization in comparison to the native molecule." *J Negat Results Biomed* 3(1): 2.

Kalderon, D., B. L. Roberts, et al. (1984). "A short amino acid sequence able to specify nuclear location." *Cell* 39(3 Pt 2): 499-509.

Lanford, R. E., P. Kanda, et al. (1986). "Induction of nuclear transport with a synthetic peptide homologous to the SV40 T antigen transport signal." *Cell* 46(4): 575-82.

Liopis, J., J. M. McCaffery, et al. (1998). "Measurement of cytosolic, mitochondrial, and Golgi pH in single living cells with green fluorescent proteins." *Proc Natl Acad Sci USA* 95(12): 6803-8.

Morris, M. C., J. Depollier, et al. (2001). "A peptide carrier for the delivery of biologically active proteins into mammalian cells." *Nat Biotechnol* 19(12): 1173-6.

Munro, S. and H. R. Pelham (1987). "A C-terminal signal prevents secretion of luminal ER proteins." *Cell* 48(5): 899-907.

Ozawa, T., Y. Sako, et al. (2003). "A genetic approach to identifying mitochondrial proteins." *Nat Biotechnol* 21(3): 287-93.

Rizzuto, R., M. Brini, et al. (1995). "Chimeric green fluorescent protein as a tool for visualizing subcellular organelles in living cells." *Curr Biol* 5(6): 635-42.

Rizzuto, R., H. Nakase, et al. (1989). "A gene specifying subunit VIII of human cytochrome c oxidase is localized to chromosome 11 and is expressed in both muscle and non-muscle tissues." *J Biol Chem* 264(18): 10595-600.

Southward, C. M. and M. G. Surette (2002). "The dynamic microbe: green fluorescent protein brings bacteria to light." *Mol Microbiol* 45(5): 1191-6.

Tanudji, M., S. Hevi, et al. (2002). "Improperly folded green fluorescent protein is secreted via a non-classical pathway." *J Cell Sci* 115(Pt 19): 3849-57.

Triccas, J. A., R. Pinto, et al. (2002). "Destabilized green fluorescent protein for monitoring transient changes in mycobacterial gene expression." *Res Microbiol* 153(6): 379-83.

Watzele, G. and E. G. Berger (1990). "Near identity of HeLa cell galactosyltransferase with the human placental enzyme." *Nucleic Acids Res* 18(23): 7174.

Yamaguchi, N. and M. N. Fukuda (1995). "Golgi retention mechanism of beta-1,4-galactosyltransferase. Membrane-spanning domain-dependent homodimerization and association with alpha- and beta-tubulins." *J Biol Chem* 270 (20): 12170-6.

Zhang, S., C. Ma, et al. (2004). "Combinatorial marking of cells and organelles with reconstituted fluorescent proteins." *Cell* 119(1): 137-44.

TABLE OF SEQUENCES

SEQ ID NO:1
GFP superfolder 1-10 nucleotide sequence:
ATGAGCAAAGGAGAAGAACTTTTCACTGGAGTTGTCCCAATTCTTGTTGAATTAGATGGT

GATGTTAATGGGCACAAATTTTCTGTCAGAGGAGAGGGTGAAGGTGATGCTACAAACGGA

AAACTCACCCTTAAATTTATTTGCACTACTGGAAAACTACCTGTTCCATGGCCAACACTT

GTCACTACTCTGACCTATGGTGTTCAATGCTTTTCCCGTTATCCGGATCACATGAAACGG

CATGACTTTTTCAAGAGTGCCATGCCCGAAGGTTATGTACAGGAACGCACTATATCTTTC

AAAGATGACGGGACCTACAAGACGCGTGCTGAAGTCAAGTTTGAAGGTGATACCCTTGTT

AATCGTATCGAGTTAAAAGGTATTGATTTTAAAGAAGATGGAAACATTCTCGGACACAAA

CTCGAGTACAACTTTAACTCACACAATGTATACATCACGGCAGACAAACAAAAGAATGGA

TABLE OF SEQUENCES

ATCAAAGCTAACTTCAAAATTCGCCACAACGTTGAAGATGGTTCCGTTCAACTAGCAGAC

CATTATCAACAAAATACTCCAATTGGCGATGGCCCTGTCCTTTTACCAGACAACCATTAC

CTGTCGACACAATCTGTCCTTTCGAAAGATCCCAACGAAAAGCTAA

SEQ ID NO:2
GFP super folder 1-10 amino acid sequence:
MSKGEELFTGVVPILVELDGDVNGHKFSVRGEGEGDATNGKLTLKFICTTGKLPVPWPTL

VTTLTYGVQCFSRYPDHMKRHDFFKSAMPEGYVQERTISFKDDGTYKTRAEVKFEGDTLV

NRIELKGIDFKEDGNILGHKLEYNFNSHNVYITADKQKNGIKANFKIRHNVEDGSVQLAD

HYQQNTPIGDGPVLLPDNHYLSTQSVLSKDPNEK

SEQ ID NO:3
GFP 1-10 OPT nucleotide sequence:
ATGAGCAAAGGAGAAGAACTTTTCACTGGAGTTGTCCCAATTCTTGTTGAATTAGATGGT

GATGTTAATGGGCACAAATTTTCTGTCAGAGGAGAGGGTGAAGGTGATGCTACAATCGGA

AAACTCACCCTTAAATTTATTTGCACTACTGGAAAACTACCTGTTCCATGGCCAACACTT

GTCACTACTCTGACCTATGGTGTTCAATGCTTTTCCCGTTATCCGGATCACATGAAAAGG

CATGACTTTTTCAAGAGTGCCATGCCCGAAGGTTATGTACAGGAACGCACTATATCTTTC

AAAGATGACGGGAAATACAAGACGCGTGCTGTAGTCAAGTTTGAAGGTGATACCCTTGTT

AATCGTATCGAGTTAAAGGGTACTGATTTTAAAGAAGATGGAAACATTCTCGGACACAAA

CTCGAGTACAACTTTAACTCACACAATGTATACATCACGGCAGACAAACAAAAGAATGGA

ATCAAAGCTAACTTCACAGTTCGCCACAACGTTGAAGATGGTTCCGTTCAACTAGCAGAC

CATTATCAACAAAATACTCCAATTGGCGATGGCCCTGTCCTTTTACCAGACAACCATTAC

CTGTCGACACAAACTGTCCTTTCGAAAGATCCCAACGAAAAGGGTACCTAA

SEQ ID NO:4
GFP 1-10 OPT amino acid sequence:
(additional mutations vs. superfolder: N39I, T105K, E111V,
I128T, K166T, I167V, S205T)
MSKGEELFTGVVPILVELDGDVNGHKFSVRGEGEGDATIGKLTLKFICTTGKLPVPWPTL

VTTLTYGVQCFSRYPDHMKRHDFFKSAMPEGYVQERTISFKDDGKYKTRAVVKFEGDTLV

NRIELKGTDFKEDGNILGHKLEYNFNSHNVYITADKQKNGIKANFTVRHNVEDGSVQLAD

HYQQNTPIGDGPVLLPDNHYLSTQTVLSKDPNEKGT

SEQ ID NO:5
GFP 1-10 A4 nucleotide sequence:
ATGAGCAAAGGAGAAGAACTTTTCACTGGAGTTGTCCCAATTCTTGTTGAATTAGATGGA

GATGTTAATGGGCACAAATTTTCTGTCAGAGGAGAGGGTGAAGGTGATGCTACAAACGGA

AAACTCACCCTTAAATTCATTTGCACTACTGGAAAACTACCTGTTCCATGGCCAACGCTT

GTCACTACTCTGACCTATGGTGTTCAATGCTTTTCCCGTTATCCGGATCACATGAAACAG

CATGACTTTTTCAAGAGTGCCATGCCCGAAGGTTATGTACAGGAACGCACTATATATTTC

AAAGATGACGGGAACTACAAGACGCGTGCTGTAGTCAAGTTTGAAGGTGATACCCTTGTT

AATCGTATCGAGTTAAAGGGTACTGATTTTAAAGAAGATGGAAACATTCTCGGACACAAA

CTCGAGTACAACTTTAACTCACACAATGTATATATCACGGCAGACAAACAAAAGAATGGA

ATCAAAGCTAACTTCACAATTCGCCACAACGTTGTAGATGGTTCCGTTCAACTAGCAGAC

CATTATCAACAAAATACTCCAATTGGCGATGGCCCTGTCCTTTTACCAGACAACCATTAC

TTGTCGACACAAACTGTCCTTTCGAAAGATCCCAACGAAAAGGGTACCTAA

-continued

TABLE OF SEQUENCES

SEQ ID NO:6
GFP 1-10 A4 amino acid sequence:
(additional mutations versus Superfolder GFP: R80Q, S99Y,
T105N, E111V, I128T, K166T, E172V, S205T)
MSKGEELFTGVVPILVELDGDVNGHKFSVRGEGEGDATNGKLTLKFICTTGKLPVPWPTL

VTTLTYGVQCFSRYPDHMKQHDFFKSAMPEGYVQERTIYFKDDGNYKTRAVVKFEGDTLV

NRIELKGTDFKEDGNILGHKLEYNFNSHNVYITADKQKNGIKANFTIRHNVVDGSVQLAD

HYQQNTPIGDGPVLLPDNHYLSTQTVLSKDPNEKGT

SEQ ID NO:7
GFP S11 214-238 nucleotide sequence:
AAGCGTGACCACATGGTCCTTCTTGAGTTTGTAACTGCTGCTGGGATTACACATGGCATG

GATGAGCTCTACAAAGGTACCTAA

SEQ ID NO:8
GFP S11 214-238 amino acid sequence:
KRDHMVLLEFVTAAGITHGMDELYKGT

SEQ ID NO:9
GFP S11 214-230 nucleotide sequence:
AAGCGTGACCACATGGTCCTTCTTGAGTTTGTAACTGCTGCTGGGATTACAGGTACCTAA SEQ ID NO:10
GFP S11 214-230 amino acid sequence:
KRDHMVLLEFVTAAGITGT SEQ ID NO:11
GFP S11 M1 nucleotide sequence:
AAGCGTGACCACATGGTCCTTCATGAGTTTGTAACTGCTGCTGGGATTACAGGTACCTAA SEQ ID NO:12
GFP S11 M1 amino acid sequence:
(Additional mutation versus wt: L221H)
KRDHMVLHEFVTAAGITGT SEQ ID NO:13
GFP S11 M2 nucleotide sequence:
AAGCGTGACCACATGGTCCTTCATGAGTCTGTAAATGCTGCTGGGGGTACCTAA SEQ ID NO:14
GFP S11 M2 amino acid sequence:
(Additional mutations versus GFP 11 wt: L221H, F223S, T225N
AA sequence 17 residues
KRDHMVLHESVNAAGGT SEQ ID NO:15
GFP S11 M3 nucleotide sequence:
CGTGACCACATGGTCCTTCATGAGTCTGTAAATGCTGCTGGGATTACATAA SEQ ID NO:16
GFP S11 M3 amino acid sequence:
(Additional mutations versus GFP 11 wt: L221H, F223Y, T225N)
RDHMVLHEYVNAAGIT*

SEQ ID NO:17
GFP S11 H7 nucleotide sequence:
AAGCATGACCACATGCACCTTCATGAGCATGTACATGCTCATGGGGGTACCTAA SEQ ID NO:18
GFP S11 H7 amino acid sequence:
(Additional mutations versus GFP 11 wt: R215H, V219H, L221H,
F223H, T225H, A227H)
KHDHMHLHEHVHAHGGT SEQ ID NO:19
GFP S11 H9 nucleotide sequence:
CATGACCACATGCACCTTCATGAGCATGTACATGCTCATCACCATACCTAA SEQ ID NO:20
GFP S11 H9 amino acid sequence:
(Additional mutations versus GFP 11 wt: R215H, V219H, L221H,
F223H, T225H, A227H, G228H, I229H)
HDHMHLHEHVHAHHHT

TABLE OF SEQUENCES

SEQ ID NO:21
UNIQUE GENETIC ELEMENTS FROM PTET-SPECR VECTOR
(These comprise the elements from T0 to Aat11: tet repressor
protein tetR and the Spectinomycin gene under the control
of the kanamycin promoter, and the RBS that control the ex-
pression of the tet repressor)
TTAAGACCCACTTTCACATTTAAGTTGTTTTTCTAATCCGTATATGATCAATTCAAGGCC

GAATAAGAAGGCTGGCTCTGCACCTTGGTGATCAAATAATTCGATAGCTTGTCGTAATAA

TGGCGGCATACTATCAGTAGTAGGTGTTTCCCTTTCTTCTTTAGCGACTTGATGCTCTTG

ATCTTCCAATACGCAACCTAAAGTAAAATGCCCCACAGCGCTGAGTGCATATAATGCATT

CTCTAGTGAAAAACCTTGTTGGCATAAAAAGGCTAATTGATTTTCGAGAGTTTCATACTG

TTTTTCTGTAGGCCGTGTACCTAAATGTACTTTTGCTCCATCGCGATGACTTAGTAAAGC

ACATCTAAAACTTTTAGCGTTATTACGTAAAAAATCTTGCCAGCTTTCCCCTTCTAAAGG

GCAAAAGTGAGTATGGTGCCTATCTAACATCTCAATGGCTAAGGCGTCGAGCAAAGCCCG

CTTATTTTTACATGCCAATACAATGTAGGCTGCTCTACACCTAGCTTCTGGGCGAGTTT

ACGGGTTGTTAAACCTTCGATTCCGACCTCATTAAGCAGCTCTAATGCGCTGTTAATCAC

TTTACTTTTATCTAATCTGGACATCATTAATGTTTATTGAGCTCTCGAACCCCAGAGTCC

CGCATTATTTGCCGACTACCTTGGTGATCTCGCCTTTCACGTAGTGGACAAATTCTTCCA

ACTGATCTGCGCGCGAGGCCAAGCGATCTTCTTCTTGTCCAAGATAAGCCTGTCTAGCTT

CAAGTATGACGGGCTGATACTGGGCCGGCAGGCGCTCCATTGCCCAGTCGGCAGCGACAT

CCTTCGGCGCGATTTTGCCGGTTACTGCGCTGTACCAAATGCGGGACAACGTAAGCACTA

CATTTCGCTCATCGCCAGCCCAGTCGGGCGGCGAGTTCCATAGCGTTAAGGTTTCATTTA

GCGCCTCAAATAGATCCTGTTCAGGAACCGGATCAAAGAGTTCCTCCGCCGCTGGACCTA

CCAAGGCAACGCTATGTTCTCTTGCTTTTGTCAGCAAGATAGCCAGATCAATGTCGATCG

TGGCTGGCTCGAAGATACCTGCAAGAATGTCATTGCGCTGCCATTCTCCAAATTGCAGTT

CGCGCTTAGCTGGATAACGCCACGGAATGATGTCGTCGTGCACAACAATGGTGACTTCTA

CAGCGCGGAGAATCTCGCTCTCTCCAGGGGAAGCCGAAGTTTCCAAAAGGTCGTTGATCA

AAGCTCGCCGCGTTGTTTCATCAAGCCTTACGGTCACCGTAACCAGCAAATCAATATCAC

TGTGTGGCTTCAGGCCGCCATCCACTGCGGAGCCGTACAAATGTACGGCCAGCAACGTCG

GTTCGAGATGGCGCTCGATGACGCCAACTACCTCTGATAGTTGAGTCGATACTTCGGCGA

TCACCGCTTCCCTCATGATGTTTAACTTTGTTTTAGGGCGACTGCCCTGCTGCGTAACAT

CGTTGCTGCTCCATAACATCAAACATCGACCCACGGCGTAACGCGCTTGCTGCTTGGATG

CCCGAGGCATAGACTGTACCCCAAAAAAACATGTCATAACAAGCCATGAAAACCGCCACT

GCGCCGTTACCATGCGAAACGATCCTCATCCTGTCTCTTGATCAGATCTTGATCCCCTGC

GCCATCAGATCCTTGGCGGCAAGAAAGCCATCCAGTTTACTTTGCAGGGCTTCCCAACCT

TACCAGAGGGCGCCCCAGCTGGCAATTCCGACGTC

SEQ ID NO:22
COMPLETE PTET-SPECR VECTOR SEQUENCE
TCGAGTCCCTATCAGTGATAGAGATTGACATCCCTATCAGTGATAGAGATACTGAGCACA

TCAGCAGGACGCACTGACCGAGTTCATTAAAGAGGAGAAAGATACCCATGGGCAGCAGCC

ATCATCATCATCATCACAGCAGCGGCCTGGTGCCGCGCGGCAGCCATATGGGTGGCGGTT

CTGGATCCGGAGGCACTAGTGGTGGCGGCTCAGGTACCTAACTCGAGCACCACCACCACC

-continued

TABLE OF SEQUENCES

ACCACTGAGATCCGGCTGCTAACAAAGCCCGAAAGGAAGCTGAGTTGGCTGCTGCCACCG

CTGAGCAATAACTAGCATAACCTCTAGAGGCATCAAATAAAACGAAAGGCTCAGTCGAAA

GACTGGGCCTTTCGTTTTATCTGTTGTTTGTCGGTGAACGCTCTCCTGAGTAGGACAAAT

CCGCCGCCCTAGACCTAGGCGTTCGGCTGCGGCGAGCGGTATCAGCTCACTCAAAGGCGG

TAATACGGTTATCCACAGAATCAGGGGATAACGCAGGAAAGAACATGTGAGCAAAAGGCC

AGCAAAAGGCCAGGAACCGTAAAAAGGCCGCGTTGCTGGCGTTTTTCCATAGGCTCCGCC

CCCCTGACGAGCATCACAAAAATCGACGCTCAAGTCAGAGGTGGCGAAACCCGACAGGAC

TATAAAGATACCAGGCGTTTCCCCCTGGAAGCTCGCTCGTGCGCTCTCCTGTTCCGACCC

TGCCGCTTACCGGATACCTGTCCGCCTTTCTCCCTTCGGGAAGCGTGGCGCTTTCTCAAT

GCTCACGCTGTAGGTATCTCAGTTCGGTGTAGGTCGTTCGCTCCAAGCTGGGCTGTGTGC

ACGAACCCCCCGTTCAGCCCGACCGCTGCGCCTTATCCGGTAACTATCGTCTTGAGTCCA

ACCCGGTAAGACACGACTTATCGCCACTGGCAGCAGCCACTGGTAACAGGATTAGCAGAG

CGAGGTATGTAGGCGGTGCTACAGAGTTCTTGAAGTGGTGGCCTAACTACGGCTACACTA

GAAGGACAGTATTTGGTATCTGCGCTCTGCTGAAGCCAGTTACCTTCGGAAAAAGAGTTG

GTAGCTCTTGATCCGGCAAACAAACCACCGCTGGTAGCGGTGGTTTTTTGTTTGCAAGC

AGCAGATTACGCGCAGAAAAAAGGATCTCAAGAAGATCCTTTGATCTTTTCTACGGGGT

CTGACGCTCAGTGGAACGAAAACTCACGTTAAGGGATTTTGGTCATGACTAGCGCTTGGA

TTCTCACCAATAAAAAACGCCCGGCGGCAACCGAGCGTTCTGAACAAATCCAGATGGAGT

TCTGAGGTCATTACTGGATCTATCAACAGGAGTCCAAGCTTAAGACCCACTTTCACATTT

AAGTTGTTTTTCTAATCCGTATATGATCAATTCAAGGCCGAATAAGAAGGCTGGCTCTGC

ACCTTGGTGATCAAATAATTCGATAGCTTGTCGTAATAATGGCGGCATACTATCAGTAGT

AGGTGTTTCCCTTTCTTCTTTAGCGACTTGATGCTCTTGATCTTCCAATACGCAACCTAA

AGTAAAATGCCCCACAGCGCTGAGTGCATATAATGCATTCTCTAGTGAAAAACCTTGTTG

GCATAAAAAGGCTAATTGATTTTCGAGAGTTTCATACTGTTTTTCTGTAGGCCGTGTACC

TAAATGTACTTTTGCTCCATCGCGATGACTTAGTAAAGCACATCTAAAACTTTTAGCGTT

ATTACGTAAAAAATCTTGCCAGCTTTCCCCTTCTAAAGGGCAAAAGTGAGTATGGTGCCT

ATCTAACATCTCAATGGCTAAGGCGTCGAGCAAAGCCCGCTTATTTTTTACATGCCAATA

CAATGTAGGCTGCTCTACACCTAGCTTCTGGGCGAGTTTACGGGTTGTTAAACCTTCGAT

TCCGACCTCATTAAGCAGCTCTAATGCGCTGTTAATCACTTTACTTTTATCTAATCTGGA

CATCATTAATGTTTATTGAGCTCTCGAACCCCAGAGTCCCGCATTATTTGCCGACTACCT

TGGTGATCTCGCCTTTCACGTAGTGGACAAATTCTTCGAACTGATCTGCGCGCGAGGCCA

AGCGATCTTCTTCTTGTCCAAGATAAGCCTGTCTAGCTTCAAGTATGACGGGCTGATACT

GGGCCGGCAGGCGCTCCATTGCCCAGTCGGCAGCGACATCCTTCGGCGCGATTTTGCCGG

TTACTGCGCTGTACCAAATGCGGGACAACGTAAGCACTACATTTCGCTCATCGCCAGCCC

AGTCGGGCGGCGAGTTCCATAGCGTTAAGGTTTCATTTAGCGCCTCAAATAGATCCTGTT

CAGGAACCGGATCAAAGAGTTCCTCCGCCGCTGGACCTACCAAGGCAACGCTATGTTCTC

TTGCTTTTGTCAGCAAGATAGCCAGATCAATGTCGATCGTGGCTGGCTCGAAGATACCTG

CAAGAATGTCATTGCGCTGCCATTCTCCAAATTGCAGTTCGCGCTTAGCTGGATAACGCC

ACGGAATGATGTCGTCGTGCACAACAATGGTGACTTCTACAGCGCGGAGAATCTCGCTCT

TABLE OF SEQUENCES

CTCCAGGGGAAGCCGAAGTTTCCAAAAGGTCGTTGATCAAAGCTCGCCGCGTTGTTTCAT

CAAGCCTTACGGTCACCGTAACCAGCAAATCAATATCACTGTGTGGCTTCAGGCCGCCAT

CCACTGCGGAGCCGTACAAATGTACGGCCAGCAACGTCGGTTCGAGATGGCGCTCGATGA

CGCCAACTACCTCTGATAGTTGAGTCGATACTTCGGCGATCACCGCTTCCCTCATGATGT

TTAACTTTGTTTTAGGGCGACTGCCCTGCTGCGTAACATCGTTGCTGCTCCATAACATCA

AACATCGACCCACGGCGTAACGCGCTTGCTGCTTGGATGCCCGAGGCATAGACTGTACCC

CAAAAAAACATGTCATAACAAGCCATGAAAACCGCCACTGCGCCGTTACCATGCGAAACG

ATCCTCATCCTGTCTCTTGATCAGATCTTGATCCCCTGCGCCATCAGATCCTTGGCGGCA

AGAAAGCCATCCAGTTTACTTTGCAGGGCTTCCCAACCTTACCAGAGGGCGCCCCAGCTG

GCAATTCCGACGTCTAAGAAACCATTATTATCATGACATTAACCTATAAAAATAGGCGTA

TCACGAGGCCCTTTCGTCTTCACC

SEQ ID NO:23
Nucleotide sequence of GFP 1-9 OPT
ATGCGCAAAGGAGAAGAACTTTTCACTGGAGTTGTCCCAATTCTTGTTGAATTAGATGGT

GATGTTAATGGGCACAAATTTTCTGTCCGTGGAGAGGGTGAAGGTGATGCTACAAACGGA

AAACTCAGCCTTAAATTTATTTGCACTACTGGAAAACTACCTGTTCCATGGCCAACACTT

GTCACTACTCTGACCTATGGTGTTCAATGCTTTTCCCGTTATCCGGATCACATGAAACGG

CATGACTTTTTCAAGAGTGTCATGCCCGAAGGTTATGTACAGGAACGCACTATATCTTTC

AAAGATGACGGGACCTACAAGACGCGTGCTGAAGTCAAGTCTGAAGGTGATACCCTTGTT

AATCGTATCGAGTTAAAAGGTATTGATTTTAAAGAAGATGGAAACATTCTCGGACACAAA

CTCGAGTACAACTTTAACTCACACAATGTATACATCACGGCAGACAAACAAAAGAATGGA

ATCAAAGCTAACTTCACAATTCGCCACAACGTTGAAGATGGTTCCGTTCAACTAGCAGAC

CATTATCAACAAATACTCCAATTGGCGATGGCCCTGTCCTTTTACCAGACAATAA

SEQ ID NO:24
Amino sequence of GFP 1-9 OPT
MRKGEELFTGWPILVELDGDVNGHKFSVRGEGEGDATNGKLSLKFICTTGKLPVPWPTLV

TTLTYGVQCFSRYPDHMKRHDFFKSVMPEGYVQERTISFKDDGTYKTPAEVKSEGDTLVN

RIELKGIDFKEDGNILGHKLEYNFNSHNVYITADKQKNGIKANFTIRHNVEDGSVQLADH

YQQNTPIGDGPVLLPD

SEQ ID NO:25
Amino acid sequence of GFP 10-11 OPT
DHYLSTQTILSKDPNEERDHMVLLESVTAAGITHGMDELYK SEQ ID NO:26
Amino acid sequence of NcoI (GFP S10 A4)-KpnI-linker-NdeI-
BamHI-linker-SpeI-(GFP S11 SM5)-NheI-XhoI "10-x-11 sandwich
optimum".
YTMDLPDDHYLSTQTILSKDLNGTDVGSGGGSHMGGGSGSGGGSGGGSTSEKRDHMVLLE

YVTAAGITDAS

SEQ ID NO:27
Nucleotide sequence of GFP 1-10 OPT + GFP S11 M2 "GFP 1-10
OPT M2".
ATGAGCAAAGGAGAAGAACTTTTCACTGGAGTTGTCCCAATTCTTGTTGAATTAGATGGT

GATGTTAATGGGCACAAATTTTCTGTCAGAGGAGAGGGTGAAGGTGATGCTACAATCGGA

AAACTCACCCTTAAATTTATTTGCACTACTGGAAAACTACCTGTTCCATGGCCAACACTT

GTCACTACTCTGACCTATGGTGTTCAATGCTTTTCCCGTTATCCGGATCACATGAAAAGG

TABLE OF SEQUENCES

```
CATGACTTTTTCAAGAGTGCCATGCCCGAAGGTTATGTACAGGAACGCACTATATCTTTC

AAAGATGACGGGAAATACAAGACGCGTGCTGTAGTCAAGTTTGAAGGTGATACCCTTGTT

AATCGTATCGAGTTAAAGGGTACTGATTTTAAAGAAGATGGAAACATTCTCGGACACAAA

CTCGAGTACAACTTTAACTCACACAATGTATACATCACGGCAGACAAACAAAAGAATGGA

ATCAAAGCTAACTTCACAGTTCGCCACAACGTTGAAGATGGTTCCGTTCAACTAGCAGAC

CATTATCAACAAAATACTCCAATTGGCGATGGCCCTGTCCTTTTACCAGACAACCATTAC

CTGTCGACACAAACTGTCCTTTCGAAAGATCCCAACGAAAAGCGTGACCACATGGTCCTT

CATGAGTCTGTAAATGCTGCTGGGATTACATAA
```

SEQ ID NO:28
Amino acid sequence of GFP 1-10 OPT + GFP S11 M2 "GFP 1-10 OPT M2".

```
MSKGEELFTGVVPILVELDGDVNGHKFSVRGEGEGDATIGKLTLKFICTTGKLPVPWPTL

VTTLTYGVQCFSRYPDHMKRHDFFKSAMPEGYVQERTISFKDDGKYKTRAVVKFEGDTLV

NRIELKGTDFKEDGNILGHKLEYNFNSHNVYITADKQKNGIKANFTVRHNVEDGSVQLAD

HYQQNTPIGDGPVLLPDNHYLSTQTVLSKDPNEKRDHMVLHESVNAAGIT*
```

SEQ ID NO:29
Nucleotide acid sequence of GFP 1-10 OPT + GFP S11 M2 + tail of GFP "GFP 1-10 OPT M2 tailed".

```
ATGAGCAAAGGAGAAGAACTTTTCACTGGAGTTGTCCCAATTCTTGTTGAATTAGATGGT

GATGTTAATGGGCACAAATTTTCTGTCAGAGGAGAGGGTGAAGGTGATGCTACAATCGGA

AAACTCACCCTTAAATTTATTTGCACTACTGGAAAACTACCTGTTCCATGGCCAACACTT

GTCACTACTCTGACCTATGGTGTTCAATGCTTTTCCCGTTATCCGGATCACATGAAAAGG

CATGACTTTTTCAAGAGTGCCATGCCCGAAGGTTATGTACAGGAACGCACTATATCTTTC

AAAGATGACGGGAAATACAAGACGCGTGCTGTAGTCAAGTTTGAAGGTGATACCCTTGTT

AATCGTATCGAGTTAAAGGGTACTGATTTTAAAGAAGATGGAAACATTCTCGGACACAAA

CTCGAGTACAACTTTAACTCACACAATGTATACATCACGGCAGACAAACAAAAGAATGGA

ATCAAAGCTAACTTCACAGTTCGCCACAACGTTGAAGATGGTTCCGTTCAACTAGCAGAC

CATTATCAACAAAATACTCCAATTGGCGATGGCCCTGTCCTTTTACCAGACAACCATTAC

CTGTCGACACAAACTGTCCTTTCGAAAGATCCCAACGAAAAGCGTGACCACATGGTCCTT

CATGAGTCTGTAAATGCTGCTGGGATTACACATGGCATGGATGAGCTCTACAAATAA
```

SEQ ID NO:30
Amino acid sequence of GFP 1-10 OPT + GFP S11 M2 + tail of GFP "GFP 1-10 OPT M2 tailed".

```
MSKGEELFTGVVPILVELDGDVNGHKFSVRGEGEGDATIGKLTLKFICTTGKLPVPWPTL

VTTLTYGVQCFSRYPDHMKRHDFFKSAMPEGYVQERTISFKDDGKYKTRAVVKFEGDTLV

NRIELKGTDFKEDGNILGHKLEYNFNSHNVYITADKQKNGIKANFTVRHNVEDGSVQLAD

HYQQNTPIGDGPVLLPDNHYLSTQTVLSKDPNEKRDHMVLHESVNAAGITHGMDELYK*
```

SEQ ID NO:31
Nucleotide a sequence of GFP 10-11 OPT.

```
GACCATTACCTGTCGACACAAACTATCCTTTCGAAAGATCCCAACGAAGAGCGTGACCAC

ATGGTCCTTCTTGAGTCTGTAACTGCTGCTGGGATTACACATGGCATGGATGAGCTCTAC

AAAT
```

SEQ ID NO:32
Nucleotide sequence of NcoI (GFP S10 A4)-KpnI-linker-NdeI-BamHI-linker-SpeI-(GFP S11 SM5)-NheI-XhoI "10-x-11 sandwich

TABLE OF SEQUENCES optimum".
GATATACCATGGATTTACCAGACGACCATTACCTGTCGACACAAACTATCCTTTCGAAAG

ATCTCAACGGTACCGACGTTGGGTCTGGCGGTGGCTCCCATATGGGTGGCGGTTCTGGAT

CCGGTGGAGGGTCTGGTGGCGGATCAACTAGTGAAAAGCGTGACCACATGGTCCTTCTTG

AGTATGTAACTGCTGCTGGGATTACAGATGCTAGCTAACTCGAGAATAGC

SEQ ID NO:33
Nucleotide sequence of GFP 1-10 OPT + GFP S11 M3 "GFP 1-10
OPT M3".
ATGAGCAAAGGAGAAGAACTTTTCACTGGAGTTGTCCCAATTCTTGTTGAATTAGATGGT

GATGTTAATGGGCACAAATTTTCTGTCAGAGGAGAGGGTGAAGGTGATGCTACAATCGGA

AAACTCACCCTTAAATTTATTTGCACTACTGGAAAACTACCTGTTCCATGGCCAACACTT

GTCACTACTCTGACCTATGGTGTTCAATGCTTTTCCCGTTATCCGGATCACATGAAAGG

CATGACTTTTTCAAGAGTGCCATGCCCGAAGGTTATGTACAGGAACGCACTATATCTTTC

AAAGATGACGGGAAATACAAGACGCGTGCTGTAGTCAAGTTTGAAGGTGATACCCTTGTT

AATCGTATCGAGTTAAAGGGTACTGATTTTAAAGAAGATGGAAACATTCTCGGACACAAA

CTCGAGTACAACTTTAACTCACACAATGTATACATCACGGCAGACAAACAAAGAATGGA

ATCAAAGCTAACTTCACAGTTCGCCACAACGTTGAAGATGGTTCCGTTCAACTAGCAGAC

CATTATCAACAAATACTCCAATTGGCGATGGCCCTGTCCTTTTACCAGACAACCATTAC

CTGTCGACACAAACTGTCCTTTCGAAAGATCCCAACGAAAGCGTGACCACATGGTCCTT

CATGAGTACGTAAATGCTGCTGGGATTACATAA

SEQ ID NO:34
Amino acid sequence of GFP 1-10 OPT + GFP S11 M3 "GFP 1-10
OPT M3".
MSKGEELFTGVVPILVELDGDVNGHKFSVRGEGEGDATIGKLTLKFICTTGKLPVPWPTL

VTTLTYGVQCFSRYPDHMKRHDFFKSAMPEGYVQERTISFKDDGKYKTRAVVKFEGDTLV

NRIELKGTDFKEDGNILGHKLEYNFNSHNVYITADKQKNGIKANFTVRHNVEDGSVQLAD

HYQQNTPIGDGPVLLPDNHYLSTQTVLSKDPNEKRDHMVLHEYVNAAGIT*

SEQ ID NO:35
Nucleotide acid sequence of GFP 1-10 OPT + GFP S11 M3 + tail
of GFP "GFP 1-10 OPT M3 tailed".
ATGAGCAAAGGAGAAGAACTTTTCACTGGAGTTGTCCCAATTCTTGTTGAATTAGATGGT

GATGTTAATGGGCACAAATTTTCTGTCAGAGGAGAGGGTGAAGGTGATGCTACAATCGGA

AAACTCACCCTTAAATTTATTTGCACTACTGGAAAACTACCTGTTCCATGGCCAACACTT

GTCACTACTCTGACCTATGGTGTTCAATGCTTTTCCCGTTATCCGGATCACATGAAAGG

CATGACTTTTTCAAGAGTGCCATGCCCGAAGGTTATGTACAGGAACGCACTATATCTTTC

AAAGATGACGGGAAATACAAGACGCGTGCTGTAGTCAAGTTTGAAGGTGATACCCTTGTT

AATCGTATCGAGTTAAAGGGTACTGATTTTAAAGAAGATGGAAACATTCTCGGACACAAA

CTCGAGTACAACTTTAACTCACACAATGTATACATCACGGCAGACAAACAAAGAATGGA

ATCAAAGCTAACTTCACAGTTCGCCACAACGTTGAAGATGGTTCCGTTCAACTAGCAGAC

CATTATCAACAAATACTCCAATTGGCGATGGCCCTGTCCTTTTACCAGACAACCATTAC

CTGTCGACACAAACTGTCCTTTCGAAAGATCCCAACGAAAGCGTGACCACATGGTCCTT

CATGAGTACGTAAATGCTGCTGGGATTACACATGGCATGGATGAGCTCTACAAATAA

SEQ ID NO:36
Amino acid sequence of GFP 1-10 OPT + GFP S11 M3 + tail of
GFP "GFP 1-10 OPT M3 tailed".

MSKGEELFTGVVPILVELDGDVNGHKFSVRGEGEGDATIGKLTLKFICTTGKLPVPWPTL

VTTLTYGVQCFSRYPDHMKRHDFFKSAMPEGYVQERTISFKDDGKYKTRAVVKFEGDTLV

NRIELKGTDFKEDGNILGHKLEYNFNSHNVYITADKQKNGIKANFTVRHNVEDGSVQLAD

HYQQNTPIGDGPVLLPDNHYLSTQTVLSKDPNEKRDHMVLHEYVNAAGITHGMDELYK*

SEQ ID NO:61
Nucleotide sequence for MTS-SR-s11-6his construct:
ATGTCCGTCCTGACGCCGCTGCTGCTGCGGGGCTTGACAGGCTCGGCCCGGCGGCTCCCA

GTGCCGCGCGCCAAGATCCATTCGTTGGGGGACCCACCGGTCGCCACCGGTGGCGGTTCT

CATATGCCAGTGAAATGTCCCGGCGAGTACCAAGTTGATGGCAAAAAAGTTATACTAGAC

GAGGACTGTTTTATGCAAAACCCAGAGGACTGGGACGAAAAAGTGGCTGAGTGGTTGGCC

AGAGAGCTAGAGGGCATACAAAAAATGACCGAGGAGCATTGGAAGTTGGTAAAATACTTA

AGGGAGTATTGGGAGACCTTCGGCTCCTGCCCGCCAATTAAAATGGTCACTAAAGAGACG

GGCTTCTCCTTGGAGAAAATCTACCAGCTATTCCCCTCGGGGCCTGCGCACGGAGCTTGT

AAAGTGGCAGGCGCGCCGAAGCCCACAGGCTGCGTCGGATCCGATGGAGGGTCTGGTGGC

GGATCAACAAGCCGTGACCACATGGTCCTTCATGAGTACGTAAATGCTGCTGGGATTACA

GGTACCGGTGGCGGTTCTCTCGAGCACCACCACCACCACCACTGA

SEQ ID NO:62
Amino-acid sequence for MTS-SR-s11-6his construct
MSVLTPLLLRGLTGSARRLPVPRAKIHSLGDPPVATGGGSHMPVKCPGEYQVDGKKVILD

EDCFMQNPEDWDEKVAEWLARELEGIQKMTEEHWKLVKYLREYWETFGSCPPIKMVTKET

GFSLEKIYQLFPSGPAHGACKVAGAPKPTGCVGSDGGSGGGSTSRDHMVLHEYVNAAGIT

GTGGGSLEHHHHHH*

SEQ ID NO:63
Nucleotide sequence for MTS-(1-10) opt-6his construct
ATGTCCGTCCTGACGCCGCTGCTGCTGCGGGGCTTGACAGGCTCGGCCCGGCGGCTCCCA

GTGCCGCGCGCCAAGATCCATTCGTTGGGGGACCCACCGGTCGCCACCGGTGGCGGTTCT

CATATGATGAGCAAAGGAGAAGAACTTTTCACTGGAGTTGTCCCAATTCTTGTTGAATTA

GATGGTGATGTTAATGGGCACAAATTTTCTGTCAGAGGAGAGGGTGAAGGTGATGCTACA

ATCGGAAAACTCACCCTTAAATTTATTTGCACTACTGGAAAACTACCTGTTCCATGGCCA

ACACTTGTCACTACTCTGACCTATGGTGTTCAATGCTTTTCCCGTTATCCGGATCACATG

AAAAGGCATGACTTTTTCAAGAGTGCCATGCCCGAAGGTTATGTACAGGAACGCACTATA

TCTTTCAAAGATGACGGGAAATACAAGACGCGTGCTGTAGTCAAGTTTGAAGGTGATACC

CTTGTTAATCGTATCGAGTTAAAGGGTACTGATTTTAAAGAAGATGGAAACATTCTCGGA

CACAAACTCGAGTACAACTTTAACTCACACAATGTATACATCACGGCAGACAAACAAAAG

AATGGAATCAAAGCTAACTTCACAGTTCGCCACAACGTTGAAGATGGTTCCGTTCAACTA

GCAGACCATTATCAACAAAATACTCCAATTGGCGATGGCCCTGTCCTTTTACCAGACAAC

CATTACCTGTCGACACAAACTGTCCTTTCGAAAGATCCCAACGAAAAGGGTACCGGTACC

GGTGGCGGTTCTCTCGAGCACCACCACCACCACCACTGA

SEQ ID NO:64
Amino-acid sequence for MTS-(1-10) opt-6his construct
MSVLTPLLLRGLTGSARRLPVPRAKIHSLGDPPVATGGGSHMMSKGEELFTGVVPILVEL

DGDVNGHKFSVRGEGEGDATIGKLTLKFICTTGKLPVPWPTLVTTLTYGVQCFSRYPDHM

KRHDFFKSAMPEGYVQERTISFKDDGKYKTRAVVKFEGDTLVNRIELKGTDFKEDGNILG

TABLE OF SEQUENCES

HKLEYNFNSHNVYITADKQKNGIKANFTVRHNVEDGSVQLADHYQQNTPIGDGPVLLPDN

HYLSTQTVLSKDPNEKGTGTGGGSLEHHHHHH*

SEQ ID NO:65
Receiving vector for nuclear localization (N6his-linker-s11-SR*)
ATGGGCCACCACCACCACCACCACGGTGGCGGTTCTACTAGTCGTGACCACATGGTCCTT

CATGAGTACGTAAATGCTGCTGGGATTACAGGTACCGATGGAGGGTCTGGTGGCGGATCA

CATATGCCAGTGAAATGTCCCGGCGAGTACCAAGTTGATGGCAAAAAAGTTATACTAGAC

GAGGACTGTTTTATGCAAAACCCAGAGGACTGGGACGAAAAAGTGGCTGAGTGGTTGGCC

AGAGAGCTAGAGGGCATACAAAAAATGACCGAGGAGCATTGGAAGTTGGTAAATACTTA

AGGGAGTATTGGGAGACCTTCGGCTCCTGCCCGCCAATTAAAATGGTCACTAAAGAGACG

GGCTTCTCCTTGGAGAAAATCTACCAGCTATTCCCCTCGGGGCCTGCGCACGGAGCTTGT

AAAGTGGCAGGCGCGCCGAAGCCCACAGGCTGCGTCGGATCCTAACTCGAGCACCACCAC

CACCACCACTGA

SEQ ID NO:66
AA sequence receiving vector for nuclear localization
(N6his-linker-s11-SR*)
MGHHHHHHGGGSTSRDHMVLHEYVNAAGITGTDGGSGGGSHMPVKCPGEYQVDGKKVILD

EDCFMQNPEDWDEKVAEWLARELEGIQKMTEEHWKLVKYLREYWETFGSCPPIKMVTKET

GFSLEKIYQLFPSGPAHGACKVAGAPKPTGCVGS*LEHHHHHH*

SEQ ID NO:67
Nucleotide sequence for 6his-s11-SR-NLS construct:
ATGGGCCACCACCACCACCACCACGGTGGCGGTTCTACTAGTCGTGACCACATGGTCCTT

CATGAGTACGTAAATGCTGCTGGGATTACAGGTACCGATGGAGGGTCTGGTGGCGGATCA

CATATGCCAGTGAAATGTCCCGGCGAGTACCAAGTTGATGGCAAAAAAGTTATACTAGAC

GAGGACTGTTTTATGCAAAACCCAGAGGACTGGGACGAAAAAGTGGCTGAGTGGTTGGCC

AGAGAGCTAGAGGGCATACAAAAAATGACCGAGGAGCATTGGAAGTTGGTAAATACTTA

AGGGAGTATTGGGAGACCTTCGGCTCCTGCCCGCCAATTAAAATGGTCACTAAAGAGACG

GGCTTCTCCTTGGAGAAAATCTACCAGCTATTCCCCTCGGGGCCTGCGCACGGAGCTTGT

AAAGTGGCAGGCGCGCCGAAGCCCACAGGCTGCGTCGGATCCGGTGGCGGTTCTTCCAAA

AAAGAAGAGAAAGGTAGATCCAAAAAAGAAGAGAAAGGTAGATCCAAAAAAGAAGAGAAA

GGTAGGATACACCGGATATAACTCGAG

SEQ ID NO:68
Amino-acid sequence for 6his-s11-SR-NLS construct:
MGHHHHHHGGGSTSRDHMVLHEYVNAAGITGTDGGSGGGSHMPVKCPGEYQVDGKKVILD

EDCFMQNPEDWDEKVAEWLARELEGIQKMTEEHWKLVKYLREYWETFGSCPPIKMVTKET

GFSLEKIYQLFPSGPAHGACKVAGAPKPTGCVGSGGGGSSKKEEKGRSKKEEKGRSKKEEK

GRIHRI*LE

SEQ ID NO:69
Nucleotide sequence for 6his-(1-10opt)-NLS construct:
ATGGGCCACCACCACCACCACCACGGTGGCGGTTCTACTAGTATGAGCAAAGGAGAAGAA

CTTTTCACTGGAGTTGTCCCAATTCTTGTTGAATTAGATGGTGATGTTAATGGGCACAAA

TTTTCTGTCAGAGGAGAGGGTGAAGGTGATGCTACAATCGGAAAACTCACCCTTAAATTT

ATTTGCACTACTGGAAAACTACCTGTTCCATGGCCAACACTTGTCACTACTCTGACCTAT

-continued

TABLE OF SEQUENCES

GGTGTTCAATGCTTTTCCCGTTATCCGGATCACATGAAAAGGCATGACTTTTTCAAGAGT

GCCATGCCCGAAGGTTATGTACAGGAACGCACTATATCTTTCAAAGATGACGGGAAATAC

AAGACGCGTGCTGTAGTCAAGTTTGAAGGTGATACCCTTGTTAATCGTATCGAGTTAAAG

GGTACTGATTTTAAAGAAGATGGAAACATTCTCGGACACAAACTCGAGTACAACTTTAAC

TCACACAATGTATACATCACGGCAGACAAACAAAAGAATGGAATCAAAGCTAACTTCACA

GTTCGCCACAACGTTGAAGATGGTTCCGTTCAACTAGCAGACCATTATCAACAAAATACT

CCAATTGGCGATGGCCCTGTCCTTTTACCAGACAACCATTACCTGTCGACACAAACTGTC

CTTTCGAAAGATCCCAACGAAAAGGGTACCGGATCCGGTGGCGGTTCTTCCAAAAAAGAA

GAGAAAGGTAGATCCAAAAAAGAAGAGAAAGGTAGATCCAAAAAAGAAGAGAAAGGTAGG

ATACACCGGATATAACTCGAG

SEQ ID NO:70
Amino-acid sequence for 6his-(1-10opt)-NLS construct:
MGHHHHHHGGGSTSMSKGEELFTGVVPILVELDGDVNGHKFSVRGEGEGDATIGKLTLKF

ICTTGKLPVPWPTLVTTLTYGVQCFSRYPDHMKRHDFFKSAMPEGYVQERTISFKDDGKY

KTRAWKFEGDTLVNRIELKGTDFKEDGNILGHKLEYNFNSHNVYITADKQKNGIKANFTV

RHNVEDGSVQLADHYQQNTPIGDGPVLLPDNHYLSTQTVLSKDPNEKGTGSGGGSSKKEE

KGRSKKEEKGRSKKEEKGRIHRI*LE

SEQ ID NO:71
Nucleotide sequence for CAL-SR-s11-6his-KDEL construct:
ATGCTGCTATCCGTGCCGTTGCTGCTCGGCCTCCTCGGCCTGGCCGTCGCCGACCGGTCG

CACACCATGGGTGGCGGTTCTCATATGCCAGTGAAATGTCCCGGCGAGTACCAAGTTGAT

GGCAAAAAAGTTATACTAGACGAGGACTGTTTTATGCAAAACCCAGAGGACTGGGACGAA

AAAGTGGCTGAGTGGTTGGCCAGAGAGCTAGAGGGCATACAAAAAATGACCGAGGAGCAT

TGGAAGTTGGTAAAATACTTAAGGGAGTATTGGGAGACCTTCGGCTCCTGCCCGCCAATT

AAAATGGTCACTAAAGAGACGGGCTTCTCCTTGGAGAAAATCTACCAGCTATTCCCCTCG

GGGCCTGCGCACGGAGCTTGTAAAGTGGCAGGCGCGCCGAAGCCCACAGGCTGCGTCGGA

TCCGATGGAGGGTCTGGTGGCGGATCAACAAGCCGTGACCACATGGTCCTTCATGAGTAC

GTAAATGCTGCTGGGATTACAGGTACCGGTGGCGGTTCTCTCGAGCACCACCACCACCAC

CACGGTGGCGGTTCTAAGGACGAGCTGTAA

SEQ ID NO:72
Amino-acid sequence for CAL-SR-s11-6his-KDEL construct:
MLLSVPLLLGLLGLAVADRSHTMGGGSHMPVKCPGEYQVDGKKVILDEDCFMQNPEDWDE

KVAEWLARELEGIQKMTEEHWKLVKYLREYWETFGSCPPIKMVTKETGFSLEKIYQLFPS

GPAHGACKVAGAPKPTGCVGSDGGSGGGSTSRDHMVLHEYVNAAGITGTGGGSLEHHHHH

HGGGSKDEL*

SEQ ID NO:73
Nucleotide sequence for CAL-(1-10)opt-6his-KDEL construct:
ATGCTGCTATCCGTGCCGTTGCTGCTCGGCCTCCTCGGCCTGGCCGTCGCCGACCGGTCG

CACACCATGGGTGGCGGTTCTCATATGATGAGCAAAGGAGAAGAACTTTTCACTGGAGTT

GTCCCAATTCTTGTTGAATTAGATGGTGATGTTAATGGGCACAAATTTTCTGTCAGAGGA

GAGGGTGAAGGTGATGCTACAATCGGAAAACTCACCCTTAAATTTATTTGCACTACTGGA

AAACTACCTGTTCCATGGCCAACACTTGTCACTACTCTGACCTATGGTGTTCAATGCTTT

TCCCGTTATCCGGATCACATGAAAAGGCATGACTTTTTCAAGAGTGCCATGCCCGAAGGT

-continued

TABLE OF SEQUENCES

TATGTACAGGAACGCACTATATCTTTCAAAGATGACGGGAAATACAAGACGCGTGCTGTA

GTCAAGTTTGAAGGTGATACCCTTGTTAATCGTATCGAGTTAAAGGGTACTGATTTTAAA

GAAGATGGAAACATTCTCGGACACAAACTCGAGTACAACTTTAACTCACACAATGTATAC

ATCACGGCAGACAAACAAAAGAATGGAATCAAAGCTAACTTCACAGTTCGCCACAACGTT

GAAGATGGTTCCGTTCAACTAGCAGACCATTATCAACAAAATACTCCAATTGGCGATGGC

CCTGTCCTTTTAGCAGACAACCATTACCTGTCGACACAAACTGTCCTTTCGAAAGATCCC

AACGAAAAGGGTACCGGTACCGGTGGCGGTTCTCTCGAGCACCACCACCACCACCACGGT

GGCGGTTCTAAGGACGAGCTGTAA

SEQ ID NO:74
Amino-acid sequence for CAL-(1-10) opt-6his-KDEL construct:
MLLSVPLLLGLLGLAVADRSHTMGGGSHMMSKGEELFTGVVPILVELDGDVNGHKFSVRG

EGEGDATIGKLTLKFICTTGKLPVPWPTLVTTLTYGVQCFSRYPDHMKRHDFFKSAMPEG

YVQERTISFKDDGKYKTRAVVKFEGDTLVNRIELKGTDFKEDGNILGHKLEYNFNSHNVY

ITADKQKNGIKANFTVRHNVEDGSVQLADHYQQNTPIGDGPVLLPDNHYLSTQTVLSKDP

NEKGTGTGGGSLEHHHHHHGGGSKDEL*

---

The invention claimed is:

1. An assay for detecting the localization of a test protein, X, to a subcellular component of interest in a cell, comprising:
   (a) expressing in the cell or providing to the cell (i) a fusion protein comprising the test protein, X, and a microdomain tag fragment of a fluorescent protein, wherein the microdomain tag fragment corresponds to one or more contiguous beta-strands of the fluorescent protein, and (ii) a complementary assay fragment of the fluorescent protein functionalized to be directed and localized to the subcellular component of interest, wherein the assay fragment corresponds to the remaining contiguous beta-strands of the fluorescent protein, and wherein the microdomain tag and complementary assay fragments self-complement to reconstitute the fluorescent protein if present in the same subcellular component; and,
   (b) detecting fluorescence in the cell, and thereby detecting the localization of the test protein, X, to the subcellular component of interest.

2. The assay according to claim 1, wherein the cell is a eukaryotic cell.

3. The assay according to claim 1 or 2, wherein the microdomain tag fragment corresponds to a single beta-strand of the fluorescent protein, and the assay fragment corresponds to the remaining ten beta-strands of the fluorescent protein.

4. The assay according to claim 3, wherein the microdomain tag fragment corresponds to beta-strand s11 and the assay fragment corresponds to beta-strands s1-10.

5. The assay according to claim 4, wherein the microdomain tag fragment is selected from the group consisting of SEQ ID NOS: 12, 14 and 16.

6. The assay according to claim 4, wherein the assay fragment is selected from the group consisting of SEQ ID NOS: 4 and 6.

7. The assay according to claim 1 or 2, wherein the assay fragment is fused in appropriate orientation to a polypeptide localization signal capable of directing and localizing the assay fragment to the nucleus, cytoplasm, plasma membrane, endoplasmic reticulum, golgi apparatus, actin and tubulin filaments, endosomes, peroxisomes or mitochondria.

8. The assay according to claim 7, wherein the fusion protein comprising the test protein X and the microdomain tag fragment further comprises an appropriately oriented localization signal capable of directing and localizing the fusion protein to the same subcellular compartment to which the assay fragment is directed.

9. An assay for detecting the localization of a test protein, X, to one or more of a plurality of subcellular components of interest in a cell, comprising:
   (a) expressing in the cell or providing to the cell (i) a fusion protein comprising the test protein, X, and a microdomain tag fragment of a fluorescent protein, wherein the microdomain tag fragment corresponds to one or more contiguous beta-strands of the fluorescent protein, and (ii) a plurality of complementary assay fragments of the fluorescent protein, wherein each of which assay fragments corresponds to the remaining contiguous beta-strands of the fluorescent protein, is functionalized to be directed and localized to a different subcellular component of interest, designed or selected to produce different color fluorescence upon complementation with the microdomain tag fragment, and complements with the microdomain tag fragment to reconstitute the fluorescent protein, if present in the same subcellular component; and,
   (b) detecting the various color fluorescence signals in cell, and thereby detecting the localization of the test protein, X, to one or more of the subcellular components of interest.

10. The assay according to claim 9, wherein the cell is a eukaryotic cell.

11. The assay according to claim 9 or 10, wherein the microdomain tag fragment corresponds to a single beta-strand of the fluorescent protein, and the assay fragment corresponds to the remaining ten beta-strands of the fluorescent protein.

12. The assay according to claim 11, wherein the microdomain tag fragment corresponds to beta-strand a11 and the assay fragments corresponds to beta-strands s1-10.

13. The assay according to claim 12, wherein the microdomain tag fragment is selected from the group consisting of SEQ ID NOs: 12, 14 and 16.

14. The assay according to claim 12, wherein the assay fragments are selected from the group consisting of SEQ ID NOs: 4 and 6.

* * * * *

SEQUENCE LISTING

<160> NUMBER OF SEQ ID NOS: 74

<210> SEQ ID NO 1
<211> LENGTH: 646
<212> TYPE: DNA
<213> ORGANISM: Artificial Sequence
<220> FEATURE:
<223> OTHER INFORMATION: GFP variant fragment; sequence encoding
      fragment corresponding to B-strands 1-10

<400> SEQUENCE: 1

```
atgagcaaag gagaagaact tttcactgga gttgtcccaa ttcttgttga attagatggt      60
gatgttaatg gcacaaaatt ttctgtcaga ggagagggtg aaggtgatgc tacaaacgga     120
aaactcaccc ttaaatttat ttgcactact ggaaaactac ctgttccatg gccaacactt     180
gtcactactc tgacctatgg tgttcaatgc ttttcccgtt atccggatca catgaaacgg     240
catgactttt tcaagagtgc catgcccgaa ggttatgtac aggaacgcac tatatctttc     300
aaagatgacg ggacctacaa gacgcgtgct gaagtcaagt tgaaggtga taccttgtt      360 aatcgtatcg agttaaaagg tattgatttt aagaagatg gaaacattct cggacacaaa     420
ctcgagtaca actttaactc acacaatgta tacatcacgg cagacaaaca aaagaatgga     480
atcaaagcta acttcaaaat tcgccacaac gttgaagatg gttccgttca actagcagac     540
cattatcaac aaaatactcc aattggcgat ggccctgtcc ttttaccaga caaccattac     600
ctgtcgacac aatctgtcct ttcgaaagat cccaacgaaa agctaa               646
```

<210> SEQ ID NO 2
<211> LENGTH: 214
<212> TYPE: PRT
<213> ORGANISM: Artificial Sequence
<220> FEATURE:

<223> OTHER INFORMATION: GFP variant fragment; sequence encoding
    fragment corresponding to B-strands 1-10

<400> SEQUENCE: 2

Met Ser Lys Gly Glu Glu Leu Phe Thr Gly Val Val Pro Ile Leu Val
1               5                   10                  15

Glu Leu Asp Gly Asp Val Asn Gly His Lys Phe Ser Val Arg Gly Glu
            20                  25                  30

Gly Glu Gly Asp Ala Thr Asn Gly Lys Leu Thr Leu Lys Phe Ile Cys
        35                  40                  45

Thr Thr Gly Lys Leu Pro Val Pro Trp Pro Thr Leu Val Thr Thr Leu
    50                  55                  60

Thr Tyr Gly Val Gln Cys Phe Ser Arg Tyr Pro Asp His Met Lys Arg
65                  70                  75                  80

His Asp Phe Phe Lys Ser Ala Met Pro Glu Gly Tyr Val Gln Glu Arg
                85                  90                  95

Thr Ile Ser Phe Lys Asp Asp Gly Thr Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
    130                 135                 140

Phe Asn Ser His Asn Val Tyr Ile Thr Ala Asp Lys Gln Lys Asn Gly
145                 150                 155                 160

Ile Lys Ala Asn Phe Lys Ile Arg His Asn Val Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Ser Val Leu Ser
        195                 200                 205

Lys Asp Pro Asn Glu Lys
    210

<210> SEQ ID NO 3
<211> LENGTH: 651
<212> TYPE: DNA
<213> ORGANISM: Artificial Sequence
<220> FEATURE:
<223> OTHER INFORMATION: GFP variant fragment; sequence encoding
    fragment corresponding to B-strands 1-10 OPT

<400> SEQUENCE: 3
atgagcaaag gagaagaact tttcactgga gttgtcccaa ttcttgttga attagatggt      60
gatgttaatg ggcacaaatt ttctgtcaga ggagagggtg aaggtgatgc tacaatcgga     120
aaactcaccc ttaaatttat ttgcactact ggaaaactac ctgttccatg gccaacactt     180
gtcactactc tgacctatgg tgttcaatgc ttttcccgtt atccggatca catgaaaagg     240
catgactttt tcaagagtgc catgcccgaa ggttatgtac aggaacgcac tatatctttc     300
aaagatgacg ggaaatacaa gacgcgtgct gtagtcaagt tgaaggtga tacccttgtt     360 aatcgtatcg agttaaaggg tactgatttt aaagaagatg gaaacattct cggacacaaa     420
ctcgagtaca actttaactc acacaatgta tacatcacgg cagacaaaca aaagaatgga     480
atcaaagcta acttcacagt tcgccacaac gttgaagatg gttccgttca actagcagac     540
cattatcaac aaaatactcc aattggcgat ggccctgtcc ttttaccaga caaccattac     600
ctgtcgacac aaactgtcct ttcgaaagat cccaacgaaa agggtaccta a              651

<210> SEQ ID NO 4
<211> LENGTH: 216
<212> TYPE: PRT
<213> ORGANISM: Artificial Sequence
<220> FEATURE:
<223> OTHER INFORMATION: GFP variant fragment; fragment corresponding to
    B -strands 1-10 OPT

<400> SEQUENCE: 4

Met Ser Lys Gly Glu Glu Leu Phe Thr Gly Val Val Pro Ile Leu Val
1               5                   10                  15

Glu Leu Asp Gly Asp Val Asn Gly His Lys Phe Ser Val Arg Gly Glu
            20                  25                  30

Gly Glu Gly Asp Ala Thr Ile Gly Lys Leu Thr Leu Lys Phe Ile Cys
        35                  40                  45

Thr Thr Gly Lys Leu Pro Val Pro Trp Pro Thr Leu Val Thr Thr Leu
    50                  55                  60

Thr Tyr Gly Val Gln Cys Phe Ser Arg Tyr Pro Asp His Met Lys Arg
65                  70                  75                  80

His Asp Phe Phe Lys Ser Ala Met Pro Glu Gly Tyr Val Gln Glu Arg
                85                  90                  95

Thr Ile Ser Phe Lys Asp Asp Gly Lys Tyr Lys Thr Arg Ala Val Val
            100                 105                 110

Lys Phe Glu Gly Asp Thr Leu Val Asn Arg Ile Glu Leu Lys Gly Thr
        115                 120                 125

Asp Phe Lys Glu Asp Gly Asn Ile Leu Gly His Lys Leu Glu Tyr Asn
    130                 135                 140

Phe Asn Ser His Asn Val Tyr Ile Thr Ala Asp Lys Gln Lys Asn Gly
145                 150                 155                 160

Ile Lys Ala Asn Phe Thr Val Arg His Asn Val Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Thr Val Leu Ser
        195                 200                 205

Lys Asp Pro Asn Glu Lys Gly Thr
    210                 215

<210> SEQ ID NO 5
<211> LENGTH: 651
<212> TYPE: DNA
<213> ORGANISM: Artificial Sequence
<220> FEATURE:
<223> OTHER INFORMATION: GFP variant fragment; sequence encoding
    fragment corresponding to B -strands 1-10 A4

<400> SEQUENCE: 5
atgagcaaag gagaagaact tttcactgga gttgtcccaa ttcttgttga attagatgga     60
gatgttaatg gcacaaaatt ttctgtcaga ggagagggtg aaggtgatgc tacaaacgga    120
aaactcaccc ttaaattcat ttgcactact ggaaaactac ctgttccatg gccaacgctt    180
gtcactactc tgacctatgg tgttcaatgc ttttcccgtt atccggatca catgaaacag    240
catgactttt tcaagagtgc catgcccgaa ggttatgtac aggaacgcac tatatatttc    300
aaagatgacg ggactacaa gacgcgtgct gtagtcaagt ttgaaggtga taccettgtt    360 aatcgtatcg agttaaaggg tactgatttt aagaagatg gaaacattct cggacacaaa    420

```
ctcgagtaca actttaactc acacaatgta tatatcacgg cagacaaaca aaagaatgga      480
atcaaagcta acttcacaat tcgccacaac gttgtagatg gttccgttca actagcagac      540
cattatcaac aaaatactcc aattggcgat ggccctgtcc ttttaccaga caaccattac      600
ttgtcgacac aaactgtcct ttcgaaagat cccaacgaaa agggtaccta a               651
```

<210> SEQ ID NO 6
<211> LENGTH: 216
<212> TYPE: PRT
<213> ORGANISM: Artificial Sequence
<220> FEATURE:
<223> OTHER INFORMATION: GFP variant fragment; fragment corresponding to
      B -strands 1-10 A4

<400> SEQUENCE: 6

```
Met Ser Lys Gly Glu Glu Leu Phe Thr Gly Val Val Pro Ile Leu Val
1               5                   10                  15

Glu Leu Asp Gly Asp Val Asn Gly His Lys Phe Ser Val Arg Gly Glu
            20                  25                  30

Gly Glu Gly Asp Ala Thr Asn Gly Lys Leu Thr Leu Lys Phe Ile Cys
        35                  40                  45

Thr Thr Gly Lys Leu Pro Val Pro Trp Pro Thr Leu Val Thr Thr Leu
    50                  55                  60

Thr Tyr Gly Val Gln Cys Phe Ser Arg Tyr Pro Asp His Met Lys Gln
65                  70                  75                  80

His Asp Phe Phe Lys Ser Ala Met Pro Glu Gly Tyr Val Gln Glu Arg
                85                  90                  95

Thr Ile Tyr Phe Lys Asp Asp Gly Asn Tyr Lys Thr Arg Ala Val Val
            100                 105                 110

Lys Phe Glu Gly Asp Thr Leu Val Asn Arg Ile Glu Leu Lys Gly Thr
        115                 120                 125

Asp Phe Lys Glu Asp Gly Asn Ile Leu Gly His Lys Leu Glu Tyr Asn
    130                 135                 140

Phe Asn Ser His Asn Val Tyr Ile Thr Ala Asp Lys Gln Lys Asn Gly
145                 150                 155                 160

Ile Lys Ala Asn Phe Thr Ile Arg His Asn Val Val Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Thr Val Leu Ser
        195                 200                 205

Lys Asp Pro Asn Glu Lys Gly Thr
    210                 215
```

<210> SEQ ID NO 7
<211> LENGTH: 84
<212> TYPE: DNA
<213> ORGANISM: Artificial Sequence
<220> FEATURE:
<223> OTHER INFORMATION: GFP variant fragment; sequence encoding
      fragment corresponding to B -strand 11, amino acids 214-238

<400> SEQUENCE: 7

```
aagcgtgacc acatggtcct tcttgagttt gtaactgctg ctgggattac acatggcatg      60
gatgagctct acaaaggtac ctaa                                             84
```

<210> SEQ ID NO 8
<211> LENGTH: 27

```
<212> TYPE: PRT
<213> ORGANISM: Artificial Sequence
<220> FEATURE:
<223> OTHER INFORMATION: GFP variant fragment; fragment corresponding to
      B -strand 11, amino acids 214-238

<400> SEQUENCE: 8

Lys Arg Asp His Met Val Leu Leu Glu Phe Val Thr Ala Ala Gly Ile
1               5                   10                  15

Thr His Gly Met Asp Glu Leu Tyr Lys Gly Thr
            20                  25

<210> SEQ ID NO 9
<211> LENGTH: 60
<212> TYPE: DNA
<213> ORGANISM: Artificial Sequence
<220> FEATURE:
<223> OTHER INFORMATION: GFP variant fragment; sequence encoding
      fragment corresponding to B -strand 11, amino acids 214-230

<400> SEQUENCE: 9
aagcgtgacc acatggtcct tcttgagttt gtaactgctg ctgggattac aggtacctaa    60

<210> SEQ ID NO 10
<211> LENGTH: 19
<212> TYPE: PRT
<213> ORGANISM: Artificial Sequence
<220> FEATURE:
<223> OTHER INFORMATION: GFP variant fragment; fragment corresponding to
      B -strand 11, amino acids 214-230

<400> SEQUENCE: 10

Lys Arg Asp His Met Val Leu Leu Glu Phe Val Thr Ala Ala Gly Ile
1               5                   10                  15

Thr Gly Thr

<210> SEQ ID NO 11
<211> LENGTH: 60
<212> TYPE: DNA
<213> ORGANISM: Artificial Sequence
<220> FEATURE:
<223> OTHER INFORMATION: GFP variant fragment; sequence encoding
      fragment corresponding to B -strand 11, M1 mutant

<400> SEQUENCE: 11
aagcgtgacc acatggtcct tcatgagttt gtaactgctg ctgggattac aggtacctaa    60

<210> SEQ ID NO 12
<211> LENGTH: 19
<212> TYPE: PRT
<213> ORGANISM: Artificial Sequence
<220> FEATURE:
<223> OTHER INFORMATION: GFP variant fragment; fragment corresponding to
      B -strand 11, M1 mutant

<400> SEQUENCE: 12

Lys Arg Asp His Met Val Leu His Glu Phe Val Thr Ala Ala Gly Ile
1               5                   10                  15

Thr Gly Thr

<210> SEQ ID NO 13
<211> LENGTH: 54
<212> TYPE: DNA
<213> ORGANISM: Artificial Sequence
<220> FEATURE:
<223> OTHER INFORMATION: GFP variant fragment; sequence encoding
``` fragment corresponding to B -strand 11, M2 mutant

<400> SEQUENCE: 13
aagcgtgacc acatggtcct tcatgagtct gtaaatgctg ctgggggtac ctaa    54

<210> SEQ ID NO 14
<211> LENGTH: 17
<212> TYPE: PRT
<213> ORGANISM: Artificial Sequence
<220> FEATURE:
<223> OTHER INFORMATION: GFP variant fragment; fragment corresponding to
      B -strand 11, M2 mutant

<400> SEQUENCE: 14

Lys Arg Asp His Met Val Leu His Glu Ser Val Asn Ala Ala Gly Gly
1               5                   10                  15

Thr

<210> SEQ ID NO 15
<211> LENGTH: 51
<212> TYPE: DNA
<213> ORGANISM: Artificial Sequence
<220> FEATURE:
<223> OTHER INFORMATION: GFP variant fragment; sequence encoding
      fragment corresponding to B -strand 11, M3 mutant

<400> SEQUENCE: 15
cgtgaccaca tggtccttca tgagtctgta aatgctgctg ggattacata a         51

<210> SEQ ID NO 16
<211> LENGTH: 16
<212> TYPE: PRT
<213> ORGANISM: Artificial Sequence
<220> FEATURE:
<223> OTHER INFORMATION: GFP variant fragment; fragment corresponding to
      B -strand 11, M3 mutant

<400> SEQUENCE: 16

Arg Asp His Met Val Leu His Glu Tyr Val Asn Ala Ala Gly Ile Thr
1               5                   10                  15

<210> SEQ ID NO 17
<211> LENGTH: 54
<212> TYPE: DNA
<213> ORGANISM: Artificial Sequence
<220> FEATURE:
<223> OTHER INFORMATION: GFP variant fragment; sequence encoding
      fragment corresponding to B -strand 11, H7 HIS-tag

<400> SEQUENCE: 17
aagcatgacc acatgcacct tcatgagcat gtacatgctc atgggggtac ctaa    54

<210> SEQ ID NO 18
<211> LENGTH: 17
<212> TYPE: PRT
<213> ORGANISM: Artificial Sequence
<220> FEATURE:
<223> OTHER INFORMATION: GFP variant fragment; fragment corresponding to
      B -strand 11, H7 HIS-tag

<400> SEQUENCE: 18

Lys His Asp His Met His Leu His Glu His Val His Ala His Gly Gly
1               5                   10                  15

Thr

<210> SEQ ID NO 19
<211> LENGTH: 51
<212> TYPE: DNA
<213> ORGANISM: Artificial Sequence
<220> FEATURE:
<223> OTHER INFORMATION: GFP variant fragment; sequence encoding
      fragment corresponding to B -strand 11, H9 HIS-tag

<400> SEQUENCE: 19
catgaccaca tgcaccttca tgagcatgta catgctcatc accatacctaa          51

<210> SEQ ID NO 20
<211> LENGTH: 16
<212> TYPE: PRT
<213> ORGANISM: Artificial Sequence
<220> FEATURE:
<223> OTHER INFORMATION: GFP variant fragment; fragment corresponding to
      B -strand 11, H9 HIS-tag

<400> SEQUENCE: 20

His Asp His Met His Leu His Glu His Val His Ala His His His Thr
1               5                   10                  15

<210> SEQ ID NO 21
<211> LENGTH: 1775
<212> TYPE: DNA
<213> ORGANISM: Artificial Sequence
<220> FEATURE:
<223> OTHER INFORMATION: Unique genetic elements of pTET-SpecR
      expression vector of SEQ ID NO: 22; elements from T0 to AatII:
      tet repressor protein tetR and spectinomycin gene under control of
      kanamycin promoter and RBS controlling expression of tet repressor

<400> SEQUENCE: 21

| | | | | | |
|---|---|---|---|---|---|
| ttaagaccca | ctttcacatt | taagttgttt | ttctaatccg | tatatgatca | attcaaggcc | 60 |
| gaataagaag | gctggctctg | caccttggtg | atcaaataat | tcgatagctt | gtcgtaataa | 120 |
| tggcggcata | ctatcagtag | taggtgtttc | cctttcttct | ttagcgactt | gatgctcttg | 180 |
| atcttccaat | acgcaaccta | agtaaaatg | ccccacagcg | ctgagtgcat | ataatgcatt | 240 |
| ctctagtgaa | aaaccttgtt | ggcataaaaa | ggctaattga | ttttcgagag | tttcatactg | 300 |
| tttttctgta | ggccgtgtac | ctaaatgtac | ttttgctcca | tcgcgatgac | ttagtaaagc | 360 |
| acatctaaaa | cttttagcgt | tattacgtaa | aaaatcttgc | cagctttccc | cttctaaagg | 420 |
| gcaaaagtga | gtatggtgcc | tatctaacat | ctcaatggct | aaggcgtcga | gcaaagcccg | 480 |
| cttatttttt | acatgccaat | acaatgtagg | ctgctctaca | cctagcttct | gggcgagttt | 540 |
| acgggttgtt | aaaccttcga | ttccgacctc | attaagcagc | tctaatgcgc | tgttaatcac | 600 |
| tttacttta | tctaatctgg | acatcattaa | tgtttattga | gctctcgaac | cccagagtcc | 660 |
| cgcattattt | gccgactacc | ttggtgatct | cgcctttcac | gtagtggaca | aattcttcca | 720 |
| actgatctgc | gcgcgaggcc | aagcgatctt | cttcttgtcc | aagataagcc | tgtctagctt | 780 |
| caagtatgac | gggctgatac | tgggccggca | ggcgctccat | tgcccagtcg | gcagcgacat | 840 |
| ccttcggcgc | gattttgccg | gttactgcgc | tgtaccaaat | gcgggacaac | gtaagcacta | 900 |
| catttcgctc | atcgccagcc | cagtcgggcg | gcgagttcca | tagcgttaag | gtttcattta | 960 |
| gcgcctcaaa | tagatcctgt | tcaggaaccg | gatcaaagag | ttcctccgcc | gctggaccta | 1020 |
| ccaaggcaac | gctatgttct | cttgcttttg | tcagcaagat | agccagatca | atgtcgatcg | 1080 |
| tggctggctc | gaagatacct | gcaagaatgt | cattgcgctg | ccattctcca | aattgcagtt | 1140 |
| cgcgcttagc | tggataacgc | cacggaatga | tgtcgtcgtg | cacaacaatg | gtgacttcta | 1200 |

```
cagcgcggag aatctcgctc tctccagggg aagccgaagt ttccaaaagg tcgttgatca   1260
aagctcgccg cgttgtttca tcaagcctta cggtcaccgt aaccagcaaa tcaatatcac   1320
tgtgtggctt caggccgcca tccactgcgg agccgtacaa atgtacggcc agcaacgtcg   1380
gttcgagatg gcgctcgatg acgccaacta cctctgatag ttgagtcgat acttcggcga   1440
tcaccgcttc cctcatgatg tttaactttg ttttagggcg actgccctgc tgcgtaacat   1500
cgttgctgct ccataacatc aaacatcgac ccacggcgta acgcgcttgc tgcttggatg   1560
cccgaggcat agactgtacc ccaaaaaaac atgtcataac aagccatgaa aaccgccact   1620
gcgccgttac catgcgaaac gatcctcatc ctgtctcttg atcagatctt gatccctgc    1680 gccatcagat ccttggcggc aagaaagcca tccagtttac tttgcagggc ttcccaacct   1740
taccagaggg cgccccagct ggcaattccg acgtc                              1775

<210> SEQ ID NO 22
<211> LENGTH: 3204
<212> TYPE: DNA
<213> ORGANISM: Artificial Sequence
<220> FEATURE:
<223> OTHER INFORMATION: Complete sequence of pTET-SpecR expression
      vector

<400> SEQUENCE: 22
tcgagtccct atcagtgata gagattgaca tccctatcag tgatagagat actgagcaca     60
tcagcaggac gcactgaccg agttcattaa agaggagaaa gatacccatg ggcagcagcc    120
atcatcatca tcatcacagc agcggcctgg tgccgcgcgg cagccatatg ggtggcggtt    180
ctggatccgg aggcactagt ggtggcggct caggtaccta actcgagcac caccaccacc    240
accactgaga tccggctgct aacaaagccc gaaaggaagc tgagttggct gctgccaccg    300
ctgagcaata actagcataa cctctagagg catcaaataa aacgaaaggc tcagtcgaaa    360
gactgggcct ttcgttttat ctgttgtttg tcggtgaacg ctctcctgag taggacaaat    420
ccgccgccct agacctaggc gttcggctgc ggcgagcggt atcagctcac tcaaaggcgg    480
taatacggtt atccacagaa tcaggggata acgcaggaaa gaacatgtga gcaaaaggcc    540
agcaaaaggc caggaaccgt aaaaaggccg cgttgctggc gtttttccat aggctccgcc    600
cccctgacga gcatcacaaa aatcgacgct caagtcagag gtggcgaaac ccgacaggac    660
tataaagata ccaggcgttt ccccctggaa gctccctcgt gcgctctcct gttccgaccc    720
tgccgcttac cggatacctg tccgcctttc tcccttcggg aagcgtggcg ctttctcaat    780
gctcacgctg taggtatctc agttcggtgt aggtcgttcg ctccaagctg gctgtgtgc    840 acgaaccccc cgttcagccc gaccgctgcg ccttatccgg taactatcgt cttgagtcca    900
acccggtaag acacgactta tcgccactgg cagcagccac tggtaacagg attagcagag    960
cgaggtatgt aggcggtgct acagagttct tgaagtggtg gcctaactac ggctacacta   1020
gaaggacagt atttggtatc tgcgctctgc tgaagccagt taccttcgga aaaagagttg   1080
gtagctcttg atccggcaaa caaaccaccg ctggtagcgg tggttttttt gtttgcaagc   1140
agcagattac gcgcagaaaa aaaggatctc aagaagatcc tttgatcttt tctacggggt   1200
ctgacgctca gtggaacgaa aactcacgtt aagggatttt ggtcatgact agcgcttgga   1260
ttctcaccaa taaaaaacgc ccggcggcaa ccgagcgttc tgaacaaatc cagatggagt   1320
tctgaggtca ttactggatc tatcaacagg agtccaagct taagacccac tttcacattt   1380
aagttgtttt tctaatccgt atatgatcaa ttcaaggccg aataagaagg ctggctctgc   1440
```

```
accttggtga tcaaataatt cgatagcttg tcgtaataat ggcggcatac tatcagtagt      1500
aggtgtttcc ctttcttctt tagcgacttg atgctcttga tcttccaata cgcaacctaa      1560
agtaaaatgc cccacagcgc tgagtgcata taatgcattc tctagtgaaa aaccttgttg      1620
gcataaaaag gctaattgat tttcgagagt ttcatactgt ttttctgtag gccgtgtacc      1680
taaatgtact tttgctccat cgcgatgact tagtaaagca catctaaaac ttttagcgtt      1740
attacgtaaa aaatcttgcc agctttcccc ttctaaaggg caaaagtgag tatggtgcct      1800
atctaacatc tcaatggcta aggcgtcgag caaagcccgc ttatttttta catgccaata      1860
caatgtaggc tgctctacac ctagcttctg ggcgagttta cgggttgtta aaccttcgat      1920
tccgacctca ttaagcagct ctaatgcgct gttaatcact ttacttttat ctaatctgga      1980
catcattaat gtttattgag ctctcgaacc ccagagtccc gcattatttg ccgactacct      2040
tggtgatctc gcctttcacg tagtggacaa attcttccaa ctgatctgcg cgcgaggcca      2100
agcgatcttc ttcttgtcca agataagcct gtctagcttc aagtatgacg ggctgatact      2160
gggccggcag gcgctccatt gcccagtcgg cagcgacatc cttcggcgcg attttgccgg      2220
ttactgcgct gtaccaaatg cgggacaacg taagcactac atttcgctca tcgccagccc      2280
agtcgggcgg cgagttccat agcgttaagg tttcatttag cgcctcaaat agatcctgtt      2340
caggaaccgg atcaaagagt tcctccgccg ctggacctac caaggcaacg ctatgttctc      2400
ttgcttttgt cagcaagata gccagatcaa tgtcgatcgt ggctggctcg aagatacctg      2460
caagaatgtc attgcgctgc cattctccaa attgcagttc gcgcttagct ggataacgcc      2520
acggaatgat gtcgtcgtgc acaacaatgg tgacttctac agcgcggaga atctcgctct      2580
ctccagggga agccgaagtt ccaaaaggt cgttgatcaa agctcgccgc gttgtttcat       2640
caagccttac ggtcaccgta accagcaaat caatatcact gtgtggcttc aggccgccat      2700
ccactgcgga gccgtacaaa tgtacggcca gcaacgtcgg ttcgagatgg cgctcgatga      2760
cgccaactac ctctgatagt tgagtcgata cttcggcgat caccgcttcc ctcatgatgt      2820
ttaactttgt tttagggcga ctgccctgct gcgtaacatc gttgctgctc ataacatca      2880 aacatcgacc cacggcgtaa cgcgcttgct gcttggatgc ccgaggcata gactgtaccc      2940
caaaaaaaca tgtcataaca agccatgaaa accgccactg cgccgttacc atgcgaaacg      3000
atcctcatcc tgtctcttga tcagatcttg atccctgcg ccatcagatc cttggcggca       3060
agaaagccat ccagtttact ttgcagggct tcccaacctt accagagggc gcccagctg       3120 gcaattccga cgtctaagaa accattatta tcatgacatt aacctataaa aataggcgta      3180
tcacgaggcc ctttcgtctt cacc                                             3204
```

<210> SEQ ID NO 23
<211> LENGTH: 596
<212> TYPE: DNA
<213> ORGANISM: Artificial Sequence
<220> FEATURE:
<223> OTHER INFORMATION: GFP variant fragment; sequence encoding
      fragment corresponding to B -strands 1-9 OPT

<400> SEQUENCE: 23

```
atgcgcaaag gagaagaact tttcactgga gttgtcccaa ttcttgttga attagatggt       60
gatgttaatg ggcacaaatt ttctgtccgt ggagagggtg aaggtgatgc tacaaacgga      120
aaactcagcc ttaaatttat ttgcactact ggaaaactac ctgttccatg gccaacactt      180
gtcactactc tgacctatgg tgttcaatgc ttttcccgtt atccggatca catgaaacgg      240
```

```
catgactttt tcaagagtgt catgcccgaa ggttatgtac aggaacgcac tatatctttc    300
aaagatgacg ggacctacaa gacgcgtgct gaagtcaagt ctgaaggtga taccctttgt    360
aatcgtatcg agttaaaagg tattgatttt aaagaagatg gaaacattct cggacacaaa    420
ctcgagtaca actttaactc acacaatgta tacatcacgg cagacaaaca aaagaatgga    480
atcaaagcta acttcacaat tcgccacaac gttgaagatg gttccgttca actagcagac    540
cattatcaac aaaatactcc aattggcgat ggccctgtcc ttttaccaga caataa        596
```

<210> SEQ ID NO 24
<211> LENGTH: 197
<212> TYPE: PRT
<213> ORGANISM: Artificial Sequence
<220> FEATURE:
<223> OTHER INFORMATION: GFP variant fragment; fragment corresponding to
      B -strands 1-9 OPT

<400> SEQUENCE: 24

```
Met Arg Lys Gly Glu Glu Leu Phe Thr Gly Val Val Pro Ile Leu Val
1               5                   10                  15

Glu Leu Asp Gly Asp Val Asn Gly His Lys Phe Ser Val Arg Gly Glu
            20                  25                  30

Gly Glu Gly Asp Ala Thr Asn Gly Lys Leu Ser Leu Lys Phe Ile Cys
        35                  40                  45

Thr Thr Gly Lys Leu Pro Val Pro Trp Pro Thr Leu Val Thr Thr Leu
    50                  55                  60

Thr Tyr Gly Val Gln Cys Phe Ser Arg Tyr Pro Asp His Met Lys Arg
65                  70                  75                  80

His Asp Phe Phe Lys Ser Val Met Pro Glu Gly Tyr Val Gln Glu Arg
                85                  90                  95

Thr Ile Ser Phe Lys Asp Asp Gly Thr Tyr Lys Thr Arg Ala Glu Val
            100                 105                 110

Lys Ser Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
    130                 135                 140

Phe Asn Ser His Asn Val Tyr Ile Thr Ala Asp Lys Gln Lys Asn Gly
145                 150                 155                 160

Ile Lys Ala Asn Phe Thr Ile Arg His Asn Val Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp
        195
```

<210> SEQ ID NO 25
<211> LENGTH: 41
<212> TYPE: PRT
<213> ORGANISM: Artificial Sequence
<220> FEATURE:
<223> OTHER INFORMATION: GFP variant fragment; fragment corresponding to
      B-strands 10-11 OPT

<400> SEQUENCE: 25

```
Asp His Tyr Leu Ser Thr Gln Thr Ile Leu Ser Lys Asp Pro Asn Glu
1               5                   10                  15

Glu Arg Asp His Met Val Leu Leu Glu Ser Val Thr Ala Ala Gly Ile
            20                  25                  30
```

Thr His Gly Met Asp Glu Leu Tyr Lys
        35                  40

<210> SEQ ID NO 26
<211> LENGTH: 71
<212> TYPE: PRT
<213> ORGANISM: Artificial Sequence
<220> FEATURE:
<223> OTHER INFORMATION: GFP variant fragment; fragment corresponding to
      B-strands 10-x-11 in sandwich configuration, optimum

<400> SEQUENCE: 26

Tyr Thr Met Asp Leu Pro Asp Asp His Tyr Leu Ser Thr Gln Thr Ile
1               5                   10                  15

Leu Ser Lys Asp Leu Asn Gly Thr Asp Val Gly Ser Gly Gly Gly Ser
            20                  25                  30

His Met Gly Gly Gly Ser Gly Ser Gly Gly Gly Ser Gly Gly Gly Ser
        35                  40                  45

Thr Ser Glu Lys Arg Asp His Met Val Leu Leu Glu Tyr Val Thr Ala
    50                  55                  60

Ala Gly Ile Thr Asp Ala Ser
65                  70

<210> SEQ ID NO 27
<211> LENGTH: 693
<212> TYPE: DNA
<213> ORGANISM: Artificial Sequence
<220> FEATURE:
<223> OTHER INFORMATION: Sequence encoding GFP variant "GFP 1-10 OPT M2"

<400> SEQUENCE: 27
atgagcaaag gagaagaact tttcactgga gttgtcccaa ttcttgttga attagatggt    60
gatgttaatg ggcacaaatt ttctgtcaga ggagagggtg aaggtgatgc tacaatcgga   120
aaactcaccc ttaaatttat ttgcactact ggaaaactac ctgttccatg gccaacactt   180
gtcactactc tgacctatgg tgttcaatgc ttttcccgtt atccggatca catgaaaagg   240
catgactttt tcaagagtgc catgcccgaa ggttatgtac aggaacgcac tatatctttc   300
aaagatgacg ggaaatacaa gacgcgtgct gtagtcaagt ttgaaggtga taccctgtt   360 aatcgtatcg agttaaaggg tactgatttt aagaagatg gaaacattct cggacacaaa   420
ctcgagtaca actttaactc acacaatgta tacatcacgg cagacaaaca aaagaatgga   480
atcaaagcta acttcacagt tcgccacaac gttgaagatg gttccgttca actagcagac   540
cattatcaac aaaatactcc aattggcgat ggccctgtcc ttttaccaga caaccattac   600
ctgtcgacac aaactgtcct ttcgaaagat cccaacgaaa agcgtgacca catggtcctt   660
catgagtctg taaatgctgc tgggattaca taa                                693

<210> SEQ ID NO 28
<211> LENGTH: 230
<212> TYPE: PRT
<213> ORGANISM: Artificial Sequence
<220> FEATURE:
<223> OTHER INFORMATION: GFP variant "GFP 1-10 OPT M2"

<400> SEQUENCE: 28

Met Ser Lys Gly Glu Glu Leu Phe Thr Gly Val Val Pro Ile Leu Val
1               5                   10                  15

Glu Leu Asp Gly Asp Val Asn Gly His Lys Phe Ser Val Arg Gly Glu
            20                  25                  30

-continued

```
Gly Glu Gly Asp Ala Thr Ile Gly Lys Leu Thr Leu Lys Phe Ile Cys
         35                  40                  45

Thr Thr Gly Lys Leu Pro Val Pro Trp Pro Thr Leu Val Thr Thr Leu
 50                  55                  60

Thr Tyr Gly Val Gln Cys Phe Ser Arg Tyr Pro Asp His Met Lys Arg
 65                  70                  75                  80

His Asp Phe Phe Lys Ser Ala Met Pro Glu Gly Tyr Val Gln Glu Arg
                 85                  90                  95

Thr Ile Ser Phe Lys Asp Asp Gly Lys Tyr Lys Thr Arg Ala Val Val
            100                 105                 110

Lys Phe Glu Gly Asp Thr Leu Val Asn Arg Ile Glu Leu Lys Gly Thr
        115                 120                 125

Asp Phe Lys Glu Asp Gly Asn Ile Leu Gly His Lys Leu Glu Tyr Asn
130                 135                 140

Phe Asn Ser His Asn Val Tyr Ile Thr Ala Asp Lys Gln Lys Asn Gly
145                 150                 155                 160

Ile Lys Ala Asn Phe Thr Val Arg His Asn Val Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Thr Val Leu Ser
        195                 200                 205

Lys Asp Pro Asn Glu Lys Arg Asp His Met Val Leu His Glu Ser Val
210                 215                 220

Asn Ala Ala Gly Ile Thr
225                 230
```

<210> SEQ ID NO 29
<211> LENGTH: 717
<212> TYPE: DNA
<213> ORGANISM: Artificial Sequence
<220> FEATURE:
<223> OTHER INFORMATION: Sequence encoding GFP variant "GFP 1-10 OPT M2 tailed"

<400> SEQUENCE: 29

```
atgagcaaag gagaagaact tttcactgga gttgtcccaa ttcttgttga attagatggt    60
gatgttaatg ggcacaaatt ttctgtcaga ggagagggtg aaggtgatgc tacaatcgga   120
aaactcaccc ttaaatttat ttgcactact ggaaaactac ctgttccatg gccaacactt   180
gtcactactc tgacctatgg tgttcaatgc ttttcccgtt atccggatca catgaaaagg   240
catgactttt tcaagagtgc catgcccgaa ggttatgtac aggaacgcac tatatctttc   300
aaagatgacg ggaaatacaa gacgcgtgct gtagtcaagt tgaaggtga taccttgtt    360
aatcgtatcg agttaaaggg tactgatttt aaagaagatg gaaacattct cggacacaaa   420
ctcgagtaca cttaactc acacaatgta tacatcacgg cagacaaaca aaagaatgga    480
atcaaagcta acttcacagt tcgccacaac gttgaagatg gttccgttca actagcagac   540
cattatcaac aaaatactcc aattggcgat ggccctgtcc ttttaccaga caaccattac   600
ctgtcgacac aaactgtcct ttcgaaagat cccaacgaaa agcgtgacca catggtcctt   660
catgagtctg taaatgctgc tgggattaca catggcatgg atgagctcta caaataa     717
```

<210> SEQ ID NO 30
<211> LENGTH: 238
<212> TYPE: PRT
<213> ORGANISM: Artificial Sequence
<220> FEATURE:
<223> OTHER INFORMATION: GFP variant "GFP 1-10 OPT M2 tailed"

<400> SEQUENCE: 30

```
Met Ser Lys Gly Glu Glu Leu Phe Thr Gly Val Val Pro Ile Leu Val
1               5                   10                  15

Glu Leu Asp Gly Asp Val Asn Gly His Lys Phe Ser Val Arg Gly Glu
            20                  25                  30

Gly Glu Gly Asp Ala Thr Ile Gly Lys Leu Thr Leu Lys Phe Ile Cys
        35                  40                  45

Thr Thr Gly Lys Leu Pro Val Pro Trp Pro Thr Leu Val Thr Thr Leu
    50                  55                  60

Thr Tyr Gly Val Gln Cys Phe Ser Arg Tyr Pro Asp His Met Lys Arg
65                  70                  75                  80

His Asp Phe Phe Lys Ser Ala Met Pro Glu Gly Tyr Val Gln Glu Arg
                85                  90                  95

Thr Ile Ser Phe Lys Asp Asp Gly Lys Tyr Lys Thr Arg Ala Val Val
            100                 105                 110

Lys Phe Glu Gly Asp Thr Leu Val Asn Arg Ile Glu Leu Lys Gly Thr
        115                 120                 125

Asp Phe Lys Glu Asp Gly Asn Ile Leu Gly His Lys Leu Glu Tyr Asn
    130                 135                 140

Phe Asn Ser His Asn Val Tyr Ile Thr Ala Asp Lys Gln Lys Asn Gly
145                 150                 155                 160

Ile Lys Ala Asn Phe Thr Val Arg His Asn Val Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Thr Val Leu Ser
        195                 200                 205

Lys Asp Pro Asn Glu Lys Arg Asp His Met Val Leu His Glu Ser Val
    210                 215                 220

Asn Ala Ala Gly Ile Thr His Gly Met Asp Glu Leu Tyr Lys
225                 230                 235
```

<210> SEQ ID NO 31
<211> LENGTH: 124
<212> TYPE: DNA
<213> ORGANISM: Artificial Sequence
<220> FEATURE:
<223> OTHER INFORMATION: GFP variant fragment; sequence encoding
      fragment corresponding to B-strands 10-11 OPT

<400> SEQUENCE: 31

```
gaccattacc tgtcgacaca aactatcctt tcgaaagatc ccaacgaaga gcgtgaccac    60
atggtccttc ttgagtctgt aactgctgct gggattacac atggcatgga tgagctctac   120
aaat                                                                 124
```

<210> SEQ ID NO 32
<211> LENGTH: 230
<212> TYPE: DNA
<213> ORGANISM: Artificial Sequence
<220> FEATURE:
<223> OTHER INFORMATION: GFP variant fragment; sequence encoding
      fragment corresponding to B-strands 10-x-11 in sandwich
      configuration, optimum

<400> SEQUENCE: 32

```
gatataccat ggatttacca gacgaccatt acctgtcgac acaaactatc ctttcgaaag      60
atctcaacgg taccgacgtt gggtctggcg gtggctccca tgggtggc ggttctggat      120 ccggtggagg gtctggtggc ggatcaacta gtgaaaagcg tgaccacatg gtccttcttg    180
agtatgtaac tgctgctggg attacagatg ctagctaact cgagaatagc                230
```

<210> SEQ ID NO 33
<211> LENGTH: 693
<212> TYPE: DNA
<213> ORGANISM: Artificial Sequence
<220> FEATURE:
<223> OTHER INFORMATION: GFP variant; sequence encoding "GFP 1-10 OPT M3"

<400> SEQUENCE: 33

```
atgagcaaag gagaagaact tttcactgga gttgtcccaa ttcttgttga attagatggt    60
gatgttaatg gcacaaaatt ttctgtcaga ggagagggtg aaggtgatgc tacaatcgga   120
aaactcaccc ttaaatttat ttgcactact ggaaaactac ctgttccatg gccaacactt   180
gtcactactc tgacctatgg tgttcaatgc ttttcccgtt atccggatca catgaaaagg   240
catgactttt tcaagagtgc catgcccgaa ggttatgtac aggaacgcac tatatctttc   300
aaagatgacg ggaaatacaa gacgcgtgct gtagtcaagt ttgaaggtga tacccttgtt   360
aatcgtatcg agttaaaggg tactgatttt aaagaagatg gaaacattct cggacacaaa   420
ctcgagtaca actttaactc acacaatgta tacatcacgg cagacaaaca aaagaatgga   480
atcaaagcta acttcacagt tcgccacaac gttgaagatg gttccgttca actagcagac   540
cattatcaac aaaatactcc aattggcgat ggccctgtcc ttttaccaga caaccattac   600
ctgtcgacac aaactgtcct ttcgaaagat cccaacgaaa agcgtgacca catggtcctt   660
catgagtacg taaatgctgc tgggattaca taa                                693
```

<210> SEQ ID NO 34
<211> LENGTH: 230
<212> TYPE: PRT
<213> ORGANISM: Artificial Sequence
<220> FEATURE:
<223> OTHER INFORMATION: GFP variant "GFP 1-10 OPT M3"

<400> SEQUENCE: 34

```
Met Ser Lys Gly Glu Glu Leu Phe Thr Gly Val Val Pro Ile Leu Val
1               5                   10                  15

Glu Leu Asp Gly Asp Val Asn Gly His Lys Phe Ser Val Arg Gly Glu
            20                  25                  30

Gly Glu Gly Asp Ala Thr Ile Gly Lys Leu Thr Leu Lys Phe Ile Cys
        35                  40                  45

Thr Thr Gly Lys Leu Pro Val Pro Trp Pro Thr Leu Val Thr Thr Leu
    50                  55                  60

Thr Tyr Gly Val Gln Cys Phe Ser Arg Tyr Pro Asp His Met Lys Arg
65                  70                  75                  80

His Asp Phe Phe Lys Ser Ala Met Pro Glu Gly Tyr Val Gln Glu Arg
                85                  90                  95

Thr Ile Ser Phe Lys Asp Asp Gly Lys Tyr Lys Thr Arg Ala Val Val
            100                 105                 110

Lys Phe Glu Gly Asp Thr Leu Val Asn Arg Ile Glu Leu Lys Gly Thr
        115                 120                 125

Asp Phe Lys Glu Asp Gly Asn Ile Leu Gly His Lys Leu Glu Tyr Asn
    130                 135                 140
```

```
Phe Asn Ser His Asn Val Tyr Ile Thr Ala Asp Lys Gln Lys Asn Gly
145                 150                 155                 160

Ile Lys Ala Asn Phe Thr Val Arg His Asn Val Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Thr Val Leu Ser
        195                 200                 205

Lys Asp Pro Asn Glu Lys Arg Asp His Met Val Leu His Glu Tyr Val
    210                 215                 220

Asn Ala Ala Gly Ile Thr
225                 230

<210> SEQ ID NO 35
<211> LENGTH: 717
<212> TYPE: DNA
<213> ORGANISM: Artificial Sequence
<220> FEATURE:
<223> OTHER INFORMATION: GFP variant; sequence encoding "GFP 1-10 OPT M3
      tailed"

<400> SEQUENCE: 35
atgagcaaag gagaagaact tttcactgga gttgtcccaa ttcttgttga attagatggt      60
gatgttaatg ggcacaaatt ttctgtcaga ggagagggtg aaggtgatgc tacaatcgga    120
aaactcaccc ttaaatttat ttgcactact ggaaaactac ctgttccatg gccaacactt    180
gtcactactc tgacctatgg tgttcaatgc ttttcccgtt atccggatca catgaaaagg    240
catgactttt tcaagagtgc catgcccgaa ggttatgtac aggaacgcac tatatctttc    300
aaagatgacg ggaaatacaa gacgcgtgct gtagtcaagt ttgaaggtga tacccttgtt    360
aatcgtatcg agttaaaggg tactgatttt aaagaagatg gaaacattct cggacacaaa    420
ctcgagtaca actttaactc acacaatgta tacatcacgg cagacaaaca aaagaatgga    480
atcaaagcta acttcacagt tcgccacaac gttgaagatg gttccgttca actagcagac    540
cattatcaac aaaatactcc aattggcgat ggccctgtcc ttttaccaga caaccattac    600
ctgtcgacac aaactgtcct ttcgaaagat cccaacgaaa agcgtgacca catggtcctt    660
catgagtacg taaatgctgc tgggattaca catggcatgg atgagctcta caaataa       717

<210> SEQ ID NO 36
<211> LENGTH: 238
<212> TYPE: PRT
<213> ORGANISM: Artificial Sequence
<220> FEATURE:
<223> OTHER INFORMATION: GFP variant "GFP 1-10 OPT M3 tailed"

<400> SEQUENCE: 36

Met Ser Lys Gly Glu Glu Leu Phe Thr Gly Val Val Pro Ile Leu Val
1               5                   10                  15

Glu Leu Asp Gly Asp Val Asn Gly His Lys Phe Ser Val Arg Gly Glu
            20                  25                  30

Gly Glu Gly Asp Ala Thr Ile Gly Lys Leu Thr Leu Lys Phe Ile Cys
        35                  40                  45

Thr Thr Gly Lys Leu Pro Val Pro Trp Pro Thr Leu Val Thr Thr Leu
    50                  55                  60

Thr Tyr Gly Val Gln Cys Phe Ser Arg Tyr Pro Asp His Met Lys Arg
65                  70                  75                  80
```

```
His Asp Phe Phe Lys Ser Ala Met Pro Glu Gly Tyr Val Gln Glu Arg
                85                  90                  95

Thr Ile Ser Phe Lys Asp Asp Gly Lys Tyr Lys Thr Arg Ala Val Val
            100                 105                 110

Lys Phe Glu Gly Asp Thr Leu Val Asn Arg Ile Glu Leu Lys Gly Thr
        115                 120                 125

Asp Phe Lys Glu Asp Gly Asn Ile Leu Gly His Lys Leu Glu Tyr Asn
    130                 135                 140

Phe Asn Ser His Asn Val Tyr Ile Thr Ala Asp Lys Gln Lys Asn Gly
145                 150                 155                 160

Ile Lys Ala Asn Phe Thr Val Arg His Asn Val Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Thr Val Leu Ser
        195                 200                 205

Lys Asp Pro Asn Glu Lys Arg Asp His Met Val Leu His Glu Tyr Val
    210                 215                 220

Asn Ala Ala Gly Ile Thr His Gly Met Asp Glu Leu Tyr Lys
225                 230                 235

<210> SEQ ID NO 37
<211> LENGTH: 28
<212> TYPE: PRT
<213> ORGANISM: Polyomavirus SV-40
<220> FEATURE:
<221> NAME/KEY: misc_feature
<223> OTHER INFORMATION: siman virus 40 large T antigen nuclear
      localization signal

<400> SEQUENCE: 37

Ser Lys Lys Glu Glu Lys Gly Arg Ser Lys Lys Glu Glu Lys Gly Arg
1               5                   10                  15

Ser Lys Lys Glu Glu Lys Gly Arg Ile His Arg Ile
            20                  25

<210> SEQ ID NO 38
<211> LENGTH: 87
<212> TYPE: DNA
<213> ORGANISM: Polyomavirus SV-40
<220> FEATURE:
<221> NAME/KEY: misc_feature
<223> OTHER INFORMATION: sequence encoding siman virus 40 large T
      antigen nuclear localization signal

<400> SEQUENCE: 38
tccaaaaaag aagagaaagg tagatccaaa aaagaagaga aggtagatc caaaaaagaa    60 gagaaaggta ggatccaccg gatctag                                      87

<210> SEQ ID NO 39
<211> LENGTH: 89
<212> TYPE: PRT
<213> ORGANISM: Homo sapiens
<220> FEATURE:
<221> NAME/KEY: misc_feature
<223> OTHER INFORMATION: N-terminal 89 amino acids of human beta 1,
      4-galactosyltransferase

<400> SEQUENCE: 39

Met Arg Leu Arg Glu Pro Leu Leu Ser Gly Ser Ala Ala Met Pro Gly
1               5                   10                  15
```

```
Ala Ser Leu Gln Arg Ala Cys Arg Leu Leu Val Ala Val Cys Ala Leu
         20                  25                  30

His Leu Gly Val Thr Leu Val Tyr Tyr Leu Ala Gly Arg Asp Leu Ser
             35                  40                  45

Arg Leu Pro Gln Leu Val Gly Val Ser Thr Pro Leu Gln Gly Gly Ser
     50                  55                  60

Asn Ser Ala Ala Ala Ile Gly Gln Ser Ser Gly Glu Leu Arg Thr Gly
65                  70                  75                  80

Gly Ala Lys Asp Pro Pro Val Ala Thr
                 85
```

```
<210> SEQ ID NO 40
<211> LENGTH: 267
<212> TYPE: DNA
<213> ORGANISM: Homo sapiens
<220> FEATURE:
<221> NAME/KEY: misc_feature
<223> OTHER INFORMATION: Sequence encoding N-terminal 89 amino acids of
      human beta 1,4-galactosyltransferase

<400> SEQUENCE: 40
atgaggcttc gggagccgct cctgagcggc agcgccgcga tgccaggcgc gtccctacag     60
cgggcctgcc gcctgctcgt ggccgtctgc gctctgcacc ttggcgtcac cctcgtttac    120
tacctggctg gccgcgacct gagccgcctg ccccaactgg tcggagtctc cacaccgctg    180
cagggcggct cgaacagtgc cgccgccatc gggcagtcct ccggggagct ccggaccgga    240
ggggccaagg atccaccggt cgccacc                                         267

<210> SEQ ID NO 41
<211> LENGTH: 36
<212> TYPE: PRT
<213> ORGANISM: Homo sapiens
<220> FEATURE:
<221> NAME/KEY: misc_feature
<223> OTHER INFORMATION: mitochondrial targeting sequence derived from
      the precursor of subunit VIII of human cytochrome C oxidase

<400> SEQUENCE: 41

Met Ser Val Leu Thr Pro Leu Leu Leu Arg Gly Leu Thr Gly Ser Ala
1               5                   10                  15

Arg Arg Leu Pro Val Pro Arg Ala Lys Ile His Ser Leu Gly Asp Pro
             20                  25                  30

Pro Val Ala Thr
         35

<210> SEQ ID NO 42
<211> LENGTH: 108
<212> TYPE: DNA
<213> ORGANISM: Homo sapiens
<220> FEATURE:
<221> NAME/KEY: misc_feature
<223> OTHER INFORMATION: Sequence encoding mitochondrial targeting
      sequence derived from the precursor of subunit VIII of human
      cytochrome C oxidase

<400> SEQUENCE: 42
atgtccgtcc tgacgccgct gctgctgcgg ggcttgacag gctcggcccg gcggctccca     60
gtgccgcgcg ccaagatcca ttcgttgggg gatccaccgg tcgccacc                 108

<210> SEQ ID NO 43
<211> LENGTH: 18
<212> TYPE: PRT
```

```
<213> ORGANISM: Homo sapiens
<220> FEATURE:
<221> NAME/KEY: misc_feature
<223> OTHER INFORMATION: ER targeting sequence of calreticulin

<400> SEQUENCE: 43

Met Leu Leu Ser Val Pro Leu Leu Leu Gly Leu Leu Gly Leu Ala Val
1               5                   10                  15

Ala Val

<210> SEQ ID NO 44
<211> LENGTH: 54
<212> TYPE: DNA
<213> ORGANISM: Homo sapiens
<220> FEATURE:
<221> NAME/KEY: misc_feature
<223> OTHER INFORMATION: Sequence encoding ER targeting sequence of
      calreticulin

<400> SEQUENCE: 44
atgctgctat ccgtgccgtt gctgctcggc ctcctcggcc tggccgtcgc cgtg            54

<210> SEQ ID NO 45
<211> LENGTH: 39
<212> TYPE: DNA
<213> ORGANISM: Artificial Sequence
<220> FEATURE:
<223> OTHER INFORMATION: Synthetic primer sequence

<400> SEQUENCE: 45
taagaaggag atataatggt cctgacgccg ctgctgctg                             39

<210> SEQ ID NO 46
<211> LENGTH: 39
<212> TYPE: DNA
<213> ORGANISM: Artificial Sequence
<220> FEATURE:
<223> OTHER INFORMATION: Synthetic primer sequence

<400> SEQUENCE: 46
cagcagcggc gtcaggacca ttatatctcc ttcttaaag                             39

<210> SEQ ID NO 47
<211> LENGTH: 33
<212> TYPE: DNA
<213> ORGANISM: Artificial Sequence
<220> FEATURE:
<223> OTHER INFORMATION: Synthetic primer sequence

<400> SEQUENCE: 47
ggcgaccggt gggtccccca acgaatggat ctt                                   33

<210> SEQ ID NO 48
<211> LENGTH: 42
<212> TYPE: DNA
<213> ORGANISM: Artificial Sequence
<220> FEATURE:
<223> OTHER INFORMATION: Synthetic primer sequence

<400> SEQUENCE: 48
ctatatcata tgagaaccgc caccggtggc gaccggtggg tc                         42

<210> SEQ ID NO 49
<211> LENGTH: 4
<212> TYPE: PRT
<213> ORGANISM: Artificial Sequence
```

```
<220> FEATURE:
<223> OTHER INFORMATION: Polypeptide linker

<400> SEQUENCE: 49

Gly Gly Gly Ser
1

<210> SEQ ID NO 50
<211> LENGTH: 33
<212> TYPE: DNA
<213> ORGANISM: Artificial Sequence
<220> FEATURE:
<223> OTHER INFORMATION: Synthetic primer sequence

<400> SEQUENCE: 50
ggcggttctt ccaaaaaaga agagaaaggt aga                                  33

<210> SEQ ID NO 51
<211> LENGTH: 36
<212> TYPE: DNA
<213> ORGANISM: Artificial Sequence
<220> FEATURE:
<223> OTHER INFORMATION: Synthetic primer sequence

<400> SEQUENCE: 51
gatataggat ccggtggcgg ttcttccaaa aaagaa                               36

<210> SEQ ID NO 52
<211> LENGTH: 33
<212> TYPE: DNA
<213> ORGANISM: Artificial Sequence
<220> FEATURE:
<223> OTHER INFORMATION: Synthetic primer sequence

<400> SEQUENCE: 52
ttagatccgg tgtatcctac ctttctcttc ttt                                  33

<210> SEQ ID NO 53
<211> LENGTH: 33
<212> TYPE: DNA
<213> ORGANISM: Artificial Sequence
<220> FEATURE:
<223> OTHER INFORMATION: Synthetic primer sequence

<400> SEQUENCE: 53
ctatatctcg agttagatcc ggtgtatcct acc                                  33

<210> SEQ ID NO 54
<211> LENGTH: 4
<212> TYPE: PRT
<213> ORGANISM: Artificial Sequence
<220> FEATURE:
<223> OTHER INFORMATION: Endoplasmic reticulum localization peptide

<400> SEQUENCE: 54

Lys Asp Glu Leu
1

<210> SEQ ID NO 55
<211> LENGTH: 37
<212> TYPE: DNA
<213> ORGANISM: Artificial Sequence
<220> FEATURE:
<223> OTHER INFORMATION: Synthetic primer sequence

<400> SEQUENCE: 55
```

```
taagaaggag atataatgct gctatccgtg ccgttgc                              37
```

<210> SEQ ID NO 56
<211> LENGTH: 36
<212> TYPE: DNA
<213> ORGANISM: Artificial Sequence
<220> FEATURE:
<223> OTHER INFORMATION: Synthetic primer sequence

<400> SEQUENCE: 56

```
cggcacggat agcagcatta tatctccttc ttaaag                               36
```

<210> SEQ ID NO 57
<211> LENGTH: 39
<212> TYPE: DNA
<213> ORGANISM: Artificial Sequence
<220> FEATURE:
<223> OTHER INFORMATION: Synthetic primer sequence

<400> SEQUENCE: 57

```
gatataggta ccggtggcgg ttctcaccac caccaccac                            39
```

<210> SEQ ID NO 58
<211> LENGTH: 33
<212> TYPE: DNA
<213> ORGANISM: Artificial Sequence
<220> FEATURE:
<223> OTHER INFORMATION: Synthetic primer sequence

<400> SEQUENCE: 58

```
tctcaccacc accaccacca cggtggcggt tct                                  33
```

<210> SEQ ID NO 59
<211> LENGTH: 33
<212> TYPE: DNA
<213> ORGANISM: Artificial Sequence
<220> FEATURE:
<223> OTHER INFORMATION: Synthetic primer sequence

<400> SEQUENCE: 59

```
cagctcgtcc ttagaaccgc caccgtggtg gtg                                  33
```

<210> SEQ ID NO 60
<211> LENGTH: 39
<212> TYPE: DNA
<213> ORGANISM: Artificial Sequence
<220> FEATURE:
<223> OTHER INFORMATION: Synthetic primer sequence

<400> SEQUENCE: 60

```
ctatatctcg agttacagct cgtccttaga accgccacc                            39
```

<210> SEQ ID NO 61
<211> LENGTH: 585
<212> TYPE: DNA
<213> ORGANISM: Artificial Sequence
<220> FEATURE:
<223> OTHER INFORMATION: Sequence encoding MTS-SR-s11-6his fusion
      polypeptide

<400> SEQUENCE: 61

```
atgtccgtcc tgacgccgct gctgctgcgg ggcttgacag gctcggcccg gcggctccca      60
gtgccgcgcg ccaagatcca ttcgttgggg gacccaccgg tcgccaccgg tggcggttct     120
catatgccag tgaaatgtcc cggcgagtac caagttgatg caaaaaagt tatactagac      180
```

```
gaggactgtt ttatgcaaaa cccagaggac tgggacgaaa aagtggctga gtggttggcc      240
agagagctag agggcataca aaaaatgacc gaggagcatt ggaagttggt aaaatactta      300
agggagtatt gggagacctt cggctcctgc ccgccaatta aaatggtcac taaagagacg      360
ggcttctcct tggagaaaat ctaccagcta ttccctcgg ggcctgcgca cggagcttgt       420
aaagtggcag gcgcgccgaa gcccacaggc tgcgtcggat ccgatggagg gtctggtggc      480
ggatcaacaa gccgtgacca catggtcctt catgagtacg taaatgctgc tgggattaca      540
ggtaccggtg gcggttctct cgagcaccac caccaccacc actga                     585
```

<210> SEQ ID NO 62
<211> LENGTH: 194
<212> TYPE: PRT
<213> ORGANISM: Artificial Sequence
<220> FEATURE:
<223> OTHER INFORMATION: MTS-SR-s11-6his fusion polypeptide

<400> SEQUENCE: 62

```
Met Ser Val Leu Thr Pro Leu Leu Leu Arg Gly Leu Thr Gly Ser Ala
1               5                   10                  15

Arg Arg Leu Pro Val Pro Arg Ala Lys Ile His Ser Leu Gly Asp Pro
            20                  25                  30

Pro Val Ala Thr Gly Gly Gly Ser His Met Pro Val Lys Cys Pro Gly
        35                  40                  45

Glu Tyr Gln Val Asp Gly Lys Lys Val Ile Leu Asp Glu Asp Cys Phe
    50                  55                  60

Met Gln Asn Pro Glu Asp Trp Asp Glu Lys Val Ala Glu Trp Leu Ala
65                  70                  75                  80

Arg Glu Leu Glu Gly Ile Gln Lys Met Thr Glu Glu His Trp Lys Leu
                85                  90                  95

Val Lys Tyr Leu Arg Glu Tyr Trp Glu Thr Phe Gly Ser Cys Pro Pro
            100                 105                 110

Ile Lys Met Val Thr Lys Glu Thr Gly Phe Ser Leu Glu Lys Ile Tyr
        115                 120                 125

Gln Leu Phe Pro Ser Gly Pro Ala His Gly Ala Cys Lys Val Ala Gly
    130                 135                 140

Ala Pro Lys Pro Thr Gly Cys Val Gly Ser Asp Gly Gly Ser Gly Gly
145                 150                 155                 160

Gly Ser Thr Ser Arg Asp His Met Val Leu His Glu Tyr Val Asn Ala
                165                 170                 175

Ala Gly Ile Thr Gly Thr Gly Gly Gly Ser Leu Glu His His His
            180                 185                 190

His His
```

<210> SEQ ID NO 63
<211> LENGTH: 819
<212> TYPE: DNA
<213> ORGANISM: Artificial Sequence
<220> FEATURE:
<223> OTHER INFORMATION: Sequence encoding MTS-(1-10)opt-6his fusion
      polypeptide

<400> SEQUENCE: 63

```
atgtccgtcc tgacgccgct gctgctgcgg ggcttgacag gctcggcccg gcggctccca      60
gtgccgcgcg ccaagatcca ttcgttgggg gacccaccgg tcgccaccgg tggcggttct     120
catatgatga gcaaaggaga agaactttt actggagttg tcccaattct tgttgaatta      180
```

```
gatggtgatg ttaatgggca caaatttct gtcagaggag agggtgaagg tgatgctaca    240
atcggaaaac tcacccttaa atttatttgc actactggaa aactacctgt tccatggcca    300
acacttgtca ctactctgac ctatggtgtt caatgctttt cccgttatcc ggatcacatg    360
aaaaggcatg acttttcaa gagtgccatg cccgaaggtt atgtacagga acgcactata    420
tctttcaaag atgacgggaa atacaagacg cgtgctgtag tcaagtttga aggtgatacc    480
cttgttaatc gtatcgagtt aaagggtact gattttaaag aagatggaaa cattctcgga    540
cacaaactcg agtacaactt taactcacac aatgtataca tcacggcaga caaacaaaag    600
aatggaatca aagctaactt cacagttcgc cacaacgttg aagatggttc cgttcaacta    660
gcagaccatt atcaacaaaa tactccaatt ggcgatggcc ctgtcctttt accagacaac    720
cattacctgt cgacacaaac tgtcctttcg aaagatccca acgaaaaggg taccggtacc    780
ggtggcggtt ctctcgagca ccaccaccac caccactga                          819
```

<210> SEQ ID NO 64
<211> LENGTH: 272
<212> TYPE: PRT
<213> ORGANISM: Artificial Sequence
<220> FEATURE:
<223> OTHER INFORMATION: MTS-(1-10)opt-6his fusion polypeptide

<400> SEQUENCE: 64

```
Met Ser Val Leu Thr Pro Leu Leu Arg Gly Leu Thr Gly Ser Ala
1               5                   10                  15

Arg Arg Leu Pro Val Pro Arg Ala Lys Ile His Ser Leu Gly Asp Pro
            20                  25                  30

Pro Val Ala Thr Gly Gly Gly Ser His Met Met Ser Lys Gly Glu Glu
        35                  40                  45

Leu Phe Thr Gly Val Val Pro Ile Leu Val Glu Leu Asp Gly Asp Val
    50                  55                  60

Asn Gly His Lys Phe Ser Val Arg Gly Glu Gly Glu Gly Asp Ala Thr
65                  70                  75                  80

Ile Gly Lys Leu Thr Leu Lys Phe Ile Cys Thr Thr Gly Lys Leu Pro
                85                  90                  95

Val Pro Trp Pro Thr Leu Val Thr Thr Leu Thr Tyr Gly Val Gln Cys
            100                 105                 110

Phe Ser Arg Tyr Pro Asp His Met Lys Arg His Asp Phe Phe Lys Ser
        115                 120                 125

Ala Met Pro Glu Gly Tyr Val Gln Glu Arg Thr Ile Ser Phe Lys Asp
    130                 135                 140

Asp Gly Lys Tyr Lys Thr Arg Ala Val Val Lys Phe Glu Gly Asp Thr
145                 150                 155                 160

Leu Val Asn Arg Ile Glu Leu Lys Gly Thr Asp Phe Lys Glu Asp Gly
                165                 170                 175

Asn Ile Leu Gly His Lys Leu Glu Tyr Asn Phe Asn Ser His Asn Val
            180                 185                 190

Tyr Ile Thr Ala Asp Lys Gln Lys Asn Gly Ile Lys Ala Asn Phe Thr
        195                 200                 205

Val Arg His Asn Val Glu Asp Gly Ser Val Gln Leu Ala Asp His Tyr
    210                 215                 220

Gln Gln Asn Thr Pro Ile Gly Asp Gly Pro Val Leu Leu Pro Asp Asn
225                 230                 235                 240

His Tyr Leu Ser Thr Gln Thr Val Leu Ser Lys Asp Pro Asn Glu Lys
                245                 250                 255
```

```
Gly Thr Gly Thr Gly Gly Gly Ser Leu Glu His His His His His
            260                 265                 270

<210> SEQ ID NO 65
<211> LENGTH: 492
<212> TYPE: DNA
<213> ORGANISM: Artificial Sequence
<220> FEATURE:
<223> OTHER INFORMATION: Sequence of receiving vector for nuclear
      localization

<400> SEQUENCE: 65
atgggccacc accaccacca ccacggtggc ggttctacta gtcgtgacca catggtcctt    60
catgagtacg taaatgctgc tgggattaca ggtaccgatg agggtctgg tggcggatca    120 catatgccag tgaaatgtcc cggcgagtac caagttgatg gcaaaaaagt tatactagac    180
gaggactgtt ttatgcaaaa cccagaggac tgggacgaaa aagtggctga gtggttggcc    240
agagagctag agggcataca aaaaatgacc gaggagcatt ggaagttggt aaaatactta    300
agggagtatt gggagacctt cggctcctgc ccgccaatta aaatggtcac taaagagacg    360
ggcttctcct tggagaaaat ctaccagcta ttccctcgg ggcctgcgca cggagcttgt    420
aaagtggcag gcgcgccgaa gcccacaggc tgcgtcggat cctaactcga gcaccaccac    480
caccaccact ga                                                       492

<210> SEQ ID NO 66
<211> LENGTH: 162
<212> TYPE: PRT
<213> ORGANISM: Artificial Sequence
<220> FEATURE:
<223> OTHER INFORMATION: N6his-linker-s11-SR fusion polypeptide

<400> SEQUENCE: 66

Met Gly His His His His His Gly Gly Gly Ser Thr Ser Arg Asp
1               5                   10                  15

His Met Val Leu His Glu Tyr Val Asn Ala Ala Gly Ile Thr Gly Thr
            20                  25                  30

Asp Gly Ser Gly Gly Gly Ser His Met Pro Val Lys Cys Pro Gly
        35                  40                  45

Glu Tyr Gln Val Asp Gly Lys Lys Val Ile Leu Asp Glu Asp Cys Phe
    50                  55                  60

Met Gln Asn Pro Glu Asp Trp Asp Glu Lys Val Ala Glu Trp Leu Ala
65                  70                  75                  80

Arg Glu Leu Glu Gly Ile Gln Lys Met Thr Glu Glu His Trp Lys Leu
                85                  90                  95

Val Lys Tyr Leu Arg Glu Tyr Trp Glu Thr Phe Gly Ser Cys Pro Pro
            100                 105                 110

Ile Lys Met Val Thr Lys Glu Thr Gly Phe Ser Leu Glu Lys Ile Tyr
        115                 120                 125

Gln Leu Phe Pro Ser Gly Pro Ala His Gly Ala Cys Lys Val Ala Gly
    130                 135                 140

Ala Pro Lys Pro Thr Gly Cys Val Gly Ser Leu Glu His His His
145                 150                 155                 160

His His

<210> SEQ ID NO 67
<211> LENGTH: 567
<212> TYPE: DNA
```

<213> ORGANISM: Artificial Sequence
<220> FEATURE:
<223> OTHER INFORMATION: Sequence encoding 6his-s11-SR-NLS fusion
      polypeptide

<400> SEQUENCE: 67

```
atgggccacc accaccacca ccacggtggc ggttctacta gtcgtgacca catggtcctt      60
catgagtacg taaatgctgc tgggattaca ggtaccgatg agggtctgg tggcggatca      120
catatgccag tgaaatgtcc cggcgagtac caagttgatg caaaaaagt tatactagac      180
gaggactgtt ttatgcaaaa cccagaggac tgggacgaaa aagtggctga gtggttggcc      240
agagagctag agggcataca aaaaatgacc gaggagcatt ggaagttggt aaaatactta      300
agggagtatt gggagacctt cggctcctgc ccgccaatta aaatggtcac taaagagacg      360
ggcttctcct tggagaaaat ctaccagcta ttccctcgg ggcctgcgca cggagcttgt      420
aaagtggcag gcgcgccgaa gcccacaggc tgcgtcggat ccggtggcgg ttcttccaaa      480
aaagaagaga aagtagatc caaaaagaa gagaaaggta gatccaaaaa agaagagaaa       540
ggtaggatac accggatata actcgag                                          567
```

<210> SEQ ID NO 68
<211> LENGTH: 188
<212> TYPE: PRT
<213> ORGANISM: Artificial Sequence
<220> FEATURE:
<223> OTHER INFORMATION: 6his-S11-SR-NLS fusion polypeptide

<400> SEQUENCE: 68

```
Met Gly His His His His His His Gly Gly Gly Ser Thr Ser Arg Asp
1               5                   10                  15
His Met Val Leu His Glu Tyr Val Asn Ala Ala Gly Ile Thr Gly Thr
            20                  25                  30
Asp Gly Gly Ser Gly Gly Gly Ser His Met Pro Val Lys Cys Pro Gly
        35                  40                  45
Glu Tyr Gln Val Asp Gly Lys Lys Val Ile Leu Asp Glu Asp Cys Phe
    50                  55                  60
Met Gln Asn Pro Glu Asp Trp Asp Glu Lys Val Ala Glu Trp Leu Ala
65                  70                  75                  80
Arg Glu Leu Glu Gly Ile Gln Lys Met Thr Glu Glu His Trp Lys Leu
                85                  90                  95
Val Lys Tyr Leu Arg Glu Tyr Trp Glu Thr Phe Gly Ser Cys Pro Pro
            100                 105                 110
Ile Lys Met Val Thr Lys Glu Thr Gly Phe Ser Leu Glu Lys Ile Tyr
        115                 120                 125
Gln Leu Phe Pro Ser Gly Pro Ala His Gly Ala Cys Lys Val Ala Gly
    130                 135                 140
Ala Pro Lys Pro Thr Gly Cys Val Gly Ser Gly Gly Ser Ser Lys
145                 150                 155                 160
Lys Glu Glu Lys Gly Arg Ser Lys Lys Glu Glu Lys Gly Arg Ser Lys
                165                 170                 175
Lys Glu Glu Lys Gly Arg Ile His Arg Ile Leu Glu
            180                 185
```

<210> SEQ ID NO 69
<211> LENGTH: 801
<212> TYPE: DNA
<213> ORGANISM: Artificial Sequence
<220> FEATURE:
<223> OTHER INFORMATION: Sequence encoding 6his-(1-10opt)-NLS fusion -continued polypeptide

<400> SEQUENCE: 69

```
atgggccacc accaccacca ccacggtggc ggttctacta gtatgagcaa aggagaagaa      60
cttttcactg gagttgtccc aattcttgtt gaattagatg gtgatgttaa tgggcacaaa     120
ttttctgtca gaggagaggg tgaaggtgat gctacaatcg gaaaactcac ccttaaattt     180
atttgcacta ctggaaaact acctgttcca tggccaacac ttgtcactac tctgacctat     240
ggtgttcaat gcttttcccg ttatccggat cacatgaaaa ggcatgactt tttcaagagt     300
gccatgcccg aaggttatgt acaggaacgc actatatctt tcaaagatga cgggaaatac     360
aagacgcgtg ctgtagtcaa gtttgaaggt gataccctta ttaatcgtat cgagttaaag     420
ggtactgatt ttaaagaaga tggaaacatt ctcggacaca aactcgagta caactttaac     480
tcacacaatg tatacatcac ggcagacaaa caaaagaatg gaatcaaagc taacttcaca     540
gttcgccaca acgttgaaga tggttccgtt caactagcag accattatca acaaaatact     600
ccaattggcg atggccctgt ccttttacca gacaaccatt acctgtcgac acaaactgtc     660
ctttcgaaag atcccaacga aagggtacc ggatccggtg gcggttcttc caaaaagaa      720
gagaaaggta gatccaaaaa agaagagaaa ggtagatcca aaaagaaga gaaaggtagg     780
atacaccgga tataactcga g                                               801
```

<210> SEQ ID NO 70
<211> LENGTH: 266
<212> TYPE: PRT
<213> ORGANISM: Artificial Sequence
<220> FEATURE:
<223> OTHER INFORMATION: 6his-(1-10opt)-NLS fusion polypeptide

<400> SEQUENCE: 70

Met Gly His His His His His Gly Gly Gly Ser Thr Ser Met Ser
1               5                   10                  15

Lys Gly Glu Glu Leu Phe Thr Gly Val Val Pro Ile Leu Val Glu Leu
            20                  25                  30

Asp Gly Asp Val Asn Gly His Lys Phe Ser Val Arg Gly Glu Gly Glu
        35                  40                  45

Gly Asp Ala Thr Ile Gly Lys Leu Thr Leu Lys Phe Ile Cys Thr Thr
    50                  55                  60

Gly Lys Leu Pro Val Pro Trp Pro Thr Leu Val Thr Thr Leu Thr Tyr
65                  70                  75                  80

Gly Val Gln Cys Phe Ser Arg Tyr Pro Asp His Met Lys Arg His Asp
                85                  90                  95

Phe Phe Lys Ser Ala Met Pro Glu Gly Tyr Val Gln Glu Arg Thr Ile
            100                 105                 110

Ser Phe Lys Asp Asp Gly Lys Tyr Lys Thr Arg Ala Val Val Lys Phe
        115                 120                 125

Glu Gly Asp Thr Leu Val Asn Arg Ile Glu Leu Lys Gly Thr Asp Phe
    130                 135                 140

Lys Glu Asp Gly Asn Ile Leu Gly His Lys Leu Glu Tyr Asn Phe Asn
145                 150                 155                 160

Ser His Asn Val Tyr Ile Thr Ala Asp Lys Gln Lys Asn Gly Ile Lys
                165                 170                 175

Ala Asn Phe Thr Val Arg His Asn Val Glu Asp Gly Ser Val Gln Leu
            180                 185                 190

Ala Asp His Tyr Gln Gln Asn Thr Pro Ile Gly Asp Gly Pro Val Leu

-continued

```
                195                 200                 205
Leu Pro Asp Asn His Tyr Leu Ser Thr Gln Thr Val Leu Ser Lys Asp
        210                 215                 220
Pro Asn Glu Lys Gly Thr Gly Ser Gly Gly Ser Ser Lys Lys Glu
225                 230                 235                 240
Glu Lys Gly Arg Ser Lys Lys Glu Lys Gly Arg Ser Lys Lys Glu
                245                 250                 255
Glu Lys Gly Arg Ile His Arg Ile Leu Glu
                260                 265

<210> SEQ ID NO 71
<211> LENGTH: 570
<212> TYPE: DNA
<213> ORGANISM: Artificial Sequence
<220> FEATURE:
<223> OTHER INFORMATION: Sequence encoding CAL-SR-s11-6his-KDEL fusion
      polypeptide

<400> SEQUENCE: 71
atgctgctat ccgtgccgtt gctgctcggc ctcctcggcc tggccgtcgc cgaccggtcg     60
cacaccatgg gtggcggttc tcatatgcca gtgaaatgtc cggcgagta ccaagttgat    120 ggcaaaaaag ttatactaga cgaggactgt tttatgcaaa acccagagga ctgggacgaa    180
aaagtggctg agtggttggc cagagagcta gagggcatac aaaaaatgac cgaggagcat    240
tggaagttgg taaaatactt aagggagtat tgggagacct tcggctcctg cccgccaatt    300
aaaatggtca ctaaagagac gggcttctcc ttggagaaaa tctaccagct attccccctcg    360 gggcctgcgc acggagcttg taaagtggca ggcgcgccga agccccacag gctgcgtcgga    420 tccgatggag ggtctggtgg cggatcaaca agccgtgacc acatggtcct tcatgagtac    480
gtaaatgctg ctgggattac aggtaccggt ggcggttctc tcgagcacca ccaccaccac    540
cacggtggcg gttctaagga cgagctgtaa                                     570

<210> SEQ ID NO 72
<211> LENGTH: 189
<212> TYPE: PRT
<213> ORGANISM: Artificial Sequence
<220> FEATURE:
<223> OTHER INFORMATION: CAL-SR-s11-6his-KDEL fusion polypeptide

<400> SEQUENCE: 72

Met Leu Leu Ser Val Pro Leu Leu Leu Gly Leu Leu Gly Leu Ala Val
1               5                   10                  15

Ala Asp Arg Ser His Thr Met Gly Gly Gly Ser His Met Pro Val Lys
            20                  25                  30

Cys Pro Gly Glu Tyr Gln Val Asp Gly Lys Lys Val Ile Leu Asp Glu
        35                  40                  45

Asp Cys Phe Met Gln Asn Pro Glu Asp Trp Asp Glu Lys Val Ala Glu
    50                  55                  60

Trp Leu Ala Arg Glu Leu Glu Gly Ile Gln Lys Met Thr Glu Glu His
65                  70                  75                  80

Trp Lys Leu Val Lys Tyr Leu Arg Glu Tyr Trp Glu Thr Phe Gly Ser
                85                  90                  95

Cys Pro Pro Ile Lys Met Val Thr Lys Glu Thr Gly Phe Ser Leu Glu
            100                 105                 110

Lys Ile Tyr Gln Leu Phe Pro Ser Gly Pro Ala His Gly Ala Cys Lys
        115                 120                 125
```

```
Val Ala Gly Ala Pro Lys Pro Thr Gly Cys Val Gly Ser Asp Gly Gly
    130                 135                 140

Ser Gly Gly Gly Ser Thr Ser Arg Asp His Met Val Leu His Glu Tyr
145                 150                 155                 160

Val Asn Ala Ala Gly Ile Thr Gly Thr Gly Gly Ser Leu Glu His
                165                 170                 175

His His His His His Gly Gly Gly Ser Lys Asp Glu Leu
            180                 185
```

<210> SEQ ID NO 73
<211> LENGTH: 804
<212> TYPE: DNA
<213> ORGANISM: Artificial Sequence
<220> FEATURE:
<223> OTHER INFORMATION: Sequence encoding CAL-(1-10opt)-6his-KDEL
      fusion polypeptide

<400> SEQUENCE: 73

```
atgctgctat ccgtgccgtt gctgctcggc ctcctcggcc tggccgtcgc cgaccggtcg      60
cacaccatgg gtggcggttc tcatatgatg agcaaaggag aagaactttt cactggagtt     120
gtcccaattc ttgttgaatt agatggtgat gttaatgggc acaaattttc tgtcagagga     180
gagggtgaag gtgatgctac aatcggaaaa ctcacccta aatttatttg cactactgga      240
aaactacctg ttccatggcc aacacttgtc actactctga cctatggtgt caatgctttt     300
tcccgttatc cggatcacat gaaaaggcat gacttttca agagtgccat gcccgaaggt      360
tatgtacagg aacgcactat atctttcaaa gatgacggga atacaagac gcgtgctgta     420 gtcaagtttg aaggtgatac ccttgttaat cgtatcgagt taaagggtac tgattttaaa     480
gaagatggaa acattctcgg acacaaactc gagtacaact ttaactcaca caatgtatac     540
atcacggcag acaaacaaaa gaatggaatc aaagctaact tcacagttcg ccacaacgtt     600
gaagatggtt ccgttcaact agcagaccat atcaacaaa atactccaat ggcgatggc      660 cctgtccttt taccagacaa ccattacctg tcgacacaaa ctgtcctttc gaaagatccc     720
aacgaaaagg gtaccggtac cggtggcggt tctctcgagc accaccacca ccaccacggt     780
ggcggttcta aggacgagct gtaa                                             804
```

<210> SEQ ID NO 74
<211> LENGTH: 267
<212> TYPE: PRT
<213> ORGANISM: Artificial Sequence
<220> FEATURE:
<223> OTHER INFORMATION: CAL-(1-10opt)-6his-KDEL fusion polypeptide

<400> SEQUENCE: 74

```
Met Leu Leu Ser Val Pro Leu Leu Leu Gly Leu Leu Gly Leu Ala Val
1               5                   10                  15

Ala Asp Arg Ser His Thr Met Gly Gly Gly Ser His Met Met Ser Lys
                20                  25                  30

Gly Glu Glu Leu Phe Thr Gly Val Val Pro Ile Leu Val Glu Leu Asp
            35                  40                  45

Gly Asp Val Asn Gly His Lys Phe Ser Val Arg Gly Glu Gly Glu Gly
        50                  55                  60

Asp Ala Thr Ile Gly Lys Leu Thr Leu Lys Phe Ile Cys Thr Thr Gly
65                  70                  75                  80

Lys Leu Pro Val Pro Trp Pro Thr Leu Val Thr Thr Leu Thr Tyr Gly
                85                  90                  95
```

-continued

```
Val Gln Cys Phe Ser Arg Tyr Pro Asp His Met Lys Arg His Asp Phe
            100                 105                 110

Phe Lys Ser Ala Met Pro Glu Gly Tyr Val Gln Glu Arg Thr Ile Ser
        115                 120                 125

Phe Lys Asp Asp Gly Lys Tyr Lys Thr Arg Ala Val Val Lys Phe Glu
        130                 135                 140

Gly Asp Thr Leu Val Asn Arg Ile Glu Leu Lys Gly Thr Asp Phe Lys
145                     150                 155                 160

Glu Asp Gly Asn Ile Leu Gly His Lys Leu Glu Tyr Asn Phe Asn Ser
                165                 170                 175

His Asn Val Tyr Ile Thr Ala Asp Lys Gln Lys Asn Gly Ile Lys Ala
                180                 185                 190

Asn Phe Thr Val Arg His Asn Val Glu Asp Gly Ser Val Gln Leu Ala
            195                 200                 205

Asp His Tyr Gln Gln Asn Thr Pro Ile Gly Asp Gly Pro Val Leu Leu
        210                 215                 220

Pro Asp Asn His Tyr Leu Ser Thr Gln Thr Val Leu Ser Lys Asp Pro
225                 230                 235                 240

Asn Glu Lys Gly Thr Gly Thr Gly Gly Gly Ser Leu Glu His His His
                245                 250                 255

His His His Gly Gly Gly Ser Lys Asp Glu Leu
                260             265
```